US006627426B2

(12) United States Patent
Biddle et al.

(10) Patent No.: US 6,627,426 B2
(45) Date of Patent: Sep. 30, 2003

(54) METHODS FOR REDUCING ADVENTITIOUS AGENTS AND TOXINS AND CELL CULTURE REAGENTS PRODUCED THEREBY

(75) Inventors: William C. Biddle, Buffalo, NY (US); Richard M. Fike, Clarence, NY (US); Barbara M. Dadey, East Aurora, NY (US); Thomas E. Bulera, Lancaster, NY (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/576,900

(22) Filed: May 23, 2000

(65) Prior Publication Data

US 2002/0015999 A1 Feb. 7, 2002

Related U.S. Application Data

(63) Continuation of application No. 09/343,686, filed on Jun. 30, 1999, now abandoned.
(60) Provisional application No. 60/091,275, filed on Jun. 30, 1998, provisional application No. 60/040,314, filed on Feb. 14, 1997, provisional application No. 60/058,716, filed on Sep. 12, 1997, and provisional application No. 60/062,192, filed on Oct. 16, 1997.

(51) Int. Cl.$^7$ .............. C12N 1/00; C12N 1/22; C12N 1/14; C12N 5/00; C12N 5/02
(52) U.S. Cl. .............. 435/243; 435/252; 435/254; 435/325; 435/355; 435/420
(58) Field of Search .............. 435/243, 325, 435/355, 420, 252, 254; 436/18; 422/45, 140, 141

(56) References Cited

U.S. PATENT DOCUMENTS

| 2,835,586 A | | 5/1958 | Peebles |
| 3,771,237 A | | 11/1973 | Hansen et al. |
| 4,053,642 A | | 10/1977 | Hup et al. |
| 4,071,412 A | | 1/1978 | Eisenberg et al. |
| 4,072,570 A | * | 2/1978 | Williams |
| 4,073,951 A | * | 2/1978 | Sargeant |
| 4,490,403 A | * | 12/1984 | Pisecky et al. |
| 4,511,592 A | | 4/1985 | Percel et al. |
| 4,544,637 A | | 10/1985 | Keggins et al. |
| 4,615,978 A | | 10/1986 | Sandine et al. |
| 4,620,908 A | | 11/1986 | Van Duzer |
| 4,621,058 A | | 11/1986 | Reddy |
| 4,632,980 A | | 12/1986 | Zee et al. |
| 4,689,297 A | | 8/1987 | Good et al. |
| 4,820,627 A | | 4/1989 | McGeehan |
| 4,885,848 A | | 12/1989 | Christensen |
| 4,975,246 A | * | 12/1990 | Charm |
| 4,999,301 A | | 3/1991 | Bryan-Jones |
| 5,006,204 A | | 4/1991 | Jensen |
| 5,133,137 A | * | 7/1992 | Petersen |
| 5,155,039 A | | 10/1992 | Chrisope et al. |
| 5,325,606 A | * | 7/1994 | Liborius |
| 5,357,688 A | | 10/1994 | Christensen |
| 5,366,696 A | * | 11/1994 | Williams |
| 5,392,531 A | * | 2/1995 | Christensen et al. |
| 5,474,931 A | | 12/1995 | DiSorbo et al. |
| 5,518,709 A | * | 5/1996 | Sutton et al. |
| 5,580,856 A | | 12/1996 | Prestrelski et al. |
| 5,700,426 A | | 12/1997 | Schmitthaeusler et al. |
| 5,756,046 A | | 5/1998 | Winks et al. |
| 5,773,279 A | | 6/1998 | Miller et al. |
| 5,811,406 A | | 9/1998 | Szoka, Jr. et al. |
| 5,869,321 A | | 2/1999 | Franklin |

FOREIGN PATENT DOCUMENTS

| CZ | 169007 | | 6/1976 |
| DK | 167090 B1 | | 8/1993 |
| EP | 0049632 | * | 10/1981 |
| EP | 0 049 632 A2 | | 4/1982 |
| EP | 0 155 427 A1 | | 9/1985 |
| EP | 0 356 071 A2 | | 2/1990 |
| GB | 1 355 192 | | 6/1974 |
| JP | 51098354 | * | 8/1976 |
| JP | 57152882 | * | 9/1982 |
| JP | 1-157395 | | 6/1989 |
| JP | 04198137 | * | 7/1992 |
| SU | 1097253 | | 6/1984 |
| WO | WO 94/27645 | | 12/1994 |
| WO | WO 95/00031 | | 1/1995 |
| WO | WO 95/13867 | | 5/1995 |
| WO | WO 96/23868 | | 8/1996 |
| WO | WO 97/11157 | | 3/1997 |
| WO | WO 97/38734 | | 10/1997 |
| WO | WO 97/42980 | | 11/1997 |
| WO | WO 98/15297 | * | 4/1998 |

OTHER PUBLICATIONS

Hampel, et al., The Encyclopedia of Chemistry, "Sterilization (Industrial)", pp. 1052–1053. Litton Educational Publishing, Inc.*

(List continued on next page.)

*Primary Examiner*—Christopher R. Tate
*Assistant Examiner*—Michele Flood
(74) *Attorney, Agent, or Firm*—Sterne, Kessler, Goldstein & Fox, P.L.L.C.

(57) ABSTRACT

The present invention relates generally to a method to reduce, substantially reduce, inactivate or eliminate adventitious agents and/or toxins in a sample, particuarly in nutritive media, media supplements, media subgroups and buffer formulations. Specifically, the present invention provides powdered nutritive media, media supplements and media subgroups produced by the methods of the invention, particuarly cell culture media supplements (including powdered sera such as powdered fetal bovine serum (FBS)). The invention further provides powdered buffer formulations produced by the methods of the invention. The invention also provides kits and methods for cultivation of prokaryotic and eukaryotic cells, particularly bacterial cells, yeast cells, plant cells and animal cells (including human cells) using these nutritive media, media supplements, media subgroups and buffer formulations. The invention also relates to methods for producing storage stable cells having reduced, substantially reduced or eliminated adventitious agents or toxins.

19 Claims, 25 Drawing Sheets

OTHER PUBLICATIONS

Davis et al., Microbiology, Chapter 67, "Sterilization and Disinfection", pp. 1264–1274, Harper & Row Publishers, Inc.*

Frazier et al., Food Microbiology, Chapters 5 & 8, pp. 122–127, 161, 434–436, and 444–445, Mc–Graw–Hill, Inc.*

Reinert et al., Plant Cell and Tissue Culture, pp. 74 and 76, Springer–Verlag, Berlin Heidelberg.*

Rohde, et al., BBL Manual of Products & Laboratory Procedures, pp. 97, 101, 111, 123, BBL–Becton Dickinson & Co.*

Downes et al., S. Afr. J. Anim. Sci., 17: 2, pp. 55–58. The relative nutritive value of irradiated spray–dried blood powder and heat–sterilized blood meal as measured in combination with whey protein.*

Camire et al., In Vitro, 34(3), Part II, V–1008. Efficient cultivation of cells using powdered serum.*

Robey et al., In Vitro, 34(3), Part II, V–1007. A comparison of the effects of powdered and liquid fetal bovine serum on normal human cell growth, metabolism and urokinase formation.*

Camire, J.C.F., et al., "Efficient Cultivation of Cells Using Powdered Serum," In Vitro 34:Abstract No. V–1008 (Mar. 1998).

Davis, B., et al., "Sterilization and Disinfection," in *Microbiology*, Ch. 67, Harper and Row Publishers, Inc., pp. 1264–1274 (1973).

Downes, T.E.H., et al., "The relative nutritive value of irratiated spray–dried blood powder and heat–sterilized blood meal as measured in combination with whey protein," *Suid Afrikaanse Tydskrif Vir Veekunde* (*S. Afr. J. Anim. Sci.*) 17:55–58 (1987).

Frazier, W.C., et al., "General Principles of Food Preservation: Asepsis, Removal, Anaerobic Conditions," in *Food Microbiology*, 3$^{rd}$ ed., McGraw–Hill Book Company, pp. 93–99, 122–123, 126–127, 143–153, 161, 434–436, 444–445 (1978).

Freshney, R.I., "The Culture Environment: II. Media and Supplements," in *Culture of Animal Cells: A Manual of Basic Technique*, Alan R. Liss, Inc., New York, NY, pp. 74–78 (1983).

GEA Process Technology Division, Aeromatic–Fielder Division, Columbia, MD, technical brochure entitled "Batch fluid beds: Customized fluid bed systems for solids processing."

GEA Pharmacuetical Processing, Columbia, MD, Marketing brochure entitled "Plant and Process Technology by the GEA Companies."

"Granulated Media," in *Microbiology Catalog*, EM Science, Cincinnati, Ohio (1999).

Hampel, C., et al., "Sterilization (Industrial)," in *The Encyclopedia of Chemistry*, Litton Educational Publishing, Inc., pp. 1052–1053 (1973).

Harlow, E., and Lane, D., "Sampling Serum," In: *Antibodies: A Laboratory Manual*, Cold Spring Harbor Laboratory (1988).

Niro, Inc., Technical Bulletin No. 95001 entitled "Fluid Bed Multi–Processor," Aeromatic–Fielder Division, Columbia, MD (1995).

Marketing brochure for EZMix Fermentation Media, Sigma, St. Louis, MO, (publication date before Oct. 1996).

Reinert, J., et al., "Sterilization," "Culture Media," "Composition of Culture Media," in *Plant Cell and Tissue Culture. A Laboratory Manual*, Springer–Verlag, Berlin Heidelberg, pp. 74, 76–77 (1982).

Rohde, B.A., et al., BBL Manual of Products and laboratory Procedures, BBL–Becton Dickinson & Co., pp. 97, 101, 111, 123 (1973).

Robey, T.E., and Ryan, J.M, "A Comparison of the Effects of Powdered and Liquid Fetal Bovine Serum on Normal Human Cell Growth, Metabolism and Urokinase Formation," In Vitro 34:Abstract No. V–1007 (Mar. 1998).

Dialog File 351, Derwent WPI, Accession No. 76–44200X/197624, English language abstract for Denmark Patent Publication No. DK 167090 B1.

Product and Corporate Information, American Protein Corporation, <http://www.AmericanProtein.com/index.html> (Jul. 1999).

WIPDS Database on STN, Accession No. 85–005539, English language abstract for Soviet Union Patent Publication No. SU 1097253.

Brock, T.D., et al., "Acidity and pH," in *Biology of Microorganisms*, 4$^{th}$ edition, Brock, T.D., et al., eds., Prentice–Hall, Englewood Cliffs, NJ, pp. 257–260.

Hana, L., et al., "Preservation of sera, protein fractions, and Tissue cultures media by spray drying," (English language abstract for CS 169,007 (Document No. AO2)), *Chem. Abstracts*88: Abstract No. 118718 (1978).

Hay, R., et al., "American Type Culture Collection Catalogue of Cell Lines and Hybridomas," 6$^{th}$ Ed., ATCC, Rockville, MD, p. 347 (1988).

Jensen, J.D., "(Some recent advances in) Agglomerating, Instantizing, and Spray Drying," *Food Technol.* 29:60–71, Institute of Food Technologists (1975).

Life Technologies, Inc., "GIBCO–BRL 1995–1996 Product Catalogue and Reference Guide," Thomson Print Services Ltd., Glasgow, Scotland, pp. 1–18, 1–24, and 1–7 (1995).

Life Technologies, Inc., "GIBCO–BRL 1996–1997 Catalogue for Cell Culture," Thomson Print Services Ltd., Glasgow, Scotland, p. 16 and p. 56 (1996).

Life Technologies, Inc., "GIBCO–BRL 1996–1997 Catalogue for Cell Culture," Thomson Print Services Ltd., Glasgow, Scotland, pp. 79–84 (1996).

Pending Non–Provisional U.S. patent application Ser. No. 09/606,314, Fike et al., filed Jun. 29, 2000 (Not Published).

Pending Non–Provisional U.S. patent application Ser. No. 09/705,940, Fike et al., filed Nov. 6, 2000 (Not Published).

Derwent World Patent Index, Accession No. 1976–78201X, English language abstract for JP 51–98354 (Document AP2).

Derwent World Patent Index, Accession No. 1982–91800E, English language abstract for JP 57–152882 (Document AM3).

Dialog File 351, Accession No. 4411606, Derwent WPI English language abstract for EP 0 155 427 A1 (Document AN3).

Derwent World Patent Index, Accession No. 1989–218070, English language abstract for JP 1–157395 (Document AO3).

JPO English language abstract for JP 4–198137 (Document AP3).

Supplementary European Search Report for European Application No. EP 98 90 8542, completed Sep. 9, 2002.

* cited by examiner

FIG. 17A

METHODS FOR REDUCING ADVENTITIOUS AGENTS AND TOXINS AND CELL CULTURE REAGENTS PRODUCED THEREBY

CROSS REFERENCE TO RELATED APPLICATIONS

This application is a continuation of U.S. patent application Ser. No. 09/343,686, filed Jun. 30, 1999, now abandoned, which claims the benefit of the filing date of U.S. Patent Application No. 60/091,275, filed Jun. 30, 1998. This application also relates to U.S. Patent Application No. 60/040,314, filed Feb. 14, 1997, No. 60/058,716, filed Sep. 12, 1997, No. 60/062,192, filed Oct. 16, 1997, and Ser. No. 09/023,790, filed Feb. 13, 1998. The disclosures of all of the above-referenced applications are entirely incorporated herein by reference.

FIELD OF THE INVENTION

The present invention relates generally methods for reducing, substantially reducing or eliminating adventitious agents (such as viruses, bacteria, mycoplasma, and non-cellular compounds such as proteins that result in acute or chronic toxicity/disease (i.e. prions)) in any sample (including liquid or dry samples). Thus, the invention relates to sterilization or substantial sterilization of such samples. More specifically, the present invention provides liquid and dry powder cell culture reagents including nutrients or ingredients utilized by cells in cell culture, and to nutritive medium formulations produced by such methods, particularly cell culture medium formulations comprising all of the necessary nutritive factors that facilitate the in vitro cultivation of cells. Such nutrients or ingredients may comprise one or more proteins, carbohydrates, lipids, amino acids, vitamins, nucleic acids, DNA, RNA, trace metals and buffers either alone or in combination. The invention also relates to liquid and dry powder media supplements, such as liquid or dry powder blood derived products such as sera (e.g., fetal bovine serum or other animal (i.e. porcine, horse, fish, etc.) or human origin sera) produced by the methods of the invention. The invention also relates to liquid and dry powder buffer formulations and media subgroups produced by the methods of the invention. The present invention also relates to kits containing samples produced by the invention, particularly cell culture reagents such as nutrients, media, media supplements, media subgroups, as well as methods for cultivation of prokaryotic and eukaryotic cells using these cell culture reagents.

BACKGROUND OF THE INVENTION

Cell Culture Media

Cell culture media provide the nutrient necessary to maintain and grow cells in a controlled, artificial and in vitro environment. Characteristics and compositions of the cell culture media vary depending on the particular cellular requirements. Important parameters include osmolality, pH, and nutrient formulations.

Media formulations have been used to cultivate a number of cell types including animal, plant, yeast and prokaryotic cells including bacterial cells. Cells cultivated in culture media catabolize available nutrients and produce useful biological substances such as monoclonal antibodies, hormones, growth factors, viruses and the like. Such products have therapeutic applications and, with the advent of recombinant DNA technology, cells can be engineered to produce large quantities of these products. Thus, the ability to cultivate cells in vitro is not only important for the study of cell physiology, but is also necessary for the production of useful substances which may not otherwise be obtained by cost-effective means.

Cell culture media formulations have been well documented in the literature and a number of media are commercially available. In early cell culture work, media formulations were based upon the chemical composition and physicochemical properties (e.g., osmolality, pH, etc.) of blood and were referred to as "physiological solutions" (Ringer, S., *J Physiol.* 3:380–393 (1880); Waymouth, C., In: *Cells and Tissues in Culture*, Vol. 1, Academic Press, London, pp. 99–142 (1965); Waymouth, C., *In Vitro* 6:109–127 (1970)). However, cells in different tissues of the mammalian body are exposed to different microenvironments with respect to oxygen/carbon dioxide partial pressure and concentrations of nutrients, vitamins, and trace elements; accordingly, successful in vitro culture of different cell types may require the use of different media formulations. Typical components of cell culture media include amino acids, organic and inorganic salts, vitamins, trace metals, sugars, lipids and nucleic acids, the types and amounts of which may vary depending upon the particular requirements of a given cell or tissue type.

Typically, cell culture media formulations are supplemented with a range of additives, including undefined components such as fetal bovine serum (FBS) (10–20% v/v) or extracts from animal embryos, organs or glands (0.5–10% v/v). While FBS is the most commonly applied supplement in animal cell culture media, other serum sources are also routinely used, including newborn calf, horse and human. Organs or glands that have been used to prepare extracts for the supplementation of culture media include submaxillary gland (Cohen, S., *J. Biol. Chem.* 237:1555–1565 (1961)), pituitary (Peehl, D. M., and Ham, R. G., *In Vitro* 16:516–525 (1980); U.S. Pat. No. 4,673,649), hypothalamus (Maciag, T., et al., *Proc. Natl. Acad. Sci. USA* 76:5674–5678 (1979); Gilchrest B. A., et al, *J. Cell. Physiol.* 120:377–383 (1984)), ocular retina (Barretault, D., et al., *Differentiation* 8:29–42 (1981)) and brain (Maciag, T., et al., *Science* 211:1452–1454 (1981)). Cell culture media may also contain other animal-derived products, including but not limited to blood-derived products (e.g., serum, albumin, antibodies, fibrinogen, factor VIII, etc.), tissue or organ extracts and/or hydrolysates (e.g., bovine pituitary extract (BPE), bovine brain extract, chick embryo extract and bovine embryo extract), and animal-derived lipids, fatty acids, proteins, amino acids, peptones, Excyte™, sterols (e.g., cholesterol) and lipoproteins (e.g., high-density and low-density lipoproteins (HDLs and LDLs, respectively)). Cell culture media may also contain specific purified or recombinant growth factors for example: insulin, fibroblast growth factor (FGF), epidermal grouch factors (EGF), transferrin, hematopoietic growth factors like erythropoietin. IL, 1, 2, 3, 4, 5, 6, 7, 8, 9, 10, 11, etc., colony stimulating factors like G-CSF, GM-CSF, histotypic specific growth factors like neural growth factors, specific regulators of cAMP or other signal transductive pathways etc. These types of supplements serve several useful functions in cell culture media (Lambert, K. J. et al., In: *Animal Cell Biotechnology*, Vol. 1, Spier, R. E. et al., Eds., Academic Press New York, pp. 85–122 (1985)). For example, these additives provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, animal derived products are commonly used as relatively low-cost supplements to provide an optimal culture medium for the cultivation of animal cells.

Unfortunately, the use of such animal derived components or nutrients in tissue or cell culture applications has several drawbacks (Lambert, K. J., et al., In: *Animal Cell Biotechnology*, Vol. 1, Spier, R. E., et al., Eds., Academic Press New York, pp. 85–122 (1985)). Foremost is the potential to contaminate tissue or cell cultures with adventitious agents or toxins. Indeed, supplementation of media with animal or human derived components may introduce infectious agents (e.g., mycoplasma and/or viruses) or toxins which can seriously undermine the health of the cultured cells when these contaminated supplements are used in cell culture media formulations, and may result in the production of biological substances (e.g. antibodies, hormones, growth factors etc.) which are contaminated with infectious agents or toxins. Thus, contamination of cell or tissue cultures with adventitious agents or toxins may pose a health risk in cell therapy and in other clinical applications. A major fear is the presence of non-cellular soluble or insoluble proteins or other classes of bioactive components that may have disease pathogenesis, and in particular the presence of prions causing spongiform encephalopathy in humans or animals.

Thus, there exists a current need to reduce or eliminate adventitious agents (e.g. infectious agents) and toxins from cell culture reagents (e.g. nutritive media, media supplements, media subgroups, buffers and any nutritive components or solutions which may be found in cell culture media including proteins, carbohydrates, lipids, amino acids, vitamins, nucleic acids, DNA, RNA, trace metals and buffers either alone or in combination). Such cell culture reagents having reduced or eliminated adventitious agents or toxins will be particularly important to the pharmaceutical and medical industry.

SUMMARY OF THE INVENTION

The present invention addresses this need. Generally, the invention relates to treating any sample to reduce, substantially reduce, inactivate, or eliminate adventitious agents or toxins present in the sample of interest. More specifically, the invention relates to cell culture reagents such as nutritive media, media supplements, media subgroups and buffers (or any ingredient used to make them).

In accordance with the invention, such reduction, inactivation, or elimination of contaminating adventitious agents or toxins is accomplished by drying or substantially drying the sample of interest. Preferably, the sample of interest is exposed to air or other gas (or combination of gases) under conditions sufficient to reduce, substantially reduce, inactivate or eliminate toxins and/or adventitious agents present in the sample. The sample exposed to the air or gas can be in dry (e.g. powdered) or liquid form. Preferably, such conditions involve increasing the surface area of the sample exposed to the air or gas or combination of gases. Increasing the surface area of the sample exposed to air or other gas (or combination of gases) may involve any method in which the particle size of the sample (e.g. in liquid or dry form) in the air or gas is decreased and/or the volume of the sample exposed to the air or gas is increased. Increasing surface area exposure of the sample may be accomplished by atomizing, pulverizing, grinding, dispensing, spraying, misting, dripping, pouring, spreading etc. the dry or liquid sample in and/or through the air or gases. Alternatively, the air or gas may be injected, bubbled, sprayed, etc. through the dry or liquid sample. Preferably, the air/gas is introduced as a volatile, turbulent stream which promotes uniform or homogeneous dispersion and/or agglomeration.

In accordance with the invention, other environmental conditions such as temperature (e.g. heating or cooling or freezing), humidity, atmospheric pressure, gas or air content, time of exposure etc. may be adjusted or optimized during exposure of the sample to the air or gases to facilitate reduction or removal of adventitious agents and toxins. Preferably, heat is applied during exposure of the sample to air or gas (or combination of gases) to facilitate reduction or removal of adventitious agents or toxins from the sample and/or to facilitate drying of the sample, although cooling or freezing temperatures may be applied during exposure. In another aspect, the type of gas or combination of gases as well as the amount (e.g. percentage) of each gas present can be changed or optimized to further assist in reduction or elimination of adventitious agents or toxins. Such gas or gases include but are not limited to ozone, nitrogen, helium, air, carbon dioxide, argon, oxygen, hydrogen etc. In another aspect, chemical or biological compounds or conditions which are toxic or inhibitory to adventitious agents or toxins may be added during or after the process to neutralize or inactivate such agents or toxins. Such compounds or conditions which may be added or varied include but are not limited to antibiotics, hydrochloric acid, sodium hydroxide, antibodies (monoclonal or polyclonal antibodies or fragments thereof), iodine, pH treatment, ozone, $\alpha$-gamma rays, psoralen or like reagents, porphyrins or derivatives of chlorins or other photoactive reagents or compounds.

Preferably, the sample of interest (which is preferably any cell culture reagent, particularly a media, media supplement, media subgroup or buffer) is dispersed or sprayed into a chamber or other container containing air or gas (or a combination of gases) and most preferably the sample (e.g. dry or liquid form) is subjected to spray drying or agglomeration by procedures well known in the art. Such procedures may involve, for example, the use of a spray drying apparatus and/or a fluid bed apparatus or combinations thereof or similar technology available in the art. In a preferred aspect, a liquid sample is sprayed in the presence of heat under conditions sufficient to dry or substantially dry the sample while a dry or substantially dry sample (preferably in powdered or granular form) is dispersed (e.g. in a chamber) with blowing or pressurized air or gas in the presence of heat. Preferably, such dispersing or spraying is performed under conditions sufficient to reduce, substantially reduce, inactivate or eliminate adventitious agents or toxins in the sample. Such conditions may include, for example, controlling humidity, atmospheric pressure, the content and/or type of gas used, time of exposure, and addition of compounds, to facilitate reduction, inactivation or elimination of toxins or adventitious agents.

Thus, the present invention comprises exposing a sample to air or gas (or combination of gases) under conditions sufficient to reduce, substantially reduce, inactivate or eliminate adventitious agents and/or toxins in said sample. More specifically, the invention comprises:

exposing a sample (preferably a medium, a medium subgroup, a medium supplement or a buffer) to air or gas (or combination of gases) which may contain one or more cellular or non-cellular adventitious agents and/or one or more toxins, preferably by spraying or dispersing said sample in or through said air or gas (or combination of gases), and preferably in the presence of heat; and obtaining a sample having reduced, substantially reduced, inactivated or eliminated adventitious agents and/or toxins compared to the untreated sample. Such sample produced is preferably in dry form (e.g. powdered).

To further facilitate reduction, substantial reduction, inactivation or elimination of adventitious agents or toxins in the sample of interest, the invention may further comprise sterilizing the sample produced by the methods of the invention. Such sterilization may be accomplished by irradiation or other sterilization methods well known to those of ordinary skill in the art. Preferably, the sample produced by the invention (for example by spray drying or agglomeration) may be sterilized prior to or after packaging. In particularly preferred embodiments, sterilization is accomplished after packaging by irradiation of the packaged material with gamma rays.

Particularly preferred nutritive medium that may be produced according to the invention include culture medium selected from the group consisting of a bacterial culture medium, a yeast culture medium, a plant culture medium and an animal culture medium. In a preferred aspect, such culture media are produced in dry powdered form, although they may be produced in liquid form (e.g., by admixing with one or more solvents).

Particularly preferred media supplements that may be produced by the methods of the invention include: blood derived products such as animal sera including bovine sera (e.g., fetal bovine, newborn calf or normal calf sera), human sera, equine sera, porcine sera, monkey sera, ape sera, rat sera, murine sera, rabbit sera, ovine sera and the like; cytokines (including growth factors such as EGF, aFGF, bFGF, HGF, IGF-1, IGF-2, NGF and the like, interleukins, colony-stimulating factors and interferons); attachment factors or extracellular matrix components (such as collagens, laminins, proteoglycans, glycosaminoglycans, fibronectin, vitronectin and the like); lipids (such as phospholipids, cholesterol, bovine cholesterol concentrate, fatty acids, Excyte™, sphingolipids and the like); and extracts or hydrolysates of tissues, cells, organs or glands from animals, plants, insects, fish, yeast, bacteria or any other prokaryotic or eukaryotic source (such as bovine pituitary extract, bovine brain extract, chick embryo extract, yeast extract, bovine embryo extract, chicken meat extract, achilles tendon and extracts thereof) and the like). Other media supplements that may be produced by the present methods include a variety of proteins (such as serum albumins, particularly bovine or human serum albumins; immunoglobulins and fragments or complexes thereof; aprotinin; hemoglobin; haemin or haematin; enzymes (such as trypsin, collagenases, pancreatinin or dispase); lipoproteins; ferritin; etc.)) which may be natural or recombinant, vitamins, amino acids and variants thereof (including, but not limited to, L-glutamine and cystine), enzyme co-factors and other components useful in cultivating cells in vitro that will be familiar to one of ordinary skill. Preferably, such supplements are produced in dry powdered form but may be produced in liquid form by, for example, mixing one or more solvents with the dry powdered supplement of interest.

The nutritive media and media supplements prepared by the invention may also comprise subgroups such as serum (preferably those described above), L-glutamine, insulin, transferrin, one or more lipids (preferably one or more phospholipids, sphingolipids, fatty acids or cholesterol), one or more cytokines (preferably those described above), one or more neurotransmitters, one or more extracts or hydrolysates of tissues, organs or glands (preferably those described above), one or more proteins (preferably those described above) or one or more buffers (preferably sodium bicarbonate), or any combination thereof.

Buffers particularly suitable for preparation according to the methods of the invention include buffered saline powders, most particularly phosphate-buffered saline or Tris-buffered saline and buffers used in clinical or electrolyte solutions (i.e. Ringer's, Ringer's lactate, parenteral nutrition solutions or powders). In accordance with the invention, such buffers may be in powdered or liquid form.

The invention also relates to methods of preparing cells, cell cultures, or cell preparations in which the level of toxins, adventitious agents or other detrimental components are reduced or eliminated. Such cells include prokaryotic (e.g., bacterial) and eukaryotic (e.g., fungal (especially yeast), animal (especially mammalian, including human) and plant cells. This method of the invention thus may comprise obtaining one or more cells and subjecting said cells to the methods of the invention under conditions sufficient to reduce, substantially reduce, inactivate or eliminate one or more toxins and/or one or more adventitious agents. In this aspect of the invention, the conditions (e.g. temperature, humidity, atmospheric pressure, type of gases, gas flow and gas flow pattern (e.g., volatile or turbulent stream) etc.) used may be optimized or adjusted to avoid or substantially avoid adversely affecting the cells of interest. Preferably, conditions are used such that the viability of such cells are not reduced or substantially reduced. Thus, the invention relates to exposing a sample comprising cells with air or gas (or combination of gases) to reduce, eliminate or inactivate toxins and/or adventitious agents in said sample. The invention also relates to cells produced by these methods, which may be in dry (preferably powdered) or liquid form.

The invention further relates to methods of preparing sterile or substantially sterile samples (preferably cell culture reagents and particularly culture media, media supplements, media subgroups and buffers). One such method comprises exposing the sample (e.g. the above-described culture media, media supplements, media subgroups and buffers) to irradiation (preferably gamma irradiation) such that unwanted bacteria, fungi, spores, viruses etc. that may be resident in the sample are rendered incapable or substantially incapable of replication or growth. In a preferred such method, the sample (e.g. cell culture reagent including media, media supplements, media subgroups and buffers) are gamma irradiated at a total dosage of about 10–100 kilograys (kGy), preferably a total dosage of about 15–75 kGy, 15–50 kGy, 15–40 kGy or 20–40 kGy, more preferably a total dosage of about 20–30 kGy, and most preferably a total dosage of about 25 kGy, for about 1 hour to about 7 days, preferably for about 1 hour to about 5 days, more preferably for about 1 hour to about 3 days, about 1 hour to about 24 hours or about 1–5 hours, and most preferably about 1–3 hours. Preferably, powdered samples such as culture media, media supplements, media subgroups and buffers are subjected to such irradiation before or after packaging. Other sterilization processes may also be used alone or in combination with the invention, for example, filtration, ethylene oxide sterilization, autoclaving, and chemical or physical processes such as heat, pH treatment, chemical treatment, treatment with iodine, or photoactive compounds like porphyrin, psoralens, etc.

The invention further provides methods of manipulating or culturing one or more cells comprising contacting said cells with the cell culture reagents of the invention, particularly nutritive media, media supplement, media subgroup or buffer and incubating said cell or cells under conditions favoring the cultivation or manipulation of the cell or cells. Any cell may be cultured or manipulated according to the present methods, particularly bacterial cells, yeast cells, plant cells or animal cells. Preferable animal cells include insect cells (most preferably Drosophila cells, Spodoptera cells and Trichoplusa cells), nematode cells (most preferably *C. elegans* cells) and mammalian cells (most preferably CHO cells, COS cells, VERO cells, BHK cells, AE-1 cells, SP2/0 cells, L5.1 cells, hybridoma cells or human cells, embryonic stem cells (ES cells), cells used for virus or vector production (i.e. 293, PerC 6), cells derived from primary human sites used for cell or gene therapy, i.e., lymphocytes, hematopoietic cells, other white blood cells (WBC), macrophage, neutriophils, and dendritic cells. The invention also pertains to manipulation or cultivation of cells and/or tissues for tissue or organ transplantation or engineering, i.e. hepatocyte, pancreatic islets, osteoblasts, osteoclasts/chondrocytes, dermal or muscle or other connective tissue, epithelial cells, tissues like keratinocytes, cells of neural origin, cornea, skin, organs, and cells used as vaccines, i.e. blood cells, hematopoietic cells other stem cells or progenitor cells, and inactivated or modified tumor cells of various histotypes. Cells cultured or manipulated according to this aspect of the invention may be normal cells, diseased cells, transformed cells, mutant cells, somatic cells, germ cells, stem cells, precursor cells or embryonic cells, any of which may be established cell lines or obtained from natural sources.

The invention is further directed to kits for use in the cultivation or manipulation of one or more cells or tissues. Kits according to the invention may comprise one or more containers comprising one or more samples of the invention, preferably one or more cell culture reagents including nutritive media, media supplements, media subgroups or buffers, or any combination thereof. The kits may also comprise one or more cells or cell types or tissues, including the dried cells of the invention.

Another aspect of the invention relates to compositions comprising cell culture reagents, nutritive media, media supplement, media subgroup, or buffers of the invention and one or more cells or tissues. Such composition may be in powdered or liquid form.

Other preferred embodiments of the present invention will be apparent to one of ordinary skill in light of the following drawings and description of the invention, and of the claims.

BRIEF DESCRIPTION OF THE DRAWINGS

FIG. 16 is a series of line graphs indicating the effect of $\gamma$ irradiation on the ability of transferrin to support the growth of 293 cells over four passages. In each graph, cells were cultured in standard serum-free 293 medium (♦), in medium without transferrin (■), in medium containing powdered transferrin that had been $\gamma$ irradiated at −70° C. (Δ) or room temperature (__), or in medium containing powdered transferrin that had not been $\gamma$ irradiated but that had been stored at −70° C. (x) or at room temperature (●). Results for each data point are the averages of duplicate flasks.

FIG. 17 is a series of bar graphs indicating the effect of $\gamma$ irradiation, under different irradiation conditions, on the ability of FBS to support growth of anchorage-independent cells (FIGS. 17A and 17B) and anchorage-dependent cells (FIGS. 17C and 17D) at first (Px1), second (Px2) and third (Px3) passages.

FIG. 17A: SP2/0 cells;

DETAILED DESCRIPTION OF THE INVENTION

Definitions

Figure 1B:
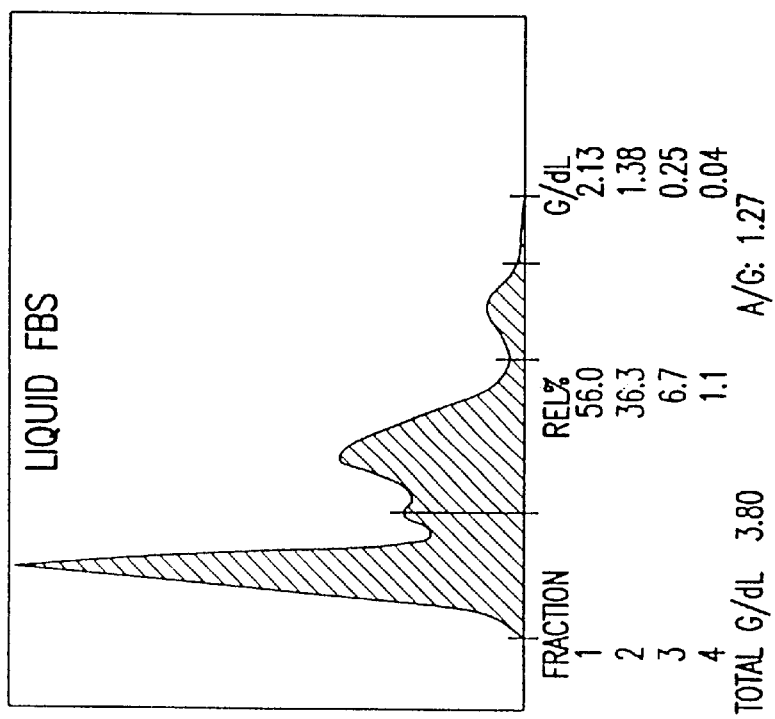
FIG. 1 is a histogram of a densitometric scan of SDS-PAGE of samples of fetal bovine serum (FBS) prepared in powdered form by the methods of the invention (FIG. 1A) and conventional liquid FBS (FIG. 1B).

In the description that follows, a number of terms conventionally used in the field of cell culture media are utilized extensively. In order to provide a clear and consistent understanding of the specification and claims, and the scope to be given such terms, the following definitions are provided.

The term "powder" as used herein refers to a composition that is present in granular form, which may or may not be complexed or agglomerated with a solvent such as water or serum. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, carbohydrates, lipids, nucleic acids, hormones, vitamins, fatty acids, proteins and the like. Other ingredients that promote or maintain cultivation of cells ex vivo can be selected by those of skill in the art, in accordance with the particular need.

The term "cytokine" refers to a compound that induces a physiological response in a cell, such as growth, differentiation, senescence, apoptosis, cytotoxicity or antibody secretion. Included in this definition of "cytokine" are growth factors, interleukins, colony-stimulating factors, interferons and lymphokines.

By "cell culture" or "culture" is meant the maintenance of cells in an artificial, e.g., an in vitro environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

By "cultivation" is meant the maintenance of cells in an artificial environment under conditions favoring growth, differentiation or continued viability, in an active or quiescent state, of the cells. Thus, "cultivation" may be used interchangeably with "cell culture" or any of its synonyms described above.

By "culture vessel" is meant a glass, plastic, or metal container that can provide an aseptic environment for culturing cells.

The phrases "cell culture medium," "culture medium," "nutritive medium" and "medium formulation" (plural "media" in each case) refer to a nutritive solution that supports the cultivation and/or growth of cells; these phrases may be used interchangeably.

By "extract" is meant a composition comprising a concentrated preparation of the subgroups of a substance, typically formed by treatment of the substance (typically a sample of biological origin, e.g. tissues or cells) either mechanically (e.g., by pressure treatment) or chemically (e.g., by distillation, precipitation, enzymatic action or high salt treatment).

By "enzymatic digest" is meant a composition comprising a specialized type of extract, namely one prepared by treating the substance (typically a sample of biological origin, e.g. tissues or cells) to be extracted (e.g. plant components or yeast cells) with at least one enzyme capable of breaking down the components of the substance into simpler forms (e.g., into a preparation comprising mono- or disaccharides and/or mono-, di- or tripeptides). In this context, and for the purposes of the present invention, the term "hydrolysate" may be used interchangeably with the term "enzymatic digest."

By "adventitious agents" is meant any agent such as one or more bacteria, one or more pathogenic microorganisms, one or more microbial pathogens, one or more viruses, one or more mycoplasma, one or more yeast cells, one or more fungi, one or more non cellular compounds that result in acute or chronic toxicity or disease, and the like which may contaminate a sample of interest. Adventitious agents may be present in any number of animal derived products or components used in cell culture reagents. Preferred adventitious agents reduced, eliminated, inactivated or killed by the invention are viruses which may be animal, human, plant, fish, insect, mammalian, DNA, RNA, envelope and non-envelope viruses, regardless of size. Such viruses include Adenoviruses, Herpesviruses, Poxviruses, Popovaviruses, Retroviruses, Orthomyxoviruses (influenza viruses), Paramyxoviruses (parainfluenza, mumps, measles, and respiratory syncytial virus), Picornaviruses (Enteroviruses, Cardioviruses, Rhinoviruses, and Aphthoviruses), Togaviruses, Arenaviruses, Reoviruses, Rotaviruses, Orbiviruses, Rhabdoviruses, Coronaviruses, Marburg Viruses, Ebola Viruses, and Hepatitis Viruses (see "*Comparative Diagnosis of Viral Diseases*", (E. Kurstak and C. Kurstak, eds.), Vol. I–IV, Academic Press, New York, and "*Medical Microbiology and Infectious Diseases*", (A. Samiy, L. Smith, Jr., J. Wyngaarden, eds.), Vol II, W. B. Saunders Co., Philadelphia, Pa.). Examples of such viruses included but are not limited to those shown in the following tables:

Some Animal Viruses

| Virus | Genome | Envelope | Approximate Size (mM) | Comment |
|---|---|---|---|---|
| BVDV | ss-RNA | + | 40–60 | Bovine virus diarrhea |
| IBR | ds-DNA | + | 120–200 | Infect. Bovine Rhinotrachetis |
| PI-3 | ss-RNA | + | 80–160 | Parainfluenza |
| BPV | ss-DNA | − | 25 | Bovine Parvovirus |
| BAV | ds-DNA | − | 70–80 | Bovine Adenoviruses |
| BpoV | ds-DNA | − | 25–35 | Bovine Polyomavirus |
| BMV | ds-DNA | + | 80 | Bovine Mammilitis virus |
| Vaccinia virus | ds-DNA | + | 120 | |
| FMD virus | ss-RNA | − | 25 | Foot & Mouth Disease Virus |
| VSV | ss-RNA | + | 40 × 120 | Vesicular Stomatitis Virus |
| Orf Virus | ds-DNA | + | 70–90 | |
| BEV | ss-RNA | − | 25 | Bovine Enterovirus |
| PEV | ss-RNA | − | 25 | Porcine |

-continued

Some Animal Viruses

| Virus | Genome | Envelope | Approximate Size (mM) | Comment |
|---|---|---|---|---|
| PPV | ss-DNA | − | 20 | Enterovirus Porcine Parvovirus |
| Rabies Virus | ss-RNA | + | 40 × 120 | |
| REO-3 | ds-RNA | − | 60 | |
| BRSV | ss-RNA | + | 80–120 | Bovine Respiratory Syncytial Virus |
| PHV-1 | ds-DNA | + | 120–200 | Porcine Herpes virus-1 |
| Rhinovirus | ss-RNA | − | 25 | |
| Calicivirus | ss-RNA | − | 25 | |
| Rotavirus | ds-RNA | − | 60 | |
| Hog Cholera | ss-RNA | + | 40–60 | |
| Border Dis. | ss-RNA | + | 40–60 | |
| EEE | ss-RNA | + | 60–80 | Eastern Equine Encephalitis Virus |
| WEE | ss-RNA | + | 60–80 | Western Equine Encephalitis Virus |
| VEE | ss-RNA | + | 60–80 | Venezuelan Equine Encephalitis Virus |
| JEE | ss-RNA | + | 60–80 | Japanese Equine Encephalitis Virus |
| Akabane | ss-RNA | − | 60 | |
| BTV | ds-RNA | − | 60 | Blue tongue virus |

Some Human Viruses

| Virus | Genome | Envelope |
|---|---|---|
| HSV-1,2 | ds-DNA | + |
| HAV (Hepatitis A) | ss-RNA | − |
| HBV (Hepatitis B) | ds-DNA | + |
| HCV (Hepatitis C) | ss-RNA | + |
| HEV (Hepatitis E) | ds-DNA | − |
| HIV-1,2 (AIDS) | ss-RNA | + |
| B-19 | ss-DNA | − |
| Adeno viruses | ds-DNA | − |
| Poxviruses (Smallpox, vaccinia) | ds-DNA | + |
| RSV (Respiratory Syntitial) | ss-RNA | + |
| Measles | ss-RNA | + |
| Rubella | ss-RNA | + |
| Influenza A, B | ss-RNA | + |
| Parainfluenza | ss-RNA | + |
| Mumps | ss-RNA | + |
| Rabies | ss-DNA | + |
| HTLV (T-Leuk.) | ss-RNA | + |
| CMV (cytomegalovirus) | ds-DNA | + |
| Poliomielitos | ss-RNA | − |
| Arboviruses | ss-RNA | + |
| Hantaan virus | ss-RNA | + |
| MFV (Marburg fever) | ss-RNA | − |
| Ebola | ss-RNA | + |
| Lassa | ss-RNA | + |
| Calicivirus | ss-RNA | − |
| Coxsackie virus | ss-RNA | − |
| ROTA | ds-RNA | − |
| REO-3 | ds-RNA | − |
| SV-40 | ds-DNA | − |
| Polyomaviruses | ds-DNA | − |
| Papillomavirus | ds-DNA | − |
| Rhinovirus | ss-RNA | − |
| Yellow Fever | ss-RNA | + |
| Dengue | ss-RNA | + |
| Encephalitis viruses | ss-RNA | + |
| Corona virus | ss-RNA | + |
| Varicella-Zoster | ss-DNA | + |
| Epstein-Barr virus | ds-DNA | + |

Examples of bacteria included but are not limited to gram negative and gram positive bacteria, preferably of the genus Staphylococcus, Streptococcus, Corynebacterium, Bacillus, Neisseria, Shigella, Escherichia, Salmonella, Klebsiella, Proteus, Erwinia, Vibrio, Pseudomonas, Brucella, Bordetella, Haemophilus, Yersinia, and particularly *Corynebacterium diphtheriae, Eschericia coli, Streptococcus pyogenes, Staphylococcus aureus*, and *Mycobacteria tuberculosis*. Examples of mycoplasma include but are not limited to *M. bovimastitidis, M. canis, M. hominis, M. hyorhinis, M. urealyticum, M. orale, M. salivarium, M. laidlawi*, and *M. pneumoniae*. Examples of yeast cells include but are not limited to *Saccharomyces cerevisiae, Cryptococcus neoformans, Blastomyces dermatitidis, Histoplasma capsulatum, Paracoccidiodes brasiliensis*, and *Candida albicaus*. Examples of fungi include but are not limited to *Coccidioides immitis, Aspergillus fumigatis, Microsporum audouini, Trichophyton mentagrophytes*, and *Epidermophyton floccosum*. See "*Medical Microbiology and Infectious Diseases*", (A. Samiy, L. Smith, Jr., J. Wyngaarden, eds.), Vol II, W. B. Saunders Co., Philadelphia, Pa.

By "toxins" is meant any biological or chemical compound (including proteins) or combinations thereof that inhibit cell function or cell growth. Thus, the presence of one or more toxins in cell culture results in inhibition of cell growth or function or may kill all or a number of cells in such culture. Examples of toxins include but are not limited to endotoxin, exotoxins, snake venom, cholera toxin, Staphylococcal enterotoxin, leukocidin, Ricin A, poisions derived from animals, neurotoxin, and erythrogenic toxin. See "*Medical Microbiology and Infectious Diseases*", (A. Samiy, L. Smith, Jr., J. Wyngaarden, eds.), Vol II, W. B. Saunders Co., Philadelphia, Pa.

The term "substantially reduced" refers to a reduction in the amount of adventitious agents and/or toxins in a sample (particularly cell culture reagents, nutrient media, media supplements, media subgroups and buffers). Such reduction is preferably a reduction of greater than 50%, more preferably greater than 60%, still more preferably greater than 70%, still more preferably greater than 80%, still more preferably greater than 90% and most preferably greater than 95% compared to the level of adventitious agents and/or toxins in the sample prior to treatment in accordance with the invention. The invention provides at least a one log, preferably at least a two log, more preferably at least a three log, still more preferably at least a four log, still more preferably at least a five log and most preferably at least a six log reduction in the level of toxin and/or adventitious agents in a sample of interest.

The term "contacting" refers to the placing of cells to be cultivated into a culture vessel with the medium in which the cells are to be cultivated. The term "contacting" encompasses mixing cells with medium, pipetting medium onto cells in a culture vessel, and submerging cells in culture medium.

The term "combining" refers to the mixing or admixing of ingredients in a cell culture medium formulation.

A cell culture medium is composed of a number of ingredients and these ingredients vary from one culture medium to another. A "1× formulation" is meant to refer to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See *Methods For Preparation of Media, Supplements and Substrate For Serum-Free Animal Cell Culture* Allen R. Liss, N.Y. (1984), which is incorporated by reference herein in its entirety. The osmolality and/or pH, however, may differ in a 1× formulation compared to the culture medium, particularly when fewer ingredients are contained in the 1× formulation.

A "10× formulation" is meant to refer to a solution wherein each ingredient in that solution is about 10 times more concentrated than the same ingredient in the cell culture medium. For example, a 10× formulation of RPMI-1640 culture medium may contain, among other ingredients, 2.0 g/L L-arginine, 0.5 g/L L-asparagine, and 0.2 g/L L-aspartic acid (compare to 1× formulation, above). A "10× formulation" may contain a number of additional ingredients at a concentration about 10 times that found in the 1× culture medium. As will be readily apparent, "20× formulation," "25× formulation," "50× formulation" and "100× formulation" designate solutions that contain ingredients at about 20-, 25-, 50- or 100-fold concentrations, respectively, as compared to a 1× cell culture medium. Again, the osmolality and pH of the media formulation and concentrated solution may vary. See U.S. Pat. No. 5,474,931, which is directed to culture media concentrate technology.

Overview

The present invention is directed to methods of producing samples (preferably a sample containing biological or animal derived components or ingredients) having reduced or eliminated adventitious agents and/or toxins and more particularly to cell culture nutrients, cell culture reagents, nutritive media, media supplements, media subgroups or buffers having reduced, substantially reduced, inactivated or eliminated adventitious agents or toxins. The invention also relates to pharmaceutical or clinical compositions or solutions produced by these methods.

Nutritive media, media supplements and media subgroups produced by the present methods are any media, media supplement or media subgroup (serum-free or serum-containing) which may be used to manipulate or support the growth of a cell, which may be a bacterial cell, a fungal cell (particularly a yeast cell), a plant cell or an animal cell (particularly an insect cell, a nematode cell or a mammalian cell, most preferably a human cell), any of which may be a somatic cell, a germ cell, a normal cell, a diseased cell, a transformed cell, a mutant cell, a stem cell, a precursor cell or an embryonic cell. Preferred such nutritive media include, but are not limited to, cell culture media, most preferably a bacterial cell culture medium, plant cell culture medium or animal cell culture medium. Preferred media supplements include, but are not limited to, undefined supplements such as extracts or hydrolysates of bacterial, animal or plant cells, glands, tissues or organs (particularly bovine pituitary extract, bovine brain extract and chick embryo extract); and biological fluids or blood derived products (particularly animal sera, and most preferably bovine serum (particularly fetal bovine, newborn calf or normal calf serum), horse serum, porcine serum, rat serum, murine serum, rabbit serum, monkey serum, ape serum or human serum, any of which may be fetal serum) and extracts thereof (more preferably serum albumin and most preferably bovine serum albumin or human serum albumin). Medium supplements may also include defined replacements such as LipoMAX®, OptiMAb®, Knock-Out™ SR (each available from Life Technologies; Inc., Rockville, Md.), and the like, which can be used as substitutes for the undefined media supplements described above. Such supplements may also comprise defined components, including but not limited to, hormones, cytokines, neurotransmitters, lipids, attachment factors, proteins, amino acids and the like.

Nutritive media can also be divided into various subgroups (see for example U.S. Pat. No. 5,474,931) which can be prepared by, and used in accordance with, the methods of the invention. Such subgroups can be combined to produce the nutritive media of the present invention. In another aspect of the invention, individual ingredients (or combinations of ingredients) particuarly ingredients of animal origin may be used in the invention. Such ingredients or samples may then be used in the preparation of any nutritive media, media supplements, media subgroups or buffers.

By the methods of the present invention, any sample, particucarly pharmaceutical or clinical compositions and solutions, cell culture reagents, nutritive media, media supplement, media subgroup or buffer may be produced and stored for an extended period of time without significant loss of biological and biochemical activity. By "without significant loss of biological and biochemical activity" is meant a decrease of less than about 30%, preferably less than about 25%, more preferably less than about 20%, still more preferably less than about 15%, and most preferably less than about 10%, of the biological or biochemical activity of the samples of interest compared to a freshly made sample. Thus, for a pharmaceutical composition, the pharmaceutical composition may be tested for the pharmaceutical property of interest (e.g. drug efficiency) while a media will be tested for cell growth or other parameters well known to those skilled in the art. By an "extended period of time" is meant a period of time longer than that for which the sample (e.g. pharmaceutical composition, nutritive medium, medium supplement, medium subgroup or buffer) is stored when prepared by traditional methods such as ball-milling. As used herein, an "extended period of time" therefore means about 1–36 months, about 2–30 months, about 3–24 months, about 6–24 months, about 9–18 months, or about 4–12 months, under a given storage condition, which may include storage at temperatures of about −70° C. to about 25° C., about −20° C. to about 25° C., about 0° C. to about 25° C., about 4° C. to about 25° C., about 10° C. to about 25° C., or about 20° C. to about 25° C. Assays for determining the biological or biochemical activity of pharmaceutical or clinical compositions, cell culture reagents, nutrients, nutritive media, media supplement, media subgroup or buffers are well-known in the art and are familiar to one of ordinary skill.

Formulation of Pharmaceutical or Clinical Compositions, Cell Culture Reagents, Media, Media Supplements, Media Subgroups and Buffers Any pharmaceutical or clinical composition, cell culture reagent, nutritive media, media supplement, media subgroup or buffer (or any ingredient used or present in such samples) may be prepared by the methods of the present invention. Particularly preferred nutritive media, media supplements and media subgroups that may be prepared according to the invention include cell culture media, media supplements and media subgroups that support the growth of animal cells, plant cells, bacterial cells or yeast cells. Particularly preferred buffers that may be prepared according to the invention include balanced salt solutions which are isotonic for animal cells, plant cells, bacterial cells or yeast cells. Such solutions may be made as a 1× formulation or in concentrated (e.g. in hypertonic concentrations) for example a 10×, 25×, 50×, 100× etc. formulas.

Examples of animal cell culture media that may be prepared according to the present invention include, but are not limited to, DMEM, RPMI-1640, MCDB 131, MCDB 153, MDEM, IMDM, MEM, M199, McCoy's 5A, Williams' Media E, Leibovitz's L-15 Medium, Grace's Insect Medium, IPL-41 Insect Medium, TC-100 Insect Medium, Schneider's Drosophila Medium, Wolf & Quimby's Amphibian Culture Medium, F10 Nutrient Mixture, F12 Nutrient Mixture, and cell-specific serum-free media (SFM) such as those designed to support the culture of keratinocytes, endothelial cells, hepatocytes, melanocytes, CHO cells, 293 cells, PerC6, hybridomas, hematopoetic cells, embryonic cells, neural cells etc. Other media, media supplements and media subgroups suitable for preparation by the invention are available commercially (e.g., from Life Technologies, Inc.; Rockville, Md., and Sigma; St. Louis, Mo.). Formulations for these media, media supplements and media subgroups, as well as many other commonly used animal cell culture media, media supplements and media subgroups are well-known in the art and may be found, for example in the GIBCO/BRL Catalogue and Reference Guide (Life Technologies, Inc.; Rockville, Md.) and in the Sigma Animal Cell Catalogue (Sigma; St. Louis, Mo.).

Examples of plant cell culture media that may be prepared according to the present invention include, but are not limited to, Anderson's Plant Culture Media, CLC Basal Media, Gamborg's Media, Guillard's Marine Plant Culture Media, Provasoli's Marine Media, Kao and Michayluk's Media, Murashige and Skoog Media, McCown's Woody Plant Media, Knudson Orchid Media, Lindemann Orchid Media, and Vacin and Went Media. Formulations for these media, which are commercially available, as well as for many other commonly used plant cell culture media, are well-known in the art and may be found for example in the Sigma Plant Cell Culture Catalogue (Sigma; St. Louis, Mo.).

Examples of bacterial cell culture media that may be prepared according to the present invention include, but are not limited to, Trypticase Soy Media, Brain Heart Infusion Media, Yeast Extract Media, Peptone-Yeast Extract Media, BeefInfusion Media, Thioglycollate Media, Indole-Nitrate Media, MR-VP Media, Simmons° Citrate Media, CTA Media, Bile Esculin Media, Bordet-Gengou Media, Charcoal Yeast Extract (CYE) Media, Mannitol-salt Media, MacConkey's Media, Eosin-methylene blue (EMB) media, Thayer-Martin Media, Salmonella-Shigella Media, and Urease Media. Formulations for these media, which are commercially available, as well as for many other commonly used bacterial cell culture media, are well-known in the art and may be found for example in the DIFCO Manual (DIFCO; Norwood, Mass.) and in the Manual of Clinical Microbiology (American Society for Microbiology, Washington, D.C.).

Examples of fungal cell culture media, particularly yeast cell culture media, that may be prepared according to the present invention include, but are not limited to, Sabouraud Media and Yeast Morphology Media (YMA). Formulations for these media, which are commercially available, as well as for many other commonly used yeast cell culture media, are well-known in the art and may be found for example in the DIFCO Manual (DIFCO; Norwood. Mass.) and in the Manual of Clinical Microbiology (American Society for Microbiology, Washington, D.C.).

As the skilled artisan will appreciate, any of the above media of the invention may also include one or more additional components, such as indicating or selection agents (e.g., dyes, antibiotics, amino acids, enzymes, substrates and the like), filters (e.g., charcoal), salts, polysaccharides, ions, detergents, stabilizers, and the like.

In a particularly preferred embodiment of the invention, the above-described culture media may comprise one or more buffer salts preferably sodium bicarbonate, at concentrations sufficient to provide optimal buffering capacity for the culture medium.

Examples of media supplements that may be prepared by the present methods include, without limitation, animal sera (such as bovine sera (e.g., fetal bovine, newborn calf and calf sera), human sera, equine sera, porcine sera, monkey sera, ape sera, rat sera, murine sera, rabbit sera, ovine sera and the like), defined replacements such as LipoMAX™, OptiMAb™, Knock-Out® SR (each available from Life Technologies, Inc., Rockville, Md.), hormones (including steroid hormones such as corticosteroids, estrogens, androgens (e.g., testosterone) and peptide hormones such as insulin, cytokines (including growth factors (e.g., EGF, aFGF, bFGF, HGF, IGF-1, IGF-2, NGF and the like), interleukins, colony-stimulating factors, interferons and the like), neurotransmitters, lipids (including phospholipids, sphingolipids, fatty acids, Excyte™, cholesterol and the like), attachment factors (including extracellular matrix components such as fibronectin, vitronectin, laminins, collagens, proteoglycans, glycosaminoglycans and the like), and extracts or hydrolysates of animal, plant or bacteria tissues, cells, organs or glands (such as bovine pituitary extract, bovine brain extract, chick embryo extract, bovine embryo extract, chicken meat extract, achilles tendon and extracts thereof) and the like). Other media supplements that may be produced by the present methods include a variety of proteins (such as serum albumins, particularly bovine or human serum albumins; immunoglobulins and fragments or complexes thereof; aprotinin; hemoglobin; haemin or haematin; enzymes (such as trypsin, collagenases, pancreatinin or dispase); lipoproteins; fetuin; ferritin; etc.), which may be natural or recombinant; vitamins; amino acids and variants thereof (including, but not limited to, L-glutamine and cystine), enzyme co-factors; polysaccharides; salts or ions (including trace elements such as salts or ions of molybdenum, vanadium, cobalt, manganese, selenium, and the like); and other supplements and compositions that are useful in cultivating cells in vitro that will be familiar to one of ordinary skill. Preferred media supplements produced by the methods of the invention include animal or mammalian (e.g. human, fish, bovine, porcine, equine, monkey, ape, rat, murine, rabbit, ovine, insect, etc.) derived supplements, ingredients or products. These sera and other media supplements are available commercially (for example, from Life Technologies, Inc., Rockville, Md., and Sigma Cell Culture, St. Louis, Mo.); alternatively, sera and other media supplements described above may be isolated from their natural sources or produced recombinantly by art-known methods that will be routine to one of ordinary skill (see Freshney, R. I., *Culture of Animal Cells*, New York: Alan R. Liss, Inc., pp. 74–78 (1983), and references cited therein; see also Harlow, E., and Lane, D., *Antibodies: A Laboratory Manual*, Cold Spring Harbor, N.Y.: Cold Spring Harbor Laboratory, pp. 116–120 (1988)).

Examples of buffers that may be prepared according to the present invention include, but are not limited to, phosphate-buffered saline (PBS) formulations, Tris-buffered saline (TBS) formulations, HEPES-buffered saline (HBS) formulations, Hanks' Balanced Salt Solutions (HBSS). Dulbecco's PBS (DPBS), Earle's Balanced Salt Solutions, Puck's Saline Solutions, Murashige and Skoog Plant Basal Salt Solutions, Keller's Marine Plant Basal Salt Solutions, Provasoli's Marine Plant Basal Salt Solutions, and Kao and Michayluk's Basal Salt Solutions. Formulations for these buffers, which are commercially available, as well as for many other commonly used buffers, are well-known in the art and may be found for example in the GIBCO/BRL Catalogue and Reference Guide (Life Technologies, Inc.; Rockville, Md.), in the DIFCO Manual (DIFCO; Norwood, Mass.), and in the Sigma Cell Culture Catalogues for animal and plant cell culture (Sigma; St. Louis, Mo.

Examples of pharmaceutical compositions or solutions which may be prepared in accordance with the invention include any composition with pharmaceutical properties such as the ability to treat, alleviate or reduce pain, infection, fever, nervous disorders, circulatory disorders, respiratory disorders, nutritional disorders, metabolical disorders and the like. Such pharmaceutical compositions may comprise one or more drugs, chemicals, proteins, antibodies or fragments thereof, antibiotics, etc., or combinations thereof. Such pharmaceutical compositions may further comprise one or more pharmaceutical carriers including lipids, adjuvants, stabilizers and the like. The invention also relates to clinical solutions, particularly those used for parenteral nutrition, electrolyte balance or intravenous (IV) solutions. Such clinical solutions may be found for example in the Baxter catalog (Deerfield, Ill.) and include but are not limited to Ringer's, Ringer's lactate, 5% Dextrose in water, normal saline (0.9% NaCl), hypotonic saline (0.45% NaCl), 5% Dextrose in saline, and the like. Clinical solutions may further comprise one or more pharmaceutical compositions or components thereof described above.

Preparation of Pharmaceutical and Clinical Compositions, Cell Culture Reagents, Media, Media Supplements, Media Subgroups and Buffers The methods of the present invention provide for the preparation of any sample including those described above. Preferably, such samples are prepared in powdered form. These powdered samples including pharmaceutical and clinical compositions, cell culture reagents, media, supplements, subgroups and buffers are preferably prepared using fluid bed technology (i.e., "agglomeration") and/or via spray-drying, although other techniques may be used to reduce advantitious agents or toxins from such samples. Such other techniques will be recognized by one skilled in the art.

In one aspect of the invention, the samples (e.g. nutritive media, media supplements, media subgroups and buffers) are prepared using fluid bed technology to agglomerate the solutions of media, media supplements, media subgroups or buffers, thereby producing their dry powdered forms. Fluid bed technology is a process of producing agglomerated powders having altered characteristics (particularly, for example, solubility) from the starting materials. In applications of the technology in accordance with the invention, powders are suspended in an upwardly moving column of air, gas or combination of gases. At the same time a controlled and defined amount of liquid is optionally injected into the powder stream to produce a moistened state of the powder; heat or mild heat is optionally then used to dry the material, producing an agglomerated powder. In an aspect of the invention, the liquid injected may contain gas or compounds (biological or chemical) which facilitate reduction, inactivation or elimination of toxins and/or adventitious agents.

Apparatus for producing and/or processing particulate materials by fluid bed technology are available commercially (e.g., from Niro, Inc./Aeromatic-Fielder; Columbia, Md.), and are described, for example, in U.S. Pat. Nos. 3,771,237; 4,885,848; 5,133,137; 5,357,688; and 5,392,531; and in WO 95/13867; the disclosures of all of the foregoing patents and applications are incorporated by reference herein in their entireties. Such apparatuses have been used to prepare agglomerated powders of various materials, including milk whey (U.S. Pat. No. 5,006,204), acidulated meat emulsions (U.S. Pat. No. 4,511,592), proteases (U.S. Pat. No. 4,689,297) and other proteins (DK 167090 B1), and sodium bicarbonate (U.S. Pat. No. 5,325,606).

According to this aspect of the invention, fluid bed technology may be used to prepare bulk agglomerated samples, particuarly nutritive media, media supplements, media subgroups and buffers. In the practice of this aspect of the invention, a dry powdered sample (e.g. nutritive medium, medium supplement, media subgroup, or buffer or mixtures or combinations thereof) is placed into a fluid bed apparatus and is subjected to agglomeration therein. Powdered nutritive media (particularly powdered cell culture media), powdered media supplements (particularly powdered animal sera) and powdered buffers (particularly powdered buffered salines), may be obtained pre-made from commercial sources (e.g., Life Technologies, Inc.; Rockville, Md.). Alternatively, powdered samples including nutritive media, media supplements, media subgroups or buffers may be made by admixing individual components or sets of components according to the formulations described above. Such formulations may include components which topically are not present in powdered nutritive media, media supplement, media subgroup and buffer formulations due to their instability, such as serum, L-glutamine, cystine, insulin, transferrin, lipids (particularly phospholipids, sphingolipids, Excyte™, fatty acids and cholesterol) certain carbohydrates, cytokines (particularly growth factors, interleukins, colony-stimulating factors and interferons), neurotransmitters and buffers (particularly sodium bicarbonate). If L-glutamine is added to the formulation, it may be in the form of a complex with divalent cations such as calcium or magnesium (see U.S. Pat. No. 5,474,931). In another example, two or more powdered components may be admixed and then agglomerated to produce a complex mixture such as media, media supplements, media subgroups or buffers. For example, a powdered nutritive medium may be mixed with a powdered serum (produced, for example, by spray-drying as described below) such as FBS at a serum concentration of about 0.1%, 0.2%, 0.5%, 1%, 2%, 2.5%, 5%, 7.5%, 10%, 15%, 20%, 25%, 50% or higher (w/w as a percentage of the powdered medium); the resulting powdered medium-serum mixture may then be agglomerated to produce an agglomerated medium-serum complex that will readily dissolve in a reconstituting solvent and thus be ready for use without further supplementation.

Once the powdered sample such as nutritive media, media supplement, media subgroup or buffer (or mixture or combinations thereof) is placed into the fluid bed apparatus, it is subjected to suspension in an upwardly moving column of a gas, preferably atmospheric air or an inert gas such as nitrogen, and is passed through one or more particle filters. Alternatively, the gas or combination of gases used may be toxic or inhibitory to adventitious agents or toxins present in the sample. Since most dry powder, non-agglomerated nutritive media, media supplements, media subgroups and buffers are of a relatively small particle size, filters to be used in the invention should be mesh screens that allow air to flow through but that retain the powders, for example filters of about 1–100 mesh, preferably about 2–50 mesh, more preferably about 2.5–35 mesh, still more preferably about 3–20 mesh or about 3.5–15 mesh, and most preferably about 4–6 mesh. Other filters may be used depending on the need and sample used, and can be determined by one skilled in the art.

After placement within the fluid bed chamber, the dry powder sample including nutritive media, media supplement, media subgroup or buffer (or mixtures or combinations thereof) is then optionally treated by injecting, preferably using a spray nozzle on the fluid bed apparatus, a defined and controlled amount of solvent into the powder, to produce a moistened powder. Preferred solvents for use in the present invention are any solvent that is compatible with the sample of interest. In another aspect, the solvent used may be a solvent toxic or inhibitory to adventitious agents or toxins to assist in reducing content of such agents or toxins in the sample. By "compatible" is meant that the solvent does not induce irreversible deleterious changes in the physical or performance characteristics of the sample, such as breakdown or aggregation of the nutrient components of the nutritive medium or changes in the ionic characteristics of the buffer or changes in the pharmaceutical properties of the pharmaceutical composition. Particularly preferred solvents for use in the invention are water (most particularly distilled and/or deionized water), serum (particularly bovine or human serum and most particularly fetal bovine serum or calf serum), organic solvents (particularly dimethylsulfoxide, acetone, ethanol and the like), blood derived products, extracts or hydrolysates of tissues, organs, glands, or cells, animal derived products or any other media supplement or ingredients, buffers, acids or bases (pH adjusting agents), any of which may contain one or more additional components (e.g., salts, polysaccharides, ions, detergents, stabilizers, etc.).

In some aspects of the invention, it may be desirable or advantageous to include in the solvent one or more ingredients that, due to the concentrations of the components required in the final product, cannot be optimally incorporated into the product by other methods such as ball-milling. In one such aspect, the component may be dissolved, suspended, colloided or otherwise introduced into the solvent at the desired concentration, prior to use of the solvent in agglomeration of the powdered sample (e.g. media, media supplement, media subgroup or buffer). Components that may be advantageously incorporated into the solvent in accordance with this aspect of the invention include, but are not limited to, one or more of the above-described sera, hormones, cytokines, neurotransmitters, lipids, carbohydrates, attachment factors, proteins, amino acids, vitamins, enzyme cofactors, animal derived products, blood derived products, extracts or hydrolysates of tissues, organs, glands or cells, polysaccharides, salts, ions, buffers and the like.

The solvent should be introduced into the dry powder in a volume that is dependent upon the mass of powdered sample to be agglomerated. Preferred volumes of solvent per 500 grams of sample (e.g. nutritive media, media supplement, media subgroup or buffer) are about 5–100 ml, more preferably about 10–50 ml, still more preferably about 25–50 ml, and most preferably about 35 ml. Preferred solvent introduction rates per 500 grams of sample (e.g. nutritive media, media supplement, media subgroup or buffer) are a rate of about 1–10 ml/min, preferably about 2–8 ml/min, more preferably about 4–8 ml/min and most preferably about 6 ml/min. In some situations, it may be desirable to cycle between adding solvent for about one minute and then not adding solvent for about one minute (allowing drying of the powder within the apparatus chamber), so as to prevent clumping of the powder during agglomeration.

Once agglomeration of the powder is complete, as evidenced by a larger particle size than that of the original, unagglomerated powder and by the absence of fine dust particles in the agglomerated powder, the powder is substantially dried and preferably thoroughly dried in the apparatus. Preferred apparatus temperatures for drying of the agglomerated powder are about 50–80° C., more preferably about 55–75° C., and most preferably about 60–65° C.; powder is preferably dried in the apparatus for about 3–10 minutes and most preferably for about 5–7 minutes, per 500 grams of powder.

In another aspect of the invention, powdered samples including nutritive media, media supplements, media subgroups and buffers may be prepared by spray-drying. In this aspect of the invention, the sample of interest in its liquid form is placed into a spray-drying apparatus; this liquid is then converted into the corresponding powder by spraying the solution into a chamber in the apparatus under appropriate conditions, such as under controlled temperature and humidity, until a powder is formed. In some situations, it may be desirable or advantageous to spray-dry complex mixtures of two or more of the above-described samples or components or combinations thereof. For example, liquid nutritive media containing animal sera at a desired concentration, or liquid animal sera containing nutritive media components at desired concentrations, may be mixed and then prepared as spray-dried powders according to the methods of the invention.

In a typical spray-drying approach, the liquid sample including nutritive media, media supplements, media subgroups and buffers are aspirated into the apparatus and are atomized into a spray with a rotary- or nozzle-type atomizer. The resulting atomized liquid spray is then mixed with a gas (e.g., nitrogen or more preferably air) and sprayed into a drying chamber under conditions sufficient to promote evaporation and production of a powdered product. In a preferred aspect of the invention, these conditions may comprise electronic control of the temperature and humidity within the chamber such that final drying of the product is promoted. Under these conditions, the solvent in the liquid evaporates in a controlled manner, thereby forming freeflowing particles (i.e., powder) of the sample of interest (e.g. nutritive media, media supplements, media subgroups or buffers). The powder is then discharged from the drying chamber, passed through a cyclone separation system or one or more filters (such as the mesh screens described above for fluid bed preparation) and collected for further processing (e.g., packaging, sterilization, etc.). In some applications, particularly when producing powders from heat-sensitive formulations or samples, the spray-drying apparatus may be combined with a fluid bed apparatus integrated within the drying chamber, which allows the introduction of agglomerating solvents such as those described above into the spray-dried powder to produce agglomerated spray-dried powdered samples. Such combination of processes may facilitate removal or inactivation of toxins or adventitious agents in the sample.

Apparatus for producing particulate materials from liquid materials by spray-drying (with or without integrated fluid bed technology) are available commercially (e.g., from Niro, Inc./Aeromatic-Fielder; Columbia, Md.), and are described, for example, in the "Spray Drying," "Powdered Pharmaceuticals by Spray Drying" and "Fresh Options in Drying" technical brochures of Niro, Inc./Aeromatic-Fielder, the disclosures of which are incorporated by reference herein in their entireties. According to this manufacturer, such apparatuses have been used to prepare powders of various materials, including dairy products, analgesics, antibiotics, vaccines, vitamins, yeasts, vegetable protein, eggs, chemicals, food flavorings and the like. In the present invention, spray-drying has been found to be particularly useful for the preparation of powdered media supplements, such as sera and in particular those sera described above, most particularly human and bovine sera (such as fetal bovine serum and calf serum). It is also particularly suited to prepare powdered pharmaceutical or clinical compositions or solutions.

In the practice of this aspect of the invention, the liquid sample (e.g. nutritive media, media supplements, media subgroups, buffers or pH-adjusting agents) should be sprayed into the chamber through the atomizer at a spray rate of about 25–100 g/min, preferably at a spray rate of about 30–90 g/min, 35–85 g/min, 40–80 g/min, 45–75 g/min, 50–75 g/min, 55–70 g/min. or 60–65 g/min, and more preferably at about 65 g/min. The inlet air temperature in the drying chamber is preferably set at about 100–300° C., more preferably at about 150–250° C., and most preferably at about 200° C., with an outlet temperature of about 50–100° C., more preferably about 60–80° C., and most preferably about 70° C. Air flow in the atomizer is preferably set at about 50–100 kg/hr, more preferably about 75–90 kg/hr, and most preferably about 80.0 kg/hr, at a nozzle pressure of about 1–5 bar, more preferably about 2–3 bar, and most preferably about 2.0 bar. These conditions and settings have been found in the present invention to be preferable for production of a variety of nutritive media, media supplements, media subgroups and buffer powders by spray-drying, particularly for the production of the above-described powdered sera. Following drying, the spray-dried powdered sample (e.g. nutritive media, media supplements, media subgroups or buffers) may be collected in the drying chamber through a cyclone system or one or more filters, preferably such as those described above for fluid bed technology.

Following this preparation, the powders of the invention prepared by the above-described fluid bed and/or spray-drying methods (or combinations thereof) have altered physical characteristics from the starting powders or liquids. For example, non-processed or lyophilized powders often produce significant dust when used, and dissolve poorly or slowly in various solvents, while agglomerated or some spray-dried powders are substantially dust-free and/or dissolve rapidly. Typically, the powdered media, media supplements, media subgroups, buffers, and pharmaceutical or clinical compositions of solutions of the invention will exhibit both reduced dusting and more rapid dissolution than their powdered counterparts prepared by standard techniques such as ball-milling. In some powders which are substantially dust-free but which may not demonstrate enhanced dissolution, the powders may be rapidly dissolved by rapid mechanical solvation of the powder, such as using a mechanical impeller, or by first providing a solvent mist over the powder such as by spray solvation. Moreover, in accordance with the invention, the powdered samples produced have reduced, substantially reduced, or inactivated or eliminated adventitious agents and/or toxins. Such reagents advantageously provide components for manipulating or growing cells which may be used in industrial or biomedical processes and provide pharmaceutical or clinical compositions or solutions important to the medical field.

In another aspect of the invention, the spray-drying and agglomeration approaches described above may be combined to produce agglomerated spray-dried samples (e.g. nutritive media, media supplement, media subgroup and buffer powders). In this aspect, a powdered sample that has been prepared by spray-drying may, after having been spray-dried, then be agglomerated with a solvent (such as those described above) to further improve the performance and physical characteristics of the resultant product (e.g. medium, supplement, subgroup or buffer). For example, an animal serum powder may be prepared by spray-drying liquid animal serum as described above, and this spray-dried serum powder may then be mixed into dry powder nutritive media (prepared by spray-drying or by standard techniques such as ball-milling); this mixed powder may then be agglomerated as described above. Alternatively, a spray-dried nutritive medium, medium supplement, medium subgroup or buffer powder may be agglomerated as above, to improve the dissolution properties of the powder. This approach may be particularly advantageous when spray-drying liquids with low (about 1–10%) solids content, such as liquid animal sera. As one of ordinary skill will appreciate, these approaches will facilitate preparation of a large batch of one or more components (e.g., sera or other media supplements) to be used as a stock for addition to a powdered medium, supplement, subgroup or buffer at a desired concentration, while also obtaining the above-described benefits of agglomeration. In addition, this approach may reduce inter-lot variability which may be a problem with certain media supplements (particularly animal sera) and will facilitate reduction of toxins and/or adventitious agents in accordance with the invention.

The agglomerated and/or spray-dried powdered samples, particularly nutritive media, media supplements, media subgroups, buffers, or pharmaceutical or clinicial compositions or solutions prepared as described above, may then be packaged, for example into containers such as vials, tubes, bottles, bags, pouches, boxes, cartons, drums and the like, prior to or following optimal sterilization as described below. In one such aspect of the invention, the powdered sample including media, media supplements, media subgroups or buffers may be packaged into a compact, vacuum-packed form, such as that known in the art as a "brick-pack" wherein the powder is packaged into a flexible container (such as a bag or a pouch) that is sealed while being evacuated. Other such packages may advantageously comprise one or more access ports (such as valves, luer-lock ports, etc.) allowing the introduction of a solvent (e.g., water, sera, media or other aqueous or organic solvents or solutions) directly into the package to facilitate rapid dissolution of the powder. In a related aspect, the package may comprise two or more adjacent compartments, one or more of which may contain one or more of the dry powder samples (e.g. media, media supplements, media subgroups or buffers) of the invention and one or more other of which may contain one or more aqueous or organic solvents which may be sterile. In this aspect, the dry powder may then be dissolved by simply removing or breaking the barrier between the compartments, ideally without loss of sterility, to allow admixture of the powder and the solvent such that the powder dissolves and produces a sterile sample such as nutritive medium, medium supplement, medium subgroup or buffer at a desired concentration.

Packaged samples including media, media supplements, media subgroups and buffers of the invention are preferably stored for the extended times, and at the temperatures, noted above, typically for about 1–24 months at temperatures of less than about 30° C., more preferably at temperatures of less than about 20–25° C., until use. Unlike traditional powdered media, media supplements, media subgroups or buffers, storage at reduced temperatures (e.g. 0–4° C.) may not be necessary for the maintenance of performance characteristics of the media, media supplements, media subgroups and buffers prepared by the present methods. Of course, other storage temperatures may be required for those aspects of the invention where the packages also comprise separate compartments containing one or more solvents; in these cases, the optimal storage conditions will be dictated by the storage requirements of the solvent(s) which will be known to the skilled artisan.

Sterilization and Packaging

The invention also provides additional methods for sterilizing or substantially sterilizing the samples including nutritive media, media supplements, media subgroups and buffers of the invention. Such additional methods may include filtration, heat sterilization, irradiation or other chemical or physical methods. Preferably, nutritive media, media supplements, media subgroups or buffers (preferably powders prepared as described above by spray-drying and/or by agglomeration) may be irradiated under conditions favoring sterilization. Preferably, this irradiation is accomplished in bulk (i.e., following packaging of the sample), and most preferably this irradiation is accomplished by exposure of the bulk packaged sample (e.g. media, media supplement, media subgroup or buffer) of the invention to a source of gamma rays under conditions such that bacteria, fungi, spores or viruses that may be resident in the powdered sample are inactivated (i.e., prevented from replicating). Alternatively, irradiation may be accomplished by exposure of the sample (e.g. media, media supplement, media subgroup or buffer), prior to packaging, to a source of gamma rays or a source of ultraviolet light. The sample (e.g. media, media supplements, media subgroups and buffers) of the invention may alternatively be sterilized by heat treatment (if the subgroups or components of the sample such as nutritive media, media supplement, media subgroup or buffer are heat stable), for example by flash pasteurization or autoclaving. As will be understood by one of ordinary skill in the art, the dose of irradiation or heat, and the time of exposure, required for sterilization depend upon the bulk of the materials to be sterilized.

In a particularly preferred aspect of the invention, the bulk sample (e.g. nutritive media, media supplements, media subgroups or buffers) (which are preferably in powdered form) are exposed to a source of γ irradiation at a total dosage of about 10–100 kilograys (kGy), preferably a total dosage of about 15–75 kGy, 15–50 kGy, 15–40 kGy, 20–40 kGy or 25–45 kGy, more preferably a total dosage of about 20–30 kGy, and most preferably a total dosage of about 25–35 kGy, for about 1 hour to about 7 days, more preferably about 1 hour to about 5 days, 1 hour to about 3 days, about 1–24 hours or about 1–5 hours, and most preferably about 1–3 hours ("normal dose rate"). Alternatively, the bulk sample may be sterilized at a "slow dose rate" of a total cumulative dosage of about 25–100 kGy over a period of about 1–5 days. During irradiation, the sample including nutritive media, media supplements, media subgroups or buffers (which are preferably in powdered form) are preferably stored at a temperature of about −70° C. to about room temperature (about 20–25° C.), most preferably at about −70° C. One of ordinary skill will appreciate, of course, that radiation dose and exposure times may be adjusted depending upon the bulk and/or mass of material to be irradiated; typical optimal irradiation dosages, exposure times and storage temperatures required for sterilization of bulk powdered materials by irradiation or heat treatment are well-known in the art.

Following sterilization, unpackaged samples including nutritive media, media supplements, media subgroups and buffers may be packaged under aseptic conditions, for example by packaging the sample into containers such as sterile tubes, vials, bottles, bags, pouches, boxes, cartons, drums and the like, or in the vacuum packaging or integrated powder/solvent packaging described above. Sterile packaged samples such as media, media supplements, media subgroups and buffers may then be stored for extended periods of time as described above.

Use of the Pharmaceutical and Clinical Compositions, Nutritive Media, Media Supplements, Media Subgroups and Buffers The present invention thus provides samples including pharmaceutical and clinical compositions/solutions, nutritive media, media supplements, media subgroups and buffers (which are preferably powdered) that have reduced, substantially reduced, inactivated or eliminated adventitious agents and/or toxins. In powdered form, such samples are readily soluble in a rehydrating solvent and are substantially dust free. For use, samples produced by the may be hydrated (or "reconstituted") in a volume of a solvent sufficient to produce the desired concentration, nutrient, electrolyte, ionic and pH conditions required for the particular use of the solvated sample (e.g. media, media supplement, media subgroup or buffer). This reconstitution is particularly facilitated in the present invention, since the powdered sample will rapidly go into solution and will produce little if any dust or insoluble material, unlike lyophilized or ball-milled samples such as nutritive media, media supplements, media subgroups or buffers.

Preferred solvents for use in reconstituting the powdered sample of the invention include the solvents described above such as water (most particularly distilled and/or deionized water), serum (particularly bovine or human serum and most particularly fetal bovine serum or calf serum), organic solvents (particularly dimethylsulfoxide, acetone, ethanol and the like), or any combination thereof, any of which may contain one or more additional components (e.g., salts, polysaccharides, ions, detergents, stabilizers, etc.). For example, powdered media supplements (such as animal sera) and buffers are preferably reconstituted in water to a 1× final concentration, or optionally to a higher concentration (e.g., 2×, 2.5×, 5×, 10, 20×, 25×, 50×, 100×, 500×, 1000× etc.) for the preparation of stock solutions or for storage. Alternatively, powdered culture media may be reconstituted in a solution of media supplements (e.g., sera such as FBS) in water, such as those solutions wherein the media supplement is present at a concentration, for example, of 0.5%, 1%, 2%, 2.5%, 5%, 7.5%, 10%, 15%, 20%, 25%, 50%, or higher, vol/vol in the water.

Reconstitution of the powdered sample (e.g. nutritive media, media supplements, media subgroups or buffers) is preferably accomplished under aseptic conditions to maintain the sterility of the reconstituted sample, although the reconstituted sample may be further sterilized, preferably by filtration or other sterilization methods that are well-known in the art, following rehydration. Following their reconstitution, media, media supplements, media subgroups and buffers or other samples should be stored at temperatures below about 10° C., preferably at temperatures of about 0–4° C., until use.

The reconstituted nutritive media, media supplements, media subgroups and buffers may be used to culture or manipulate cells according to standard cell culture techniques which are well-known to one of ordinary skill in the art. In such techniques, the cells to be cultured are contacted with the reconstituted media, media supplement, media subgroup or buffer of the invention under conditions favoring the cultivation or manipulation of the cells (such as controlled temperature, humidity, lighting and atmospheric conditions). Cells which are particularly amenable to cultivation by such methods include, but are not limited to, bacterial cells, fish cells, yeast cells, plant cells and animal cells. Such bacterial cells, yeast cells, plant cells and animal cells are available commercially from known culture depositories, e.g., American Type Culture Collection (Rockville, Md.), Invitrogen (La Jolla, Calif.) and others that will be familiar to one of ordinary skill in the art. Preferred animal cells for cultivation by these methods include, but are not limited to, insect cells (most preferably Drosophila cells, Spodoptera cells and Trichoplusa cells), nematode cells (most preferably *C. elegans* cells) and mammalian cells (including but not limited to CHO cells, COS cells, VERO cells, BHK cells, AE-1 cells, SP2/0 cells, L5.1 cells, hybridoma cells and most preferably human cells such as 293 cells, PerC 6 cells and HeLa cells), any of which may be a somatic cell, a germ cell, a normal cell, a diseased cell, a transformed cell, a mutant cell, a stem cell, a precursor cell or an embryonic cell, and any of which may be an anchorage-dependent or anchorage-independent (i.e., "suspension") cell.

Cells

In another aspect, the invention relates to methods for producing dry cell powder compositions comprising one or more cells, and to dry cell powders produced by these methods. Thus, the invention relates to reducing adventitious agents or toxins from a sample containing one or more cells by the methods of the invention. These methods thus produce cell-containing compositions wherein the cells are preserved and may be stored for extended periods of time until use and such cell compositions have reduced or eliminated adventitious agents or toxins. In this way, the methods of the invention overcome some of the drawbacks of traditional methods of cell preservation (e.g., freezing) such as the need for cyropreservation equipment and the use of certain cryopreservatives that may be toxic to the cells.

Methods according to this aspect of the invention may comprise one or more steps. For example, one such method may comprise obtaining one or more cells of interest, forming an aqueous cell suspension by suspending the one or more cells in an aqueous solution, and treating the cells in accordance with the invention under sufficient conditions to reduce or substantially reduce adventitious agents or toxins (without substantially affecting the viability of such cells), preferably by substantially drying the cell suspension under conditions favoring the production of a dried powder (preferably by spray-drying). These methods may further comprise contacting the one or more cells with one or more stabilizing or preserving compounds (e.g., a polysaccharide, including but not limited to trehalose). The aqueous solution used to form the cell suspension preferably comprises one or more components, such as one or more of the above-described nutritive media, media supplements, media subgroups, salts or buffers. Preferably, the aqueous solution used to form the cell suspension is adjusted to optimal or substantially optimal tonicity and osmolality for the cell type being dried. The aqueous solution may optionally comprise one or more additional components, such as one or more polysaccharides, ions, detergents, stabilizing or preserving compounds (including trehalose), and the like. In aspects of the invention wherein the one or more cells are contacted with one or more stabilizing or preserving compounds, the stabilizing or preserving compounds may be incorporated into the aqueous solution used to form the aqueous cell suspension. Alternatively, the stabilizing or preserving compounds may be sprayed or agglomerated onto the dry cell powder after formation of the powder.

Once the dry cell powder has been formed by the above-described methods, the powder may optionally be agglomerated with a solvent according to methods described above for agglomeration of dry powders. Any solvent that is compatible with the cell type being dried may be used to agglomerate the dry cell powder, including but not limited to water, a nutritive medium solution, a nutritive medium supplement solution (including sera, particularly bovine sera (most particularly fetal bovine and calf sera) and human sera), a buffer solution, a salt solution, and combinations thereof. In another aspect, the cell powder of the invention may be mixed with one or more powdered media, media supplements, media subgroups or buffers (which are produced by the methods of the invention or by standard techniques) and such mixtures may optimally be agglomerated with a solvent by the methods of the invention.

A variety of cells may be dried according to the methods of the invention, including prokaryotic (e.g., bacterial) and eukaryotic (e.g. fungal (especially yeast), animal (especially mammalian, including human) and plant) cells, particularly those cells, tissues, organs, organ systems, and organisms described above. Once the dried cells have been produced, they may be packaged aseptically and stored for extended periods of time (e.g., several months to several years), preferably at temperatures of about 0–30° C., 4–25° C., 10–25° C., or 20–25° C. (i.e., "room temperature") until use. For use in preparing cultures of viable cells, the dry cell powder may be aseptically reconstituted, into a cell suspension comprising one or more viable cells, with an aqueous solvent (e.g., sterile water, buffer solutions, media supplements, culture media, or combinations thereof) and cultured according to standard art-known protocols. Alternatively, the dry cell powder may be reconstituted into a cell suspension where cell viability is not essential, for example for preparation of an immunogen to be used for immunization of an animal. In such cases, the dry cell powder may be reconstituted with any solvent that is compatible with standard immunization protocols, such as aqueous or organic solvents that may comprise one or more detergents, adjuvants, etc.

Kits

The pharmaceutical or clinical compositions, cell culture reagents, media, media supplements, media subgroups, buffers and cells provided by the invention are ideally suited for preparation of kits. Such a kit may comprise one or more containers such as vials, test tubes, bottles, packages, pouches, drums, and the like. Each of the containers may contain one or more of the above-described pharmaceutical or clinical compositions, cell culture reagents, nutritive media, media supplements, media subgroups, buffers or cells of the invention, or combinations thereof. Such pharmaceutical or clinical compositions, cell culture reagents, nutritive media, media supplements, media subgroups, buffers or cells may be hydrated or dehydrated but are typically dehydrated preparations produced by the methods of the invention. Such preparations may, according to the invention, be sterile or substantially sterile.

A first container may contain, for example, a nutritive media, media supplement, media subgroup or a buffer of the invention, or any component or subgroup thereof, such as any of those nutritive media, media supplements, media subgroups or buffers of the invention that are described above. Additional nutritive media, buffers, extracts, supplements, components or subgroups may be contained in additional containers in the present kits. The kits may also contain, in one or more additional containers, one or more cells such as the above-described bacterial cells, yeast cells, plant cells or animal cells. Such cells may be lyophilized, dried, frozen or otherwise preserved, or may be treated by the methods of the invention (e.g. spray-dried). In addition, the kits of the invention may further comprise one or more additional containers, containing, for example, L-glutamine, optionally complexed with one or more divalent cations (see U.S. Pat. No. 5,474,931). The kits may further comprise one or more additional containers containing a solvent to be used in reconstituting the dry powder pharmaceutical or clinical compositions, cell culture reagents, nutritive media, media supplements, media subgroups and/or buffers; such solvents may be aqueous (including buffer solutions, saline solutions, nutritive medium solutions, nutritive medium supplement solutions (including sera such as bovine sera (particularly fetal bovine sera or calf sera) or human sera), or combinations thereof) or organic. Other ingredients that are not compatible for admixture with the nutritive media, buffers, pharmaceutical compositions, extracts, supplements, components, subgroups etc. of the invention may be contained in one or more additional containers to avoid mixing of incompatible components. Such kits may also comprise transfection reagents (such as lipids or cationic lipids).

The number and types of containers contained in a given kit may vary depending on the desired product or the type of pharamaceutical or clinical compositions, media, media supplement, media subgroup or buffer to be prepared. Typically, the kit will contain the respective containers containing the components or supplements necessary to make a particular pharmaceutical or clinical compositions, media, media supplement, media subgroup or buffer. However, additional containers may be included in the kit of the invention so that different pharmaceutical or clinical compositions, media, media supplements, media subgroups or buffers can be prepared by mixing different amounts of various components, supplements, subgroups, buffers, solvents, etc., to make different pharmaceutical or clinical compositions, media, media supplement, media subgroup or buffer formulations.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Agglomeration of Typical Dry Powder Media (DPM)

1. With a bench top laboratory fluid bed apparatus (Strea-1; Niro, Inc./Aeromatic-Fielder; Columbia, Md.): Place 100–500 g of DPM within the chamber. Place onto apparatus and use the lever to seal the unit.

2. Start the airflow to fluidize (levitate) the DPM. Since traditional DPM is of relatively fine particle size, setting 4–6 will be needed. Turn on the vacuum device to catch fine DPM particles, passing through the upper filters. Make sure that the fluidized powder is approximately central within the chamber with respect to the lower mesh screen and the upper filters.

3. Start the injection device (spray unit) by first plugging in the compressed air line and then by starting the pump which is connected to a water source. The goal is to admit ~6 ml of water per minute (the flow rate for any given pump based upon RPM and tubing diameter must be known). In order to prevent clumping of DPM, alternatively add water for ~1 minute and then stop for ~1 minute, allowing drying to occur in the chamber.

4. If filters become coated with DPM during the run so that blowback does not dislodge powder, turn fan speed down to setting 2–3 until all filters have been blown clear. Then increase running fan speed to previous level.

5. Agglomeration will be complete when ~35 ml of water has been added for each 500 g of DPM. This volume will vary depending upon the DPM formulation. A downward flow of relatively large agglomerated granules will be seen in the chamber (bottom) toward the end of the run. Visibly larger particles and absence of fine dust indicates that the process is complete.

6. Allow agglomerated DPM to dry thoroughly for 5–7 minutes.

7. At end of run, blow off filters 4 times.

8. Turn unit off, disconnect water tube and collect agglomerated DPM into an airtight container.

These approaches should be adjusted when using a process-scale or production-scale fluid bed apparatus. For example, when the MP-1 (Niro, Inc./Aeromatic-Fielder; Columbia, Md.) apparatus is used, the following protocol has yielded satisfactory results:

1. Seal unit (inflate gaskets).
2. Start fan for pre-heat.
3. Stop fan when inlet air temperature equals set point.
4. Deflate gaskets, load material, inflate gaskets.

Steps 5–8 should all be accomplished within one minute:

5. Start batch.
6. Start fan, and turn on filter cleaning.
7. Set nozzle atomizing air pressure % output (check nozzle for vacuum).
8. Connect liquid feed line.
9. Start pump on screen and at pump.

10. Reset batch time.
11. Spray all liquid at set rate (26 g/min). Use ~250 ml water for 2 kg powder.
12. Stop pump at pump and on screen when all liquid is added.
13. Reduce airflow to drying value (for example from 100 to 60).
14. When product reaches desired temperature (40° C.), go to "initial set up" screen and set "batch duration" for a value of 2–3 minutes greater than the present "batch time".
15. Stop batch.
16. Deflate gaskets.

Typical instrument settings (for bench-, process- and production-scale apparatuses):

Drying temperature: 60–65° C.

Outlet air temperature: ~33° C.

Blow out pressure: 5 bar

Atomizing pressure: 1.5–2.0 bar

Airflow 60–120 CMH

Blow back dwell: 1 after spraying, 2 while spraying

Capacity of fan: 5 at start of run, 6 after agglomeration is evident

Magnahelics: Filter resistance 150–250, Resistance of perforated control plate ~50, Air volume: less than 50.

EXAMPLE 2

Addition of Sodium Bicarbonate as an Integral Part of DPM

Sodium bicarbonate is not typically added to DPM during manufacturing by ball-milling or lyophilization, due to potential off-gassing and buffering capacity complications encountered upon storage of the powdered media. This standard production process thus necessitates the addition of sodium bicarbonate, and pH adjustment, upon reconstitution of the media. With the present methods, however, these additional steps may be obviated by adding the sodium bicarbonate (or any buffering salt) directly to the powdered medium during manufacturing.

There are two ways of including sodium bicarbonate (or any buffering salt) within the DPM: (a) via the injection device and (b) as part of the DPM.

(a) Injection Device

Because of the solubility of sodium bicarbonate and the amounts that generally need to be added to a typical mammalian cell culture medium, fairly large volumes of liquid would need to be injected into the powder (significantly greater than the 35 ml of water mentioned above). This is still possible and in fact may be preferable if adding another component that similarly requires a relatively large volume of liquid in order to be added to the DPM, as is the case with serum for example. In this case, care must be taken to sequentially add liquid, let dry etc. a number of times to insure that the DPM does not become clumped within the device. Using the 6 ml per minute for ~1 minute and then allowing drying for another 2 minutes is about right.

The amount of liquid to add is determined as follows: Prepare sodium bicarbonate at 75 g/L in water. Example: 250 g of DPM in the chamber to be agglomerated. Assume 10.0 g of DPM is required for 1 L of 1x liquid medium.

Therefore, 250 g represents 25 L of 1x liquid medium. For each L of liquid, assume (for example) a requirement of 2 g of sodium bicarbonate. This means that 50 g of bicarbonate is needed. Now, since the bicarbonate solution is at 75 g/L, then 0.67 L of bicarbonate solution must be added to the 250 g of DPM.

The sodium bicarbonate solution would be added similarly to the process for "agglomeration of a typical DPM" above except that a longer drying time between cycles is needed since the pH of the sodium bicarbonate solution is ~8.00 which can degrade media components. It is important that the powder never become "soaked" by addition of bicarbonate solution too rapidly without allowing sufficient time for thorough drying of the bicarbonate powder between cycles. Also, longer fluid drying times are required since it is important to have as low a final moisture content as possible since moisture would result in liberation of carbon dioxide gas resulting in loss of buffering capacity and "pillow" formation if powder is in a foil packet.

(b) As Part of the DPM

Sodium bicarbonate can be milled into the DPM in a similar fashion as for other media components prior to fluid bed treatment. However, in the milling process, the bicarbonate should be added as the final component. All of the other media components should be milled as usual and then the mill stopped and the bicarbonate added last, with further milling to reach proper sized particles. It is important that all post-milling processing (placement into containers, etc.) be done in a humidity-controlled environment set as low as operationally possible (~20–40%. Fluid bed processing should then be performed as soon as possible after milling. (If not processed the same day, DPM must be double wrapped and placed within a sealed container with moisture absorbents.)

The fluid bed process itself is done similarly to the example given above (with use of 35 ml per 500 g of DPM) except that drying times after water injection (~6 ml/min) should again be extended: 1 min of injection of water and 2 minutes drying cycles. It will be noted that the color of the DPM will be deep red-light purple due to presence of phenol red but can be light orange. Since the DPM has essentially no moisture content, this does not represent a degradative situation, and is why fluid bed processing is essential.

EXAMPLE 3

DPM that Includes Buffering Salts (e.g., Sodium Bicarbonate) and is Formulated so that pH of Reconstituted (1x) Medium is Automatically of Desired pH with No User Efforts As noted above, all commercially available mammalian cell culture powdered media require addition of one or more buffer salts (e.g., sodium bicarbonate) when preparing 1x liquid, and then adjustment of pH, so that the solution will be at proper pH. The present methods, however, can be used to obviate both the addition of sodium bicarbonate (as described above in Example 2) and the need for pH adjustment. In this aspect of the invention, fluid bed technology is used to introduce acid or base (depending on the need) to a dry powder medium comprising one or more buffering salts. In accordance with this aspect of the invention, any buffering salts or combinations thereof, and any acid or base, may be used depending upon the desired pH and buffering capacity in the ultimately reconstituted cell culture medium.

If sodium bicarbonate is added directly to the DPM as a powder, it is possible for the end user to simply add water and mix to yield a solution already containing bicarbonate (see above) and of proper pH. It is necessary first to determine how much of a pH adjustment is required. (1) Place 1 L of water in a beaker. Add DPM to the liquid and mix. (Amount to add/L is given by the specifications for that powder, e.g., 10 g/L, 13 g/L). In this case, the weight of the sodium bicarbonate must also be considered in determining how much to add per liter. (2) After the powder has dissolved, add 5N HCl to adjust the solution to the desired pH. Record the amount. (3) Convert this number to amount of 1N HCl. Calculate how much 1N HCl is needed for adjustment of the total powder to be agglomerated. (Example: 5 ml of 1N HCl is needed to adjust 1 L of 1× medium A to pH 7.2 from the unadjusted pH of 7.9. That 1 L of 1× medium represents, for example, 13.0 g of DPM. Therefore, for each 13.0 g of DPM, 5 ml of 1N HCl is needed. If we want to adjust pH of 250 g of DPM, then 250 divided by 13.0=19.2×5 ml or 96 ml of 1N HCl is needed to be added to the powder to make it automatically pH-adjusted.

This 1N HCl must now be added to the DPM. The best way for that is to use the injection device, adding 1N HCl instead of water. In general, the protocol is similar to the above with the following exceptions: (1) the 1N HCl must be added slowly to the media which contains sodium bicarbonate. If it is added too quickly, carbon dioxide may be driven off, resulting in suboptimal buffering capacity. Because of the volume of 1N HCl generally required, several 1 minute on, 2 minute off cycles are needed. A dry powder state must be obtained at the end of each cycle so that a dynamic system exists where DPM has characteristics of a fluid process but in reality is a dried powder. (Amazingly, as HCl is added to the powder, the bulk color changes from dark reddish purple to light yellow-orange color even though the powder remains essentially dry at all times due to the continual evaporation within the system). Since the total amount of HCl has been calculated to yield an essentially neutral pH, the powder is never really exposed to "acid" conditions as long as the fluid bed is properly adjusted (see above; position of the powder particles within the chamber during operation). It is important to make sure that all of the powder is moving through the system (i.e., being lifted, agglomerated and settled continuously) and having no "dead" zones within the chamber.

Once the powder is collected after the run, it can be added to water and reconstituted at any time as long as it has been kept in proper "dry" packaging and location. No adjustment of pH is needed. Thus, the invention provides an automatic pH-adjusting dry powdered medium, where the pH of the liquid medium made by reconstituting the dry powdered medium requires no adjustment of pH.

EXAMPLE 4

Inclusion of Large Molecular Weight Supplements Such as Serum, Albumin, Hy-Soy, etc., within the DPM Itself Heretofore, dried powder media containing serum have not been commercially available. Using the present methods (via fluid bed and spray-drying technologies), we have succeeded in adding serum to a powder in a manner where functionality (cell culture) is maintained.

The injection device of the fluid bed apparatus is able to form a mist with serum, and concentrated albumin. We attempted to see if serum added to the DPM and dried in this manner would be functional.

Procedure for addition of serum: (1) Determine the weight of standard DPM to be agglomerated. (2) From this, based upon the g/L for the particular powder, calculate the volume of 1× medium that the g of powder will make. (3) Calculate the volume of serum that would be needed at a given percentage level of supplementation (e.g., 100 g of powder to be used in 10 g/L yields 10 L-equivalents of powder). At 5% serum supplementation, 500 ml of serum would be required to be added by the injection device.

Protocol for addition of the serum: Serum and albumin are very viscous. The nozzle spray pattern must be checked for droplet size and pattern. With the sample tube in the solution to be added to the powder, test spray against a cardboard or other backdrop. Check for uniformity and small droplet size. If not a "mist," increase atomizing pressure by 0.5 bar and test again. Do this until sufficient pressure results in a fine mist pattern.

For use in cell culture applications, it is necessary to know the weight/ml of serum-DPM to be used per L of 1× medium. To do this, accurately weigh vials or test tubes that will hold the serum during drying. Place a constant (known) quantity of serum into each of the vials. Then place vials into a Speed Vac or lyophilizer. Remove water until dryness. Then weigh the vials again, this time containing lyophilized serum. Calculate the weight of serum and express as per ml of original volume. The weight of agglomerated DPM with serum to use per L will then be the standard DPM "use" weight plus the weight of the serum at a given level.

For example, assume that Medium A (DPM) is to be used at 10 g/l. Serum supplementation is to be at 5% v/v. This means that in addition to the weight of the standard DPM, the weight of the serum would equal 5%=50 ml to add per L of medium. Assume that serum powder weighs 0.06 g/ml. Then the weight of the powdered serum=50×0.06 g/L=3 g. Therefore, the weight of serum-containing DPM that would be added to 1 L of water is the weight of serum powder (3 g) plus the weight of the standard DPM (10 g) per liter=13 g/L.

EXAMPLE 5

Reducing or Eliminating Milling Techniques (High Energy Input System That Break Components Down to Micron-Sized Particles) When Manufacturing a DPM As noted above, dry powdered medium typically is manufactured via the milling process, which is laborious and has a number of problems. The methods of the present invention provide for the production of a dry powdered medium using fluid bed technology, which overcomes these labor and technical constraints.

A. Blending First in External Device, Then Fluid Bed Treatment

Normally milled DPM is blended with sodium bicarbonate (directly as received from the supplier, additional ball milling not needed). [RPMI 1640 with sodium bicarbonate at 2 g/L-equivalents]. This mixture is blended for 20 minutes. The powder is then placed within the fluid bed chamber and fluidized as above for bicarbonate-containing media or bicarbonate-containing media with automatic pH control.

B. Blending Directly in Fluid Bed Chamber, Then Agglomeration

Sodium bicarbonate is placed into the chamber directly with the milled DPM and blended (mixed) for a brief period of time, to be followed with agglomeration. This eliminates blending in a separate unit.

C. Total Elimination of the Ball-Milling Process

Either all of the DPM chemicals are added directly to the fluid bed chamber and mixed preliminarily followed by agglomeration or, more likely, some of the coarser, "stickier", etc. chemicals are given a brief grinding treatment in a rotary grinder and then placed within the fluid bed for blending and final agglomeration.

EXAMPLE 6

A Method for Having All of the Above Characteristics Within This Same DPM

We have combined addition of "off the shelf" sodium bicarbonate with milled DPM and automatic pH control. We have also combined serum with DPM.

To combine serum with DPM containing sodium bicarbonate with automatic pH control, one protocol is to:

1. Add sodium bicarbonate (powder, from supplier) to DPM (milled or ground).
2. Blend ingredients (mix, either external unit or fluid bed).
3. In a separate vessel, reconstitute 1 L of the DPM (containing bicarbonate) with water (1×) and determine the amount of 1N HCl, or 1N NaOH that is required to adjust the pH of the solution to 7.5. On a liter basis, knowing the mass of powder to be agglomerated (and thus the L-equivalents), calculate the amount of 1N HCl or 1N NaOH for the total powder to be agglomerated at the above-calculated amount. Add this amount via fluid bed device (injection nozzle). (Although DPM is not "liquid," it is important to have a powder as close to neutrality as possible but not of such an acid pH that bicarbonate would be liberated when adding serum, since moisture is involved in the process. At pH 7.6 or higher, a concentrated solution of sodium bicarbonate will not evolve $CO_2$ gas, but at lower pH gas will be given off.)
4. Addition of serum (extended agglomeration), based upon percentage supplementation and g to be agglomerated.
5. Using the same 1 L of 1× liquid from (3) above, determine the amount of 1N HCl or 1N NaOH needed to adjust the pH to the desired pH (e.g., 7.2). Using this information, calculate the amount to be used for the weight of powder that has been agglomerated with serum (knowing g/L specifications). Add this amount via fluid device (injection nozzle).
6. Gamma irradiation is used to sterilize the powdered media.

In a similar method, a serum-containing DPM may be produced by combining a particular amount of DPM with a particular amount of powdered serum (prepared, e.g., by spray-drying as described in Example 8 below) and then agglomerating the mixture. For example, for preparation of medium containing 10% powdered FBS, 55.5 g powdered FBS may be added to 500 g of powdered culture medium and the powders mixed well by agitation. This mixture may then be water-agglomerated as described above, and will yield, upon reconstitution, a culture medium containing 10% FBS which may be auto-pH-adjusting.

EXAMPLE 7

Production of 100% Serum Powder by Fluid Bed Processing (To Simulate Spray-Drying)

Methodology
1) We used the benchtop laboratory fluid bed apparatus (Strea-1). For production of powdered serum, nothing is placed within the chamber. The lever is used to seal the unit.
2) Serum was added by way of the injection device (spray unit). As the serum was added into the chamber, the air flow was increased enough and the flow of serum slowed enough that evaporation of water occurred and the serum was dried sufficiently so that powder formed instantly within the chamber. No moist or fluid coating existed anywhere within the chamber.
3) Pump speed was set to allow for ~1 ml/minute into the chamber.
4) Airflow speed was set to a setting of ~8–9.
5) To clean filters intermittently, fan speed was reduced to ~2–3. This was done routinely every 5–10 minutes. (The 8–9 airflow setting is so high that the filters will not blow off the powder and clean themselves).
6) After one round of filter blow-off, fan speed was increased to previous levels and the pump turned on. (Once these parameters were set, the pump was run continuously except when cleaning the filters as indicated).
7) After all of the serum liquid had been added into the agglomerator, final drying was performed over five minutes.
8) The filters were then blown off to collect as much powder as possible, and the machine shut off and product removed. Powdered serum was placed into an air-tight container and protected from light.

Typical Instrument Settings
Drying temperature: 60–65° C.
Outlet air temperature: ~33° C.
Blow out pressure: 5 bar
Atomizing pressure: 2.0–2.5 bar
Blow back dwell: 2, in between spraying
Capacity of fan: 8–9 throughout run
Magnahelics: Filter resistance—150–250, Resistance of perforated control plate—~50, Air volume—less than 50.

Figure 1A:
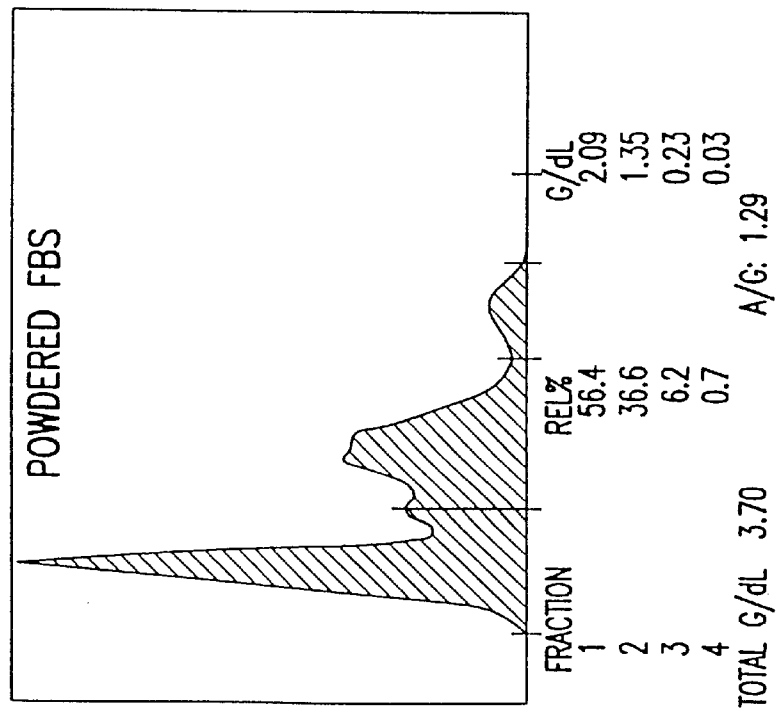

To determine if agglomeration of the FBS affected the protein structure or distribution, samples of agglomerated FBS and liquid FBS were run on SDS-PAGE, stained for protein and scanned densitometrically. As shown in FIG. 1, agglomerated FBS prepared according to the present methods (FIG. 1A) demonstrated a nearly identical protein profile to that observed with liquid FBS (FIG. 1B). These results indicate that the controlled production of dry powdered FBS by the present methods does not substantially affect the structure or distribution of the major components of the serum.

Figure 2A:
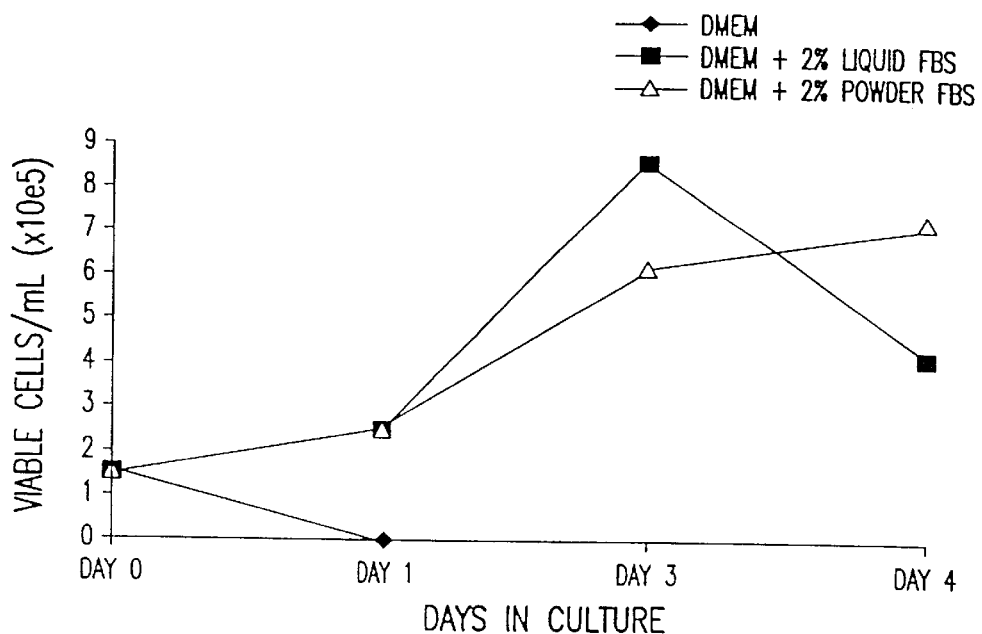
FIG. 2 is a composite of line graphs of growth (FIG. 2A) and passage success (FIG. 2B) of SP2/0 cells in Dulbecco's Modified Eagle's Medium (DMEM) supplemented with 2% (w/v) FBS prepared in powdered form by the agglomeration methods of the invention.
Figure 2B:
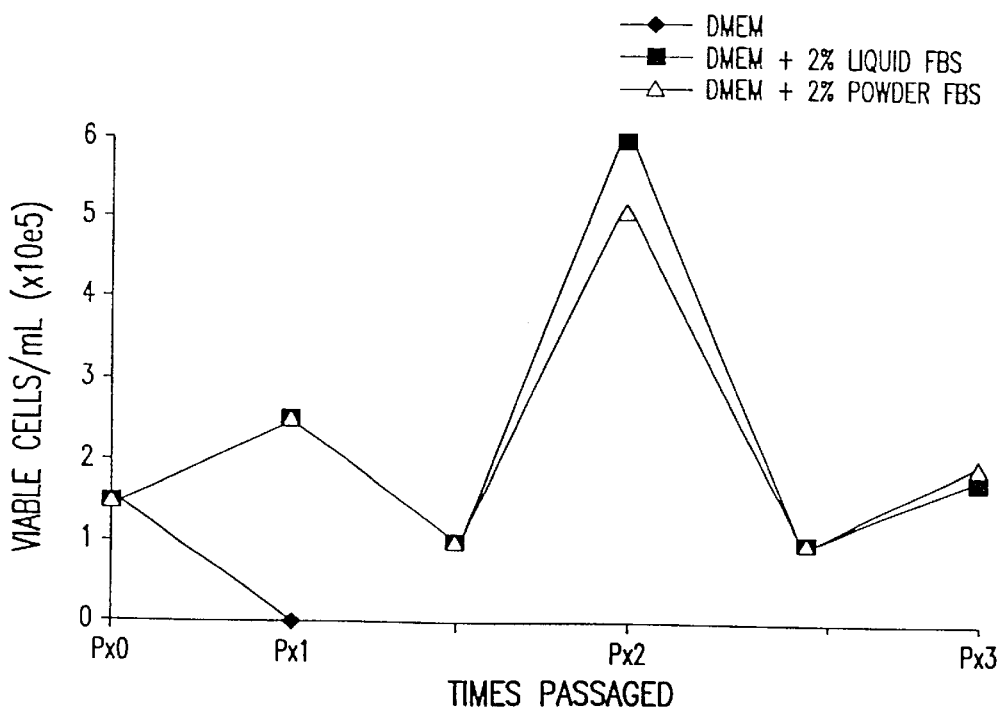

To determine if agglomeration of the FBS affected its ability to support cell growth and passage, SP2/0 cells were plated into DMEM containing either 2% agglomerated ("dry") FBS or 2% liquid FBS and growth rates and passage recovery examined. As shown in FIG. 2A, cells plated into media containing agglomerated FBS demonstrated similar growth kinetics as did cells plated into media containing liquid FBS. Similarly, cells in media containing agglomerated FBS recovered from passage with practically identical growth rates as cells in media containing liquid FBS (FIG. 2B). Together, these results indicate that the agglomerated FBS of the present invention performs approximately equivalently to liquid FBS in supporting growth and passage of cultured cells.

EXAMPLE 8

Production of 100% Serum Powder by Spray-Drying

As an alternative to fluid bed processing, the feasibility of producing dry powdered serum by spray-drying technology was examined. A three foot diameter laboratory spray drier (Mobile Minor Spray Dryer; NIRO, Columbia, Md.) was used to prepare the powdered serum. Liquid FBS was aspirated into the spray-dryer and atomized through a Schlick 940 nozzle located in the middle of the air dispenser, and the drying air was introduced into the atomizer through the top air dispenser of the apparatus. Spray drying was conducted under the following conditions: inlet air temperature=200° C.; outlet air temperature=70° C., atomizing air pressure for the nozzle=2.0 bar; air flow=80.0 kg/hour; spray rate=65 g/minute. During development of these methods, an initial outlet air temperature of 60° C. was used; however, this temperature was found to be too low, and the spray rate was adjusted back to a level to achieve an outlet temperature of about 70° C. which was found to be optimal. Following spray-drying, powdered serum was collected at the cyclone of the apparatus, and process air was filtered through an exhaust filter prior to recirculation within the apparatus.

Figure 3A:
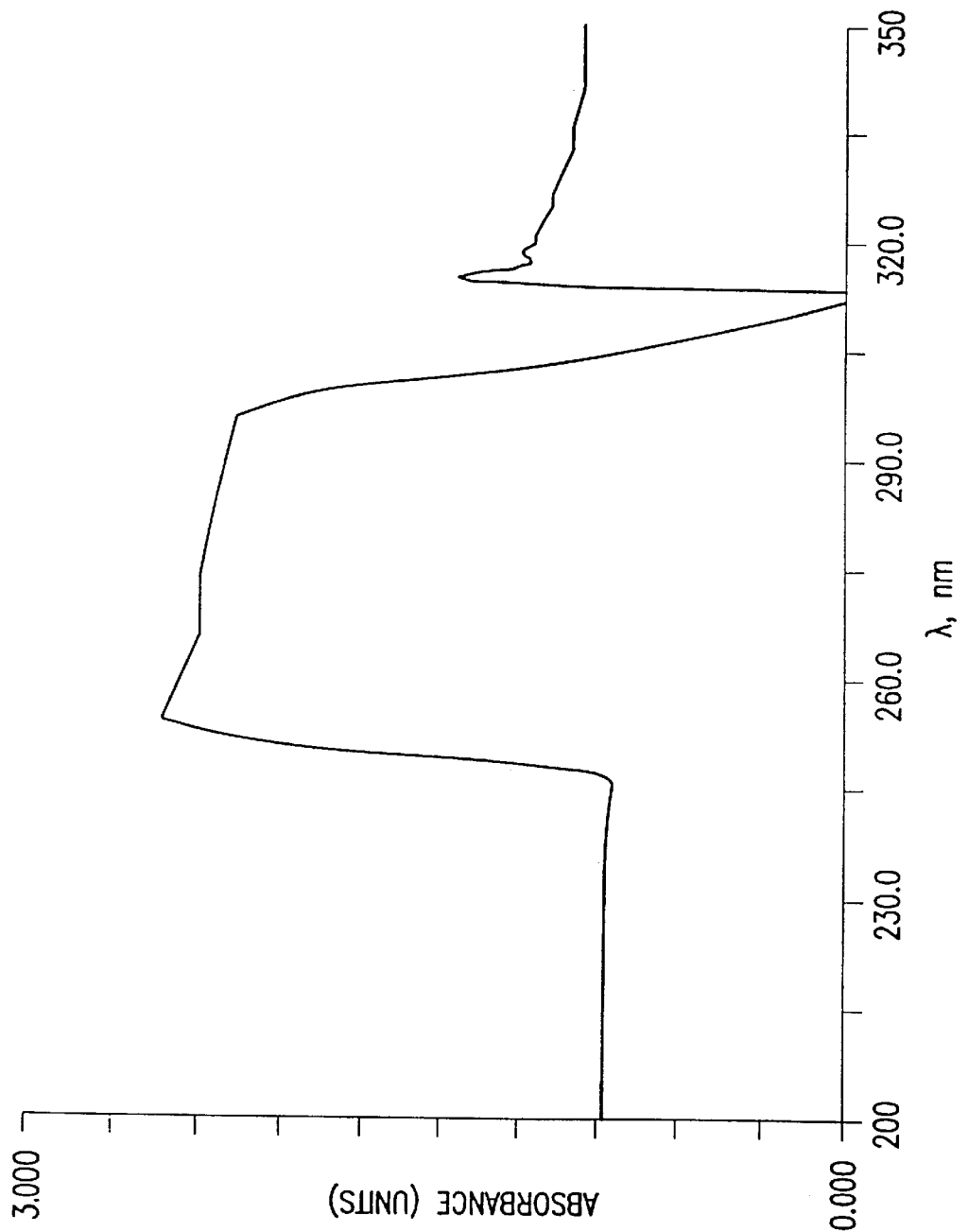
FIG. 3 is composite of histograms of spectrophotometric scans ($\lambda$=200–350 nm) of powdered fetal bovine serum (FBS) prepared by spray-drying according to the methods of the invention (FIG. 3A) or of standard liquid FBS (FIG. 3B).

Following production, the powdered serum was characterized with respect to its physical properties, compared to liquid FBS from the same source lot. Samples taken from different stages of the production lot (samples "A" and "B") were reconstituted at a concentration of 60.44 g/L in endotoxin-free distilled water (Life Technologies, Inc.), and were examined for endotoxin levels using a Limulus Amoebocyte Lysate test (Life Technologies, Inc.), for hemoglobin levels (by spectrophotometrically measuring absorbance at 525 nm), and by UV/Vis spectrophotometry. Results are shown in Table 1, and in FIGS. 3A and 3B.

TABLE 1

Physical Characterization of Powdered Serum.

| Material Tested | Endotoxin Level (EU/ml) | Hemoglobin (mg/100 ml) |
|---|---|---|
| Powdered FBS, Sample "A" | 0.6 | 7.7 |
| Powdered FBS, Sample "B" | <0.3 | 7.7 |
| Liquid FBS (control) | <0.3 | 7.2 |

Figure 3B:
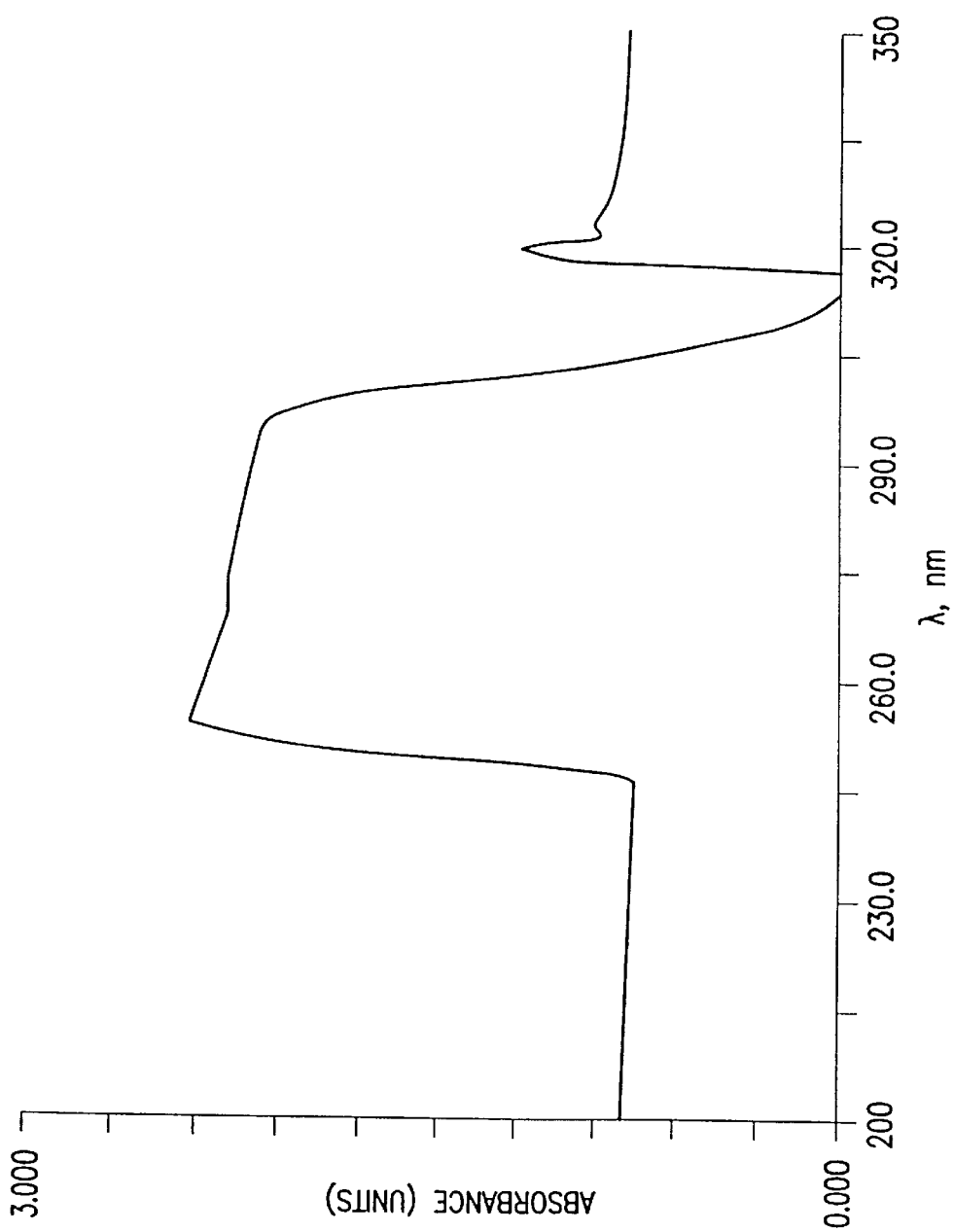

As seen in Table 1, powdered FBS demonstrated endotoxin and hemoglobin levels similar to those of the liquid FBS that served as the source material for production of the powdered FBS. Moreover, samples taken from different stages of the production process demonstrated nearly identical endotoxin and hemoglobin levels, indicating that the present methods result in the production of material with approximately uniform physical consistency across the production lot. When samples of powdered and liquid FBS were examined by UV/visible spectrophotometry (FIG. 3), the trace observed for powdered FBS (FIG. 3A) was indistinguishable from that obtained for the source liquid FBS (FIG. 3B). Together, these results indicate that serum powder prepared by the present spray-drying methods have nearly identical physical characteristics as those of liquid sera from which the powders are prepared. Taken together with those of Example 7 above (see, e.g., FIG. 1), these results demonstrate that the methods provided by the present invention result in the production of powdered sera with physical characteristics that are unaltered from those of the source liquid sera. Unexpectedly, as shown in Example 18, it was found that endotoxin level in serum is reduced with spray-drying. Failure to detect such reduction here may be attributed to the low levels of endotoxin present in the sample and/or the sensitivity of the assay.

EXAMPLE 9

Production of Automatically pH-Adjusted Powdered Culture Media

One reason that sodium bicarbonate is never included in powdered media is that any moisture, even that in the air, may result in an acidic condition within the pouch that will result in the liberation of $CO_2$ gas. The pouches will become swollen and produce what have been called "pillows." With fluid bed processing, the humidity within the apparatus is reduced essentially to negligible levels prior to the end of the process. We have made RPMI-1640 powdered media containing sodium bicarbonate and have not seen evidence of "pillow" formation.

Figure 4A:
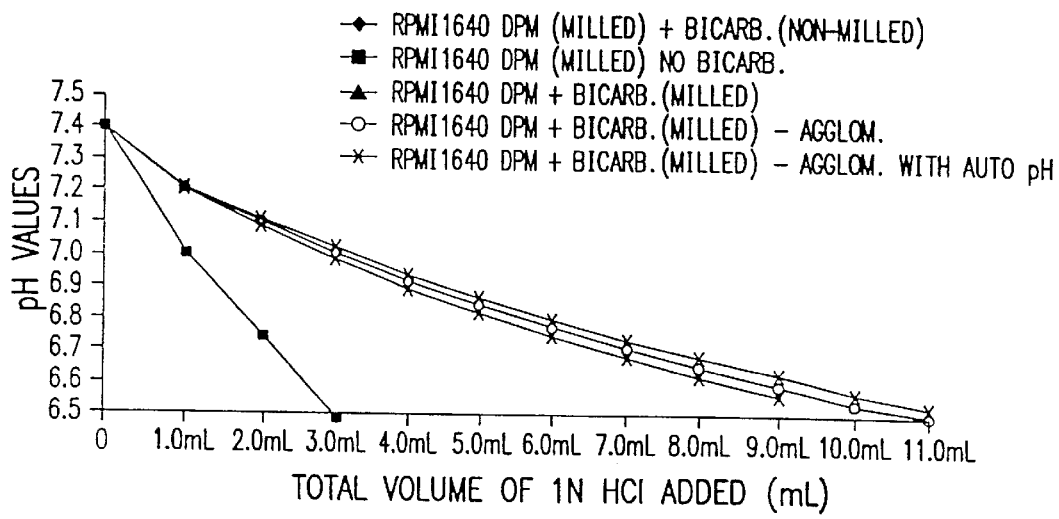
FIG. 4 is a composite of line graphs showing the pH titration (buffer capacity), on two different dates (FIGS. 4A and 4B), of various dry powdered media (DPM) prepared by the methods of the invention or by ball-milling, with or without the addition of sodium bicarbonate.
Figure 4B:
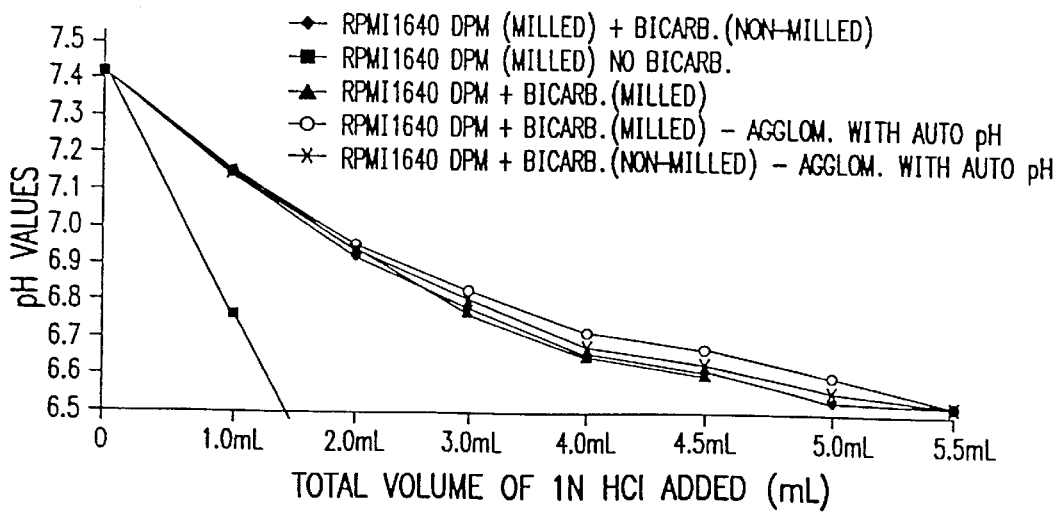

In order to make a pH-adjusted powdered media, it is necessary to add the pH-adjusting chemical (usually HCl or NaOH) to the powder to bring the pH to about 7.0–7.4 upon addition to water. Once sodium bicarbonate is added to the powder, many powdered media reconstitute in water on the basic side of neutrality and need HCl addition. Adding HCl to a powder containing sodium bicarbonate would be expected to be problematic. However, since the added liquid (5N HCl in this case) never results in a moistened or "liquid" state inside the fluid bed apparatus, the sodium bicarbonate does not give off $CO_2$ gas and fully retains its buffering capacity. This has been examined in the present studies by pH-titering experiments: equal amounts of acid, in two separate experiments (FIGS. 4A and 4B) were found to reduce the pH of agglomerated media and automatic pH-adjusted agglomerated media by an identical amount as that for a standard medium with sodium bicarbonate added to the liquid at the time of reconstitution. These results indicate that both agglomeration with subsequent adjustment of pH, and agglomeration with adjustment of pH during the agglomeration process, function equally well to produce powdered culture media with significant buffering capacity.

EXAMPLE 10

Effect of Agglomeration on Dissolution Rates of Culture Media

Figure 5A:
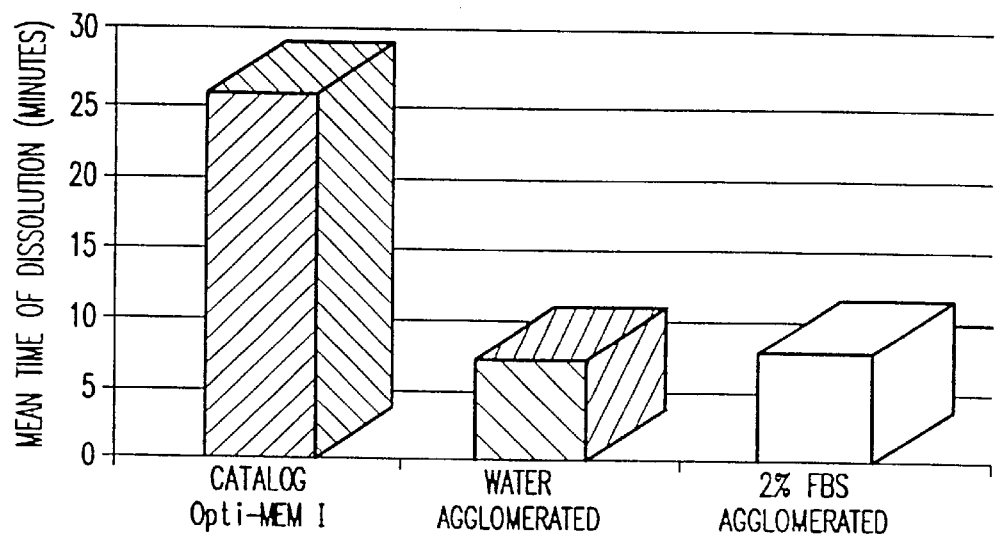
FIG. 5 is a composite of bar graphs showing the effect of agglomeration on dissolution rates (in water) of Opti-MEM I™ (FIG. 5A) or DMEM (FIG. 5B). Media were agglomerated with water or FBS as indicated.
Figure 5B:
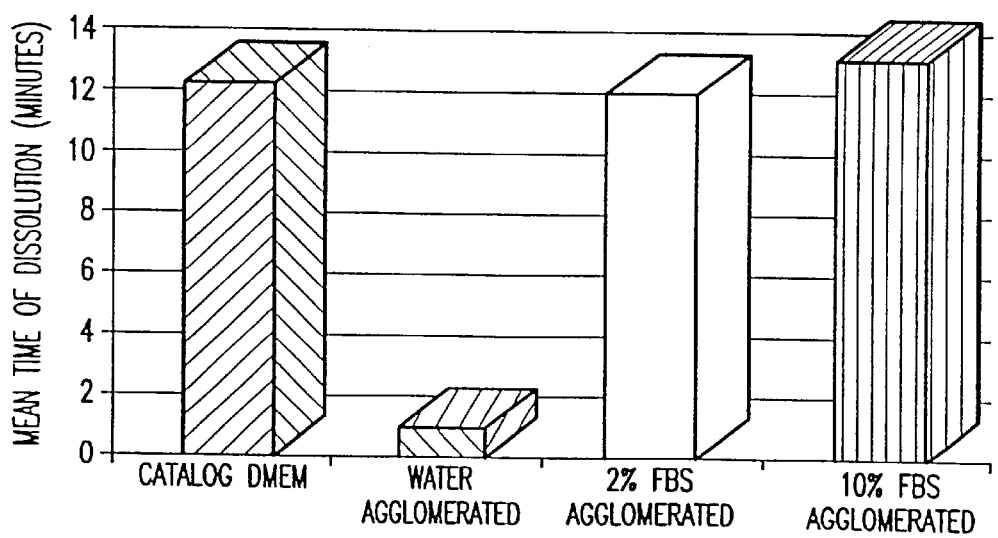

To examine the effect of agglomeration of culture media on the rate of dissolution of the media, samples of Opti-MEM I™ or DMEM were agglomerated with water or with FBS (2% only for Opti-MEM I; 2% or 10% for DMEM). Upon reconstitution of the agglomerated media in water, the time dissolution of the agglomerated Opti-MEM I occurred much more quickly than did dissolution of standard powdered Opti-MEM I (FIG. 5A); results were identical for water- and FBS-agglomerated Opti-MEM I. Interestingly, however, while water-agglomerated DMEM dissolved in water much more quickly than did standard powdered DMEM, the FBS-agglomerated DMEM did not (FIG. 5B).

Due to the open structure of the agglomerated powdered media (as opposed to traditional powdered media), capillary action brings water into close proximity with all of the powder particles. This prevents the appearance of powder "balls," a complication observed upon reconstitution of most standard powdered media that leads to longer dissolution times. In addition to more rapid dissolution, agglomerated media demonstrated reduced dusting as well. These results indicate that water-agglomerated culture media, and some FBS-agglomerated culture media, are much more rapidly dissolving and generate less dust than traditional powdered culture media.

EXAMPLE 11

Cell Growth and Subculturing in Reconstituted Agglomerated Culture Media

Many uses of culture media require additions of large molecular weight proteins such as serum or albumin. These molecules may be in the form of solutions or even powder in the case of albumin. However, in order to insure uniformity of powdered media, these proteins are usually added not as a powder but as liquid after reconstitution of the bulk powdered media to a liquid medium. This presents some inconvenience since, for example, serum must be stored in the freezer to maintain performance over time. This adds expense and inconvenience since the serum must be added aseptically to the media, increasing chances of contamination. If filtration is done after addition of serum, another processing step is needed. There would therefore be advantages to being able to provide serum as an integral part of the powdered media.

Therefore, culture media were agglomerated with water or with various concentrations of FBS. FBS was added to the powdered media by injecting it into the air-suspended dry powdered media at high evaporation rates, as generally outlined above. The level of serum supplementation was 2% in Opti-MEM I media, and 2% or 10% in DMEM. The growth and passage success of various cell lines in these media were then assessed.

Figure 6A:
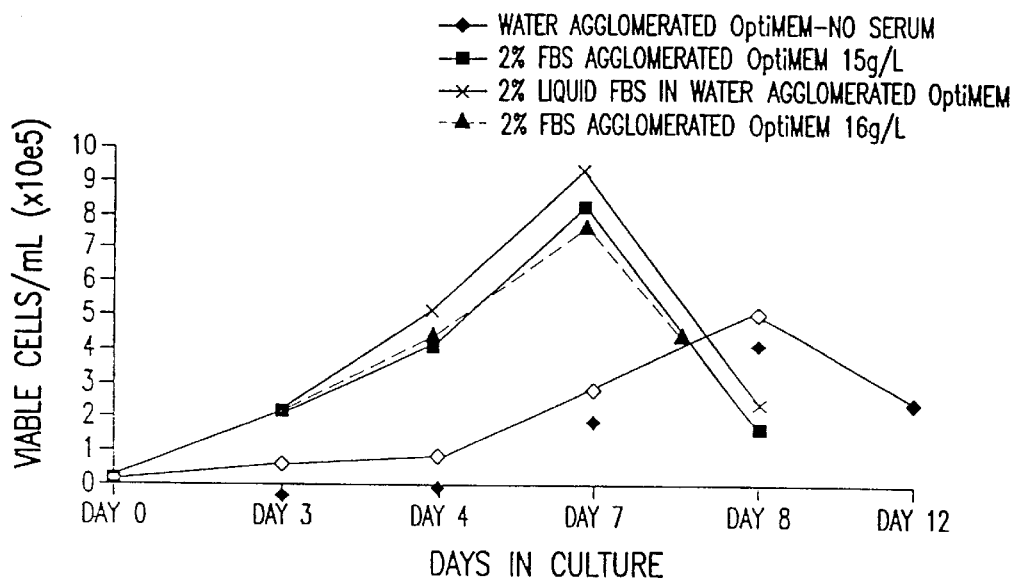
FIG. 6 is a composite of line graphs showing growth over seven days of SP2/0 cells in agglomerated Opti-MEM I™ (FIG. 6A) or DMEM (FIG. 6B), both containing 2% FBS.
Figure 6B:
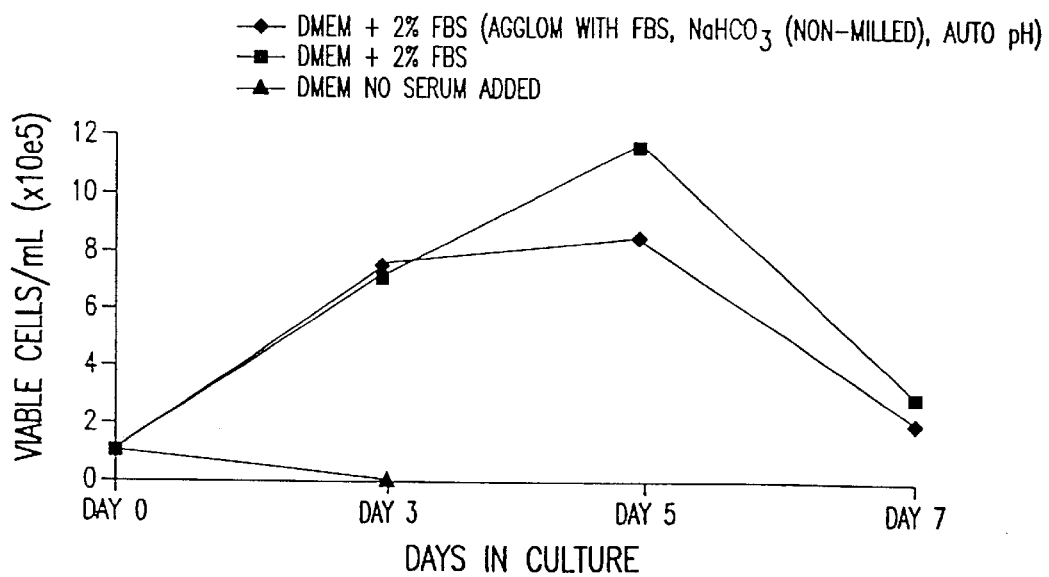
Figure 7A:
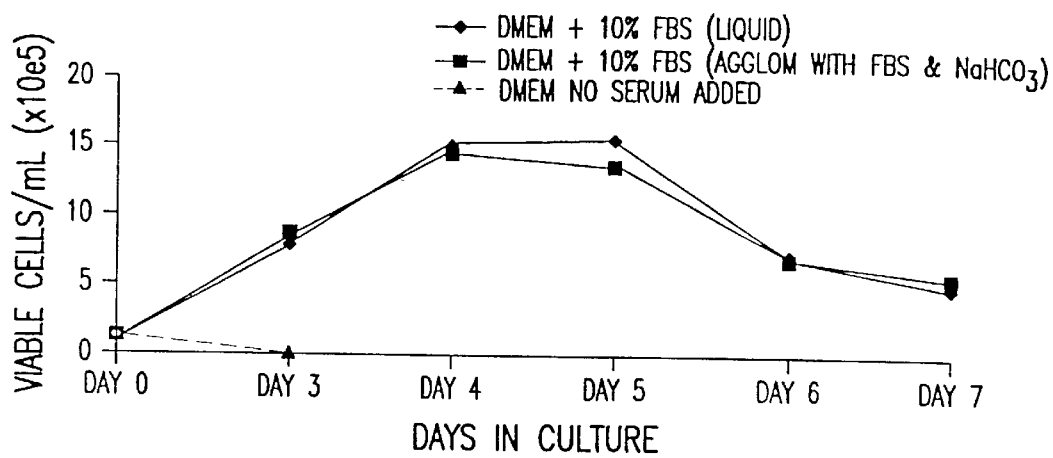
FIG. 7 is a composite of line graphs showing growth over seven days of SP2/0 cells (FIG. 7A), AE-1 cells (FIG. 7B) and L5.1 cells (FIG. 7C) in agglomerated DMEM containing 10% FBS.
Figure 7B:
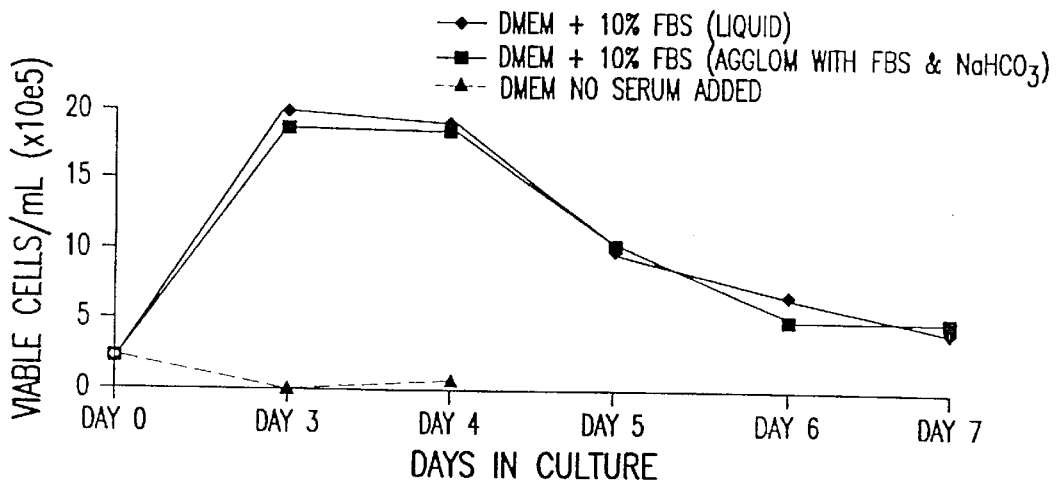
Figure 7C:
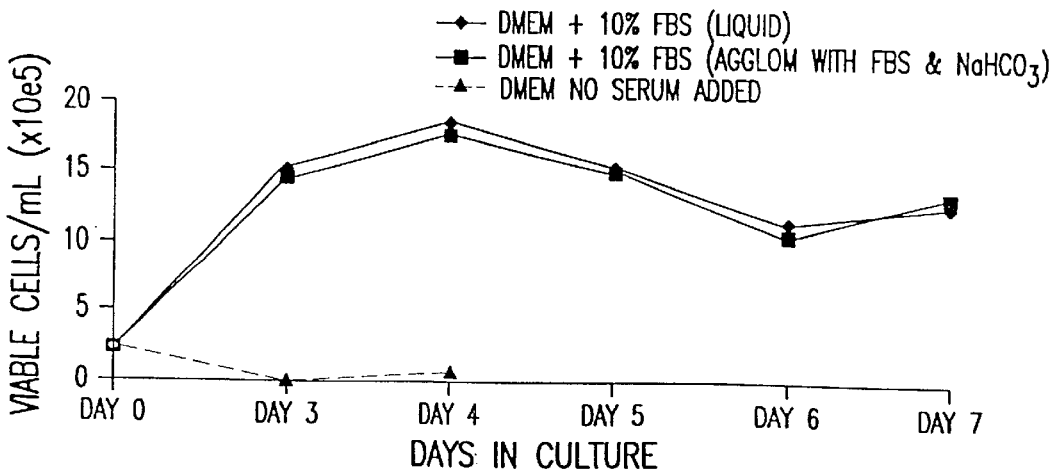
Figure 8A:
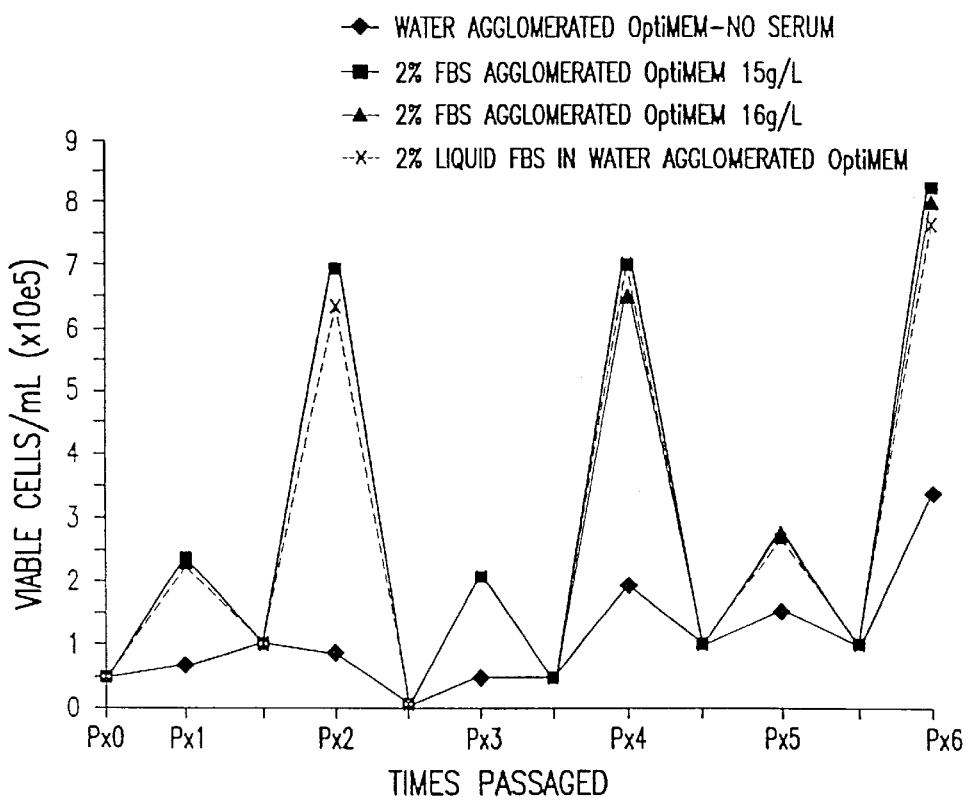
FIG. 8 is a composite of line graphs showing passage success of SP2/0 cells in Opti-MEM I™ (FIG. 8A) or DMEM (FIG. 8B), agglomerated with either water or FBS, supplemented with 2% FBS.
Figure 8B:
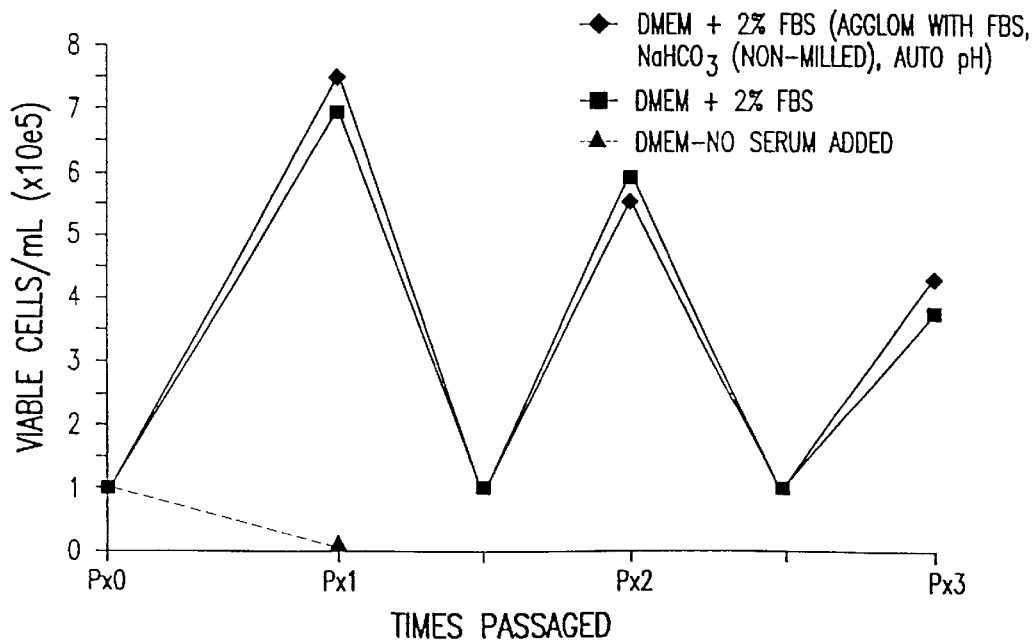
Figure 9A:
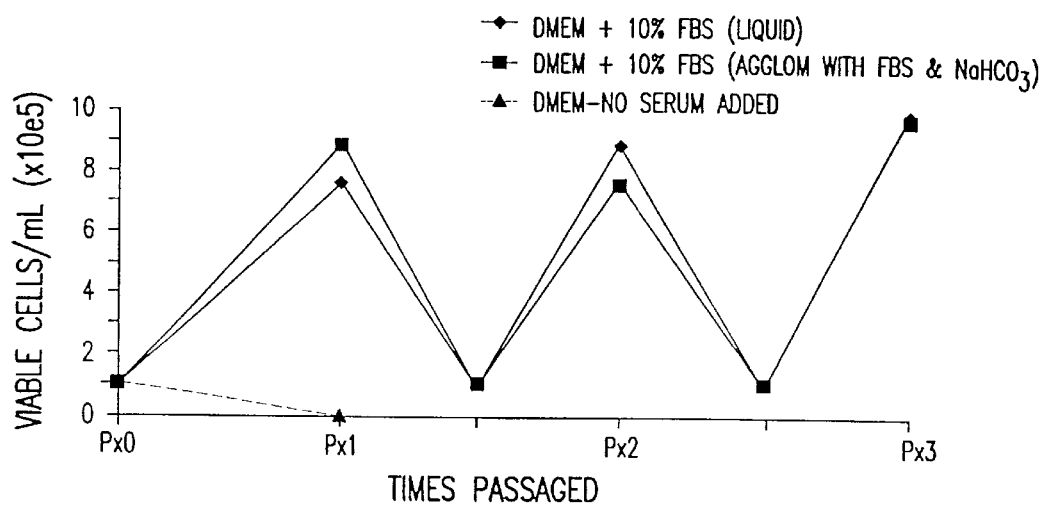
FIG. 9 is a composite of line graphs showing passage success of SP2/0 cells (FIG. 9A), AE-1 cells (FIG. 9B) and L5.1 cells (FIG. 9C) in DMEM agglomerated with FBS and sodium bicarbonate and supplemented with 10% FBS.
Figure 9B:
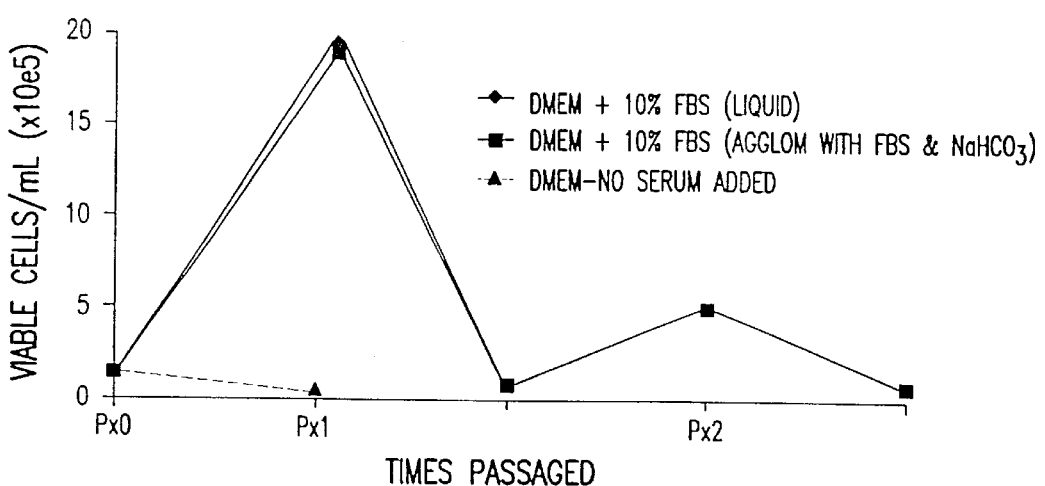
Figure 9C:
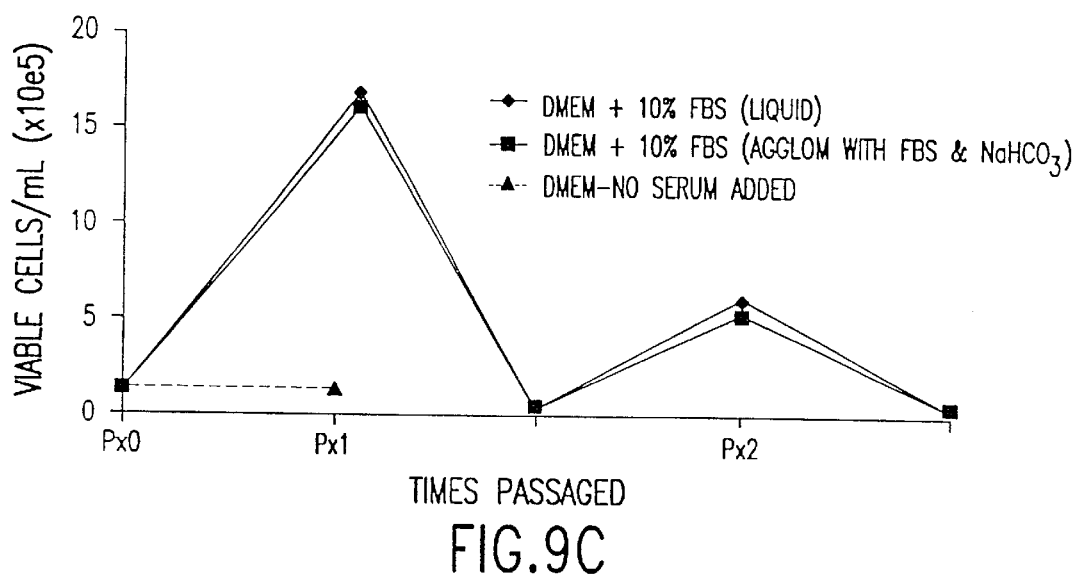
Figure 10:
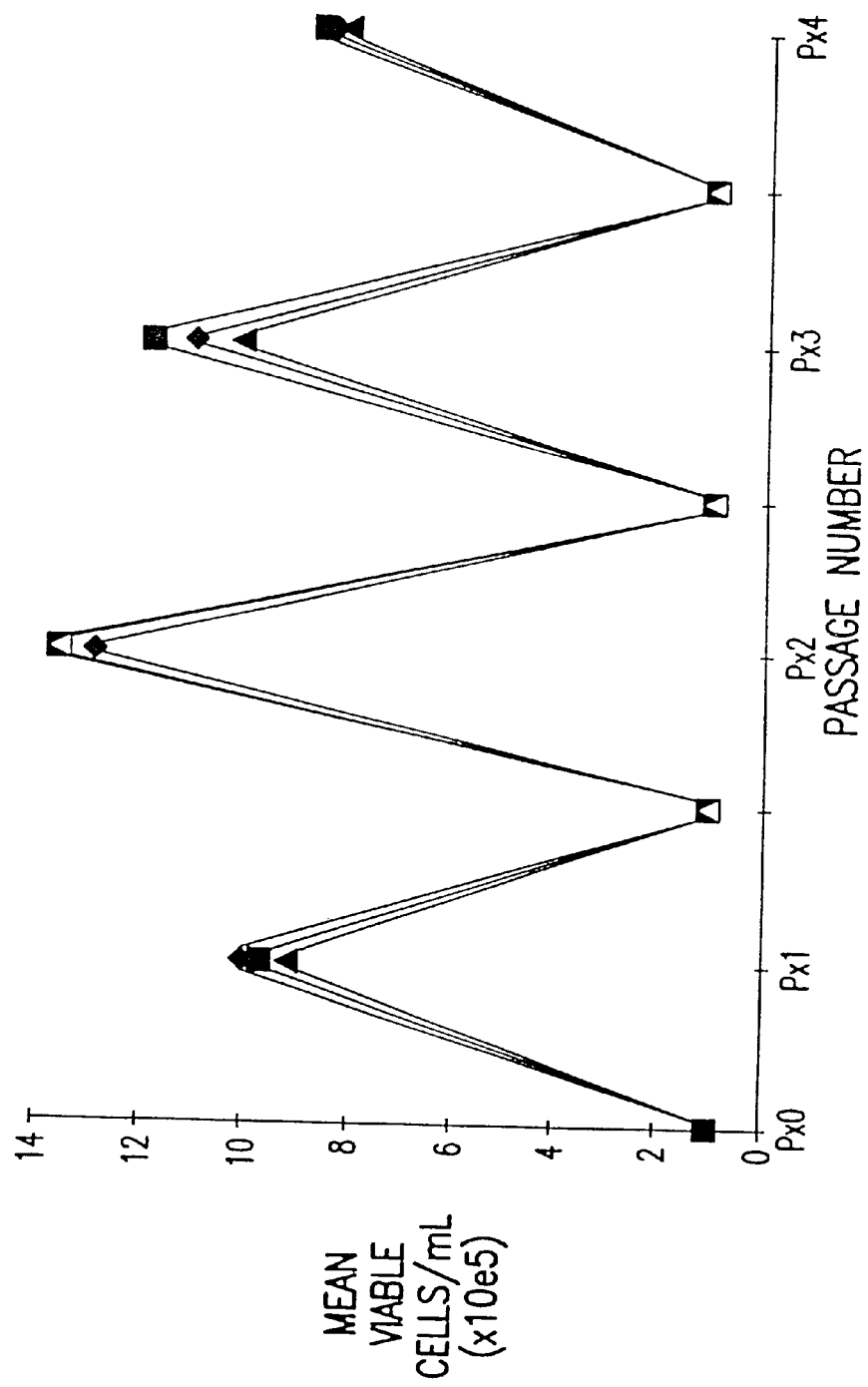
FIG. 10 is a line graph showing the growth of SP2/0 cells over four passages in standard water-reconstituted powdered culture media (control media), or in agglomerated powdered culture media prepared in large-scale amounts according to the methods of the invention. Results are shown for control media (□), water-agglomerated powdered culture media of the invention (♦) and water-agglomerated auto-pH powdered culture media (containing sodium bicarbonate) of the invention (■).

As shown in FIG. 6, SP2/0 cells demonstrated similar growth rates when grown in Opti-MEM I agglomerated with either water or with FBS (FIG. 6A), compared to cells grown under conventional culture conditions (liquid serum added to water-reconstituted powdered media). Similar results were observed with SP2/0 cells cultured in water- and FBS-agglomerated DMEM supplemented with 2% FBS (FIG. 6B), and with SP2/0 cells (FIG. 7A), AE-1 cells (FIG. 7B) and L5.1 cells (FIG. 7C) cultured in water- and FBS-agglomerated DMEM supplemented with 10% FBS. In addition, SP2/0 cells showed approximately similar recovery rates from passage when cultured in water- or agglomerated Opti-MEM I and DMEM supplemented with 2% FBS (FIGS. 8A and 8B, respectively), as did SP2/0 cells, AE-1 cells and L5.1 cells cultured in water- and FBS-agglomerated DMEM supplemented with 10% FBS (FIGS. 9A, 9B and 9C, respectively) and SP2/0 cells cultured in water-agglomerated DMEM supplemented with 5% FBS (FIG. 10). Furthermore, SP2/0 cells demonstrated identical passage characteristics in water-agglomerated media produced in large batches and in automatically pH-adjusting powdered DMEM containing sodium bicarbonate as they did in standard liquid DMEM supplemented with 5% FBS (FIG. 10).

Together, these results indicate that culture media supplements such as animal sera (e.g., FBS) may be agglomerated directly into culture media, and that supplementation of culture media during the agglomeration process in this way produces a culture medium that provides optimal support of growth and passage of a variety of cultured cells. Furthermore, these results indicate that the present culture media powders may be successfully produced in large batches, including the automatically pH-adjusting media of the invention that contain sodium bicarbonate.

EXAMPLE 12

Cell Growth in Culture Media Supplemented with Spray-Dried Serum Powder

Figure 12A:
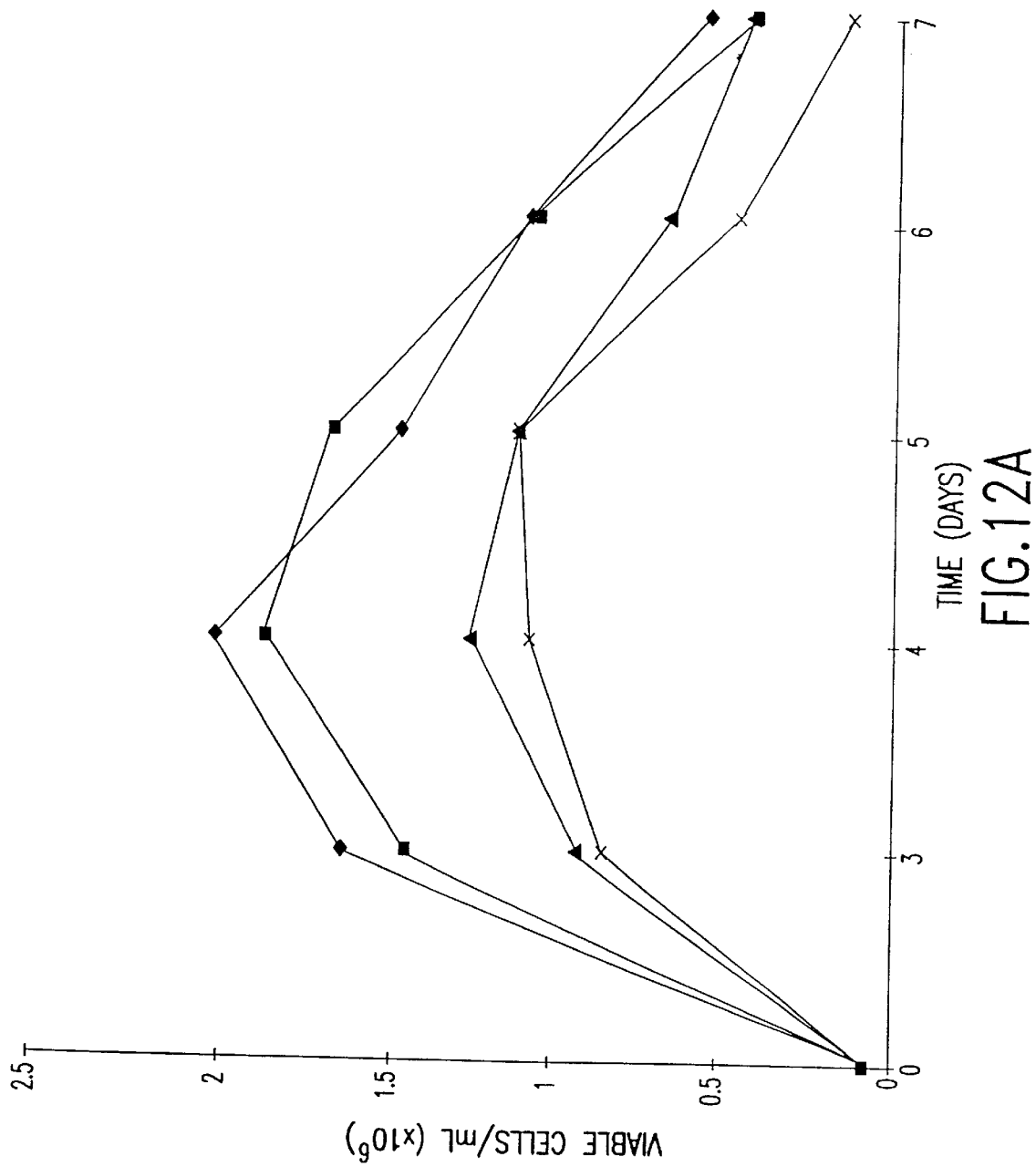
FIG. 12 is a line graph of SP2/0 cells cultured over seven days in medium containing 2% (Δ) or 10% (♦) liquid FBS, or 2% (x) or 10% (■) powdered FBS prepared by the spray-drying methods of the invention. Duplicate experiments are shown in FIGS. 12A and 12B.
Figure 12B:
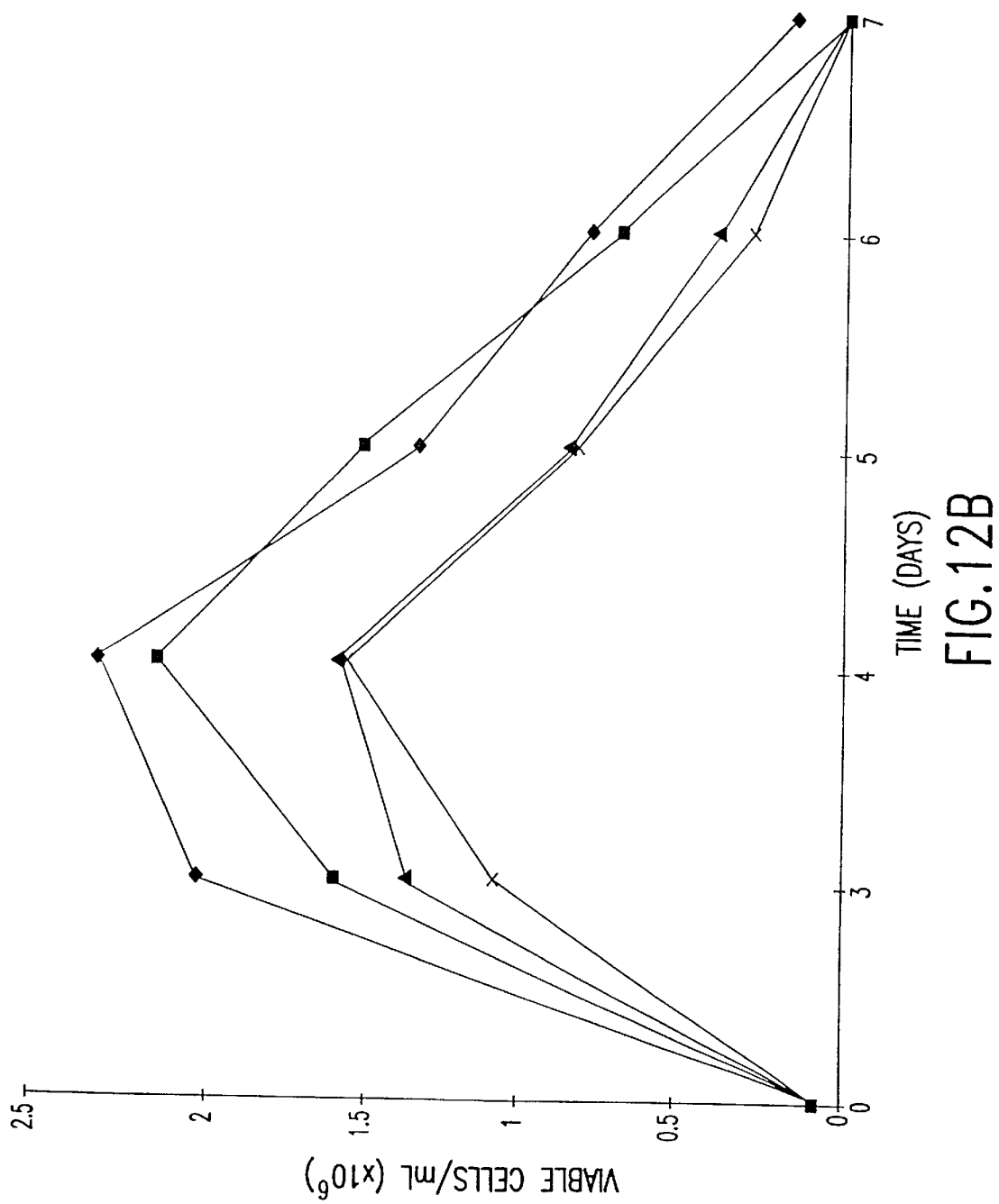
Figure 13:
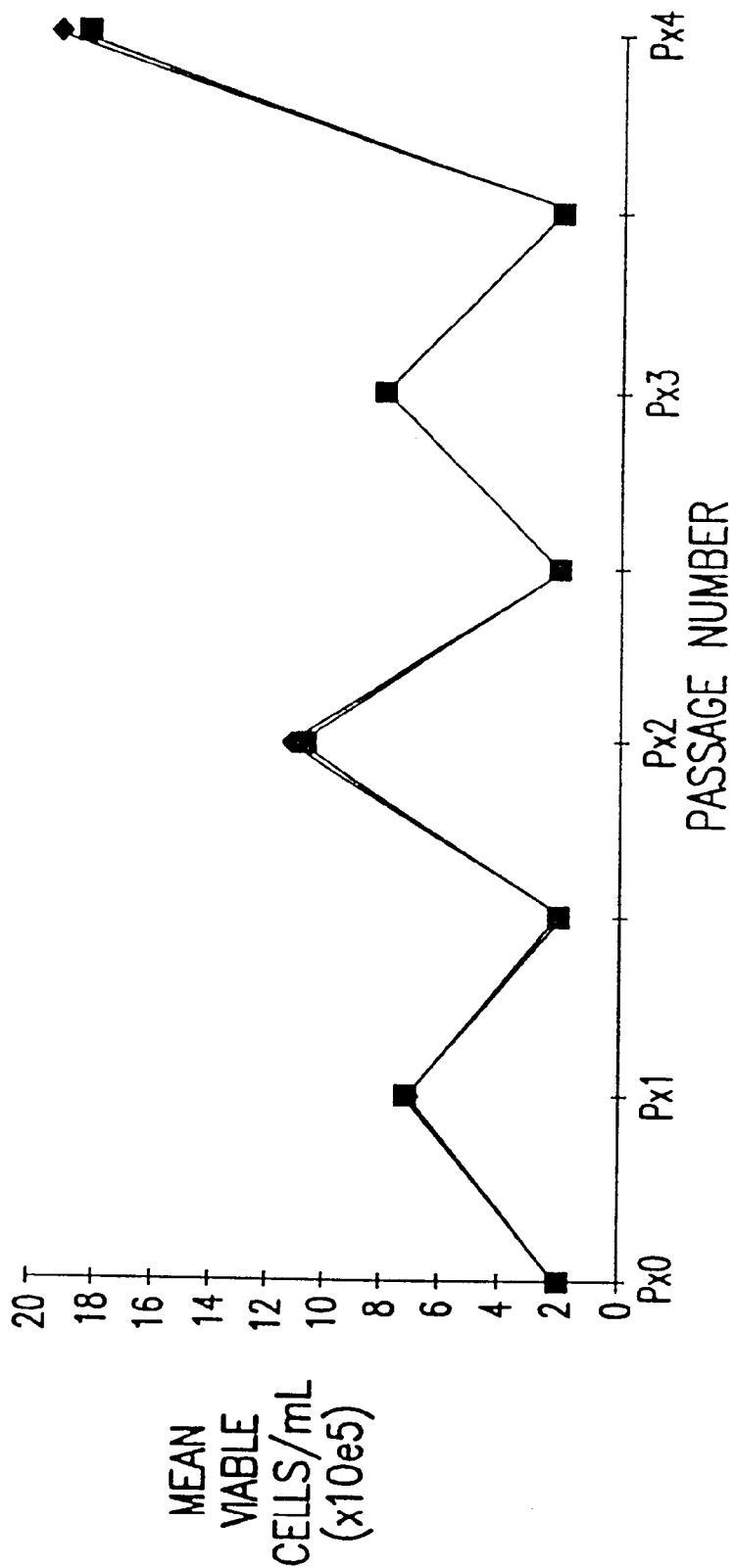
FIG. 13 is a line graph of AE-1 cell growth over four passages in media containing 5% liquid FBS (♦) or 5% powdered FBS prepared by the spray-drying methods of the invention (■).

As a corollary to the experiments shown in Example 7, AE-1 cells and SP2/0 cells were plated into DMEM containing either 2% or 10% spray-dried FBS prepared as described in Example 8, or containing 2% or 10% liquid FBS, and growth rates and passage recovery of the cells were examined. Cells were inoculated into triplicate 25 cm$^2$ flasks at a density of $1 \times 10^5$ cells/ml in 10 ml of media. Viable cell density was determined on days 3–7, and each cell line was tested twice. Results are shown in FIGS. 11–13.

Figure 11A:
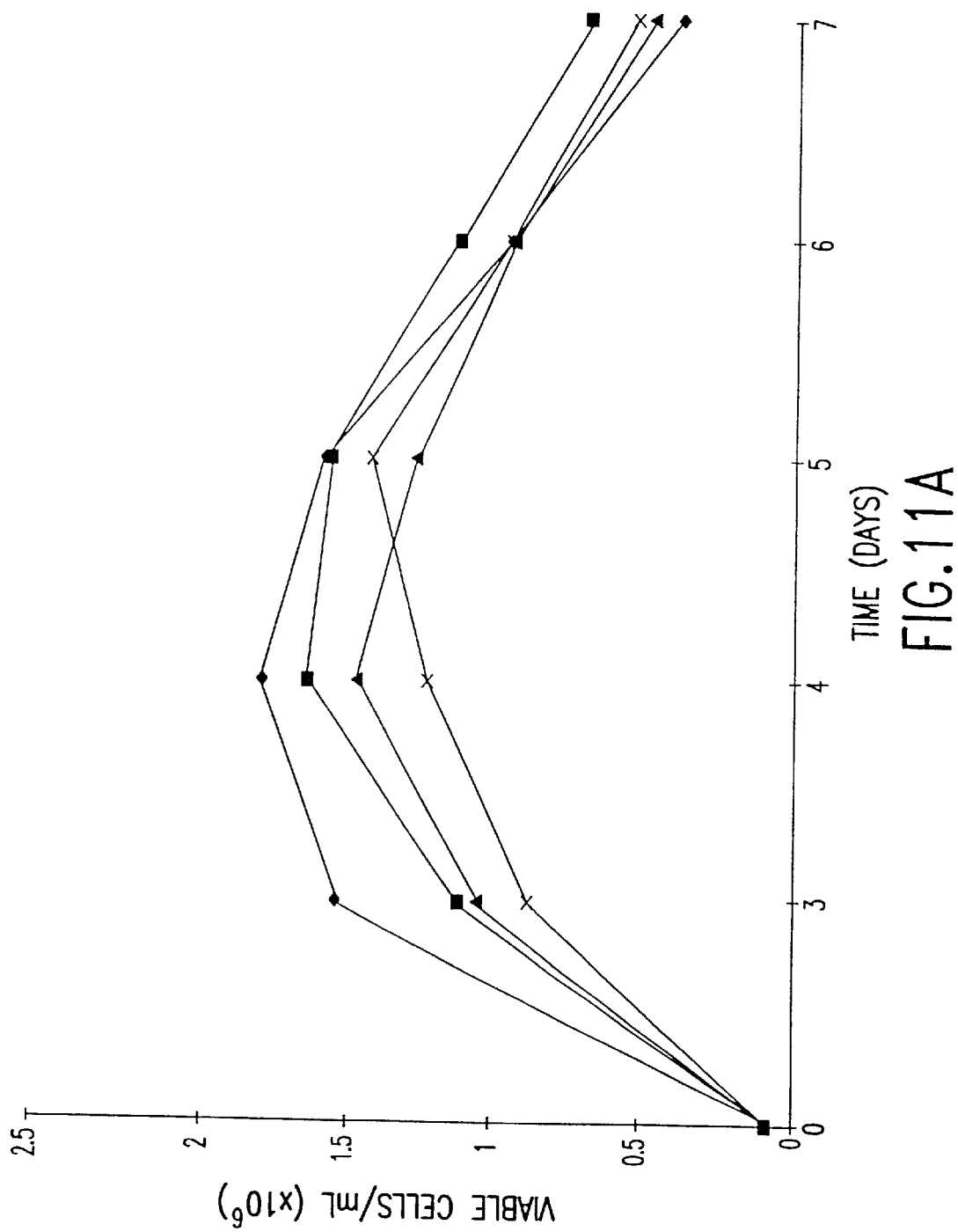
FIG. 11 is a line graph of AE-1 cells cultured over six or seven days in medium containing 2% (Δ) or 10% (♦) liquid fetal bovine serum (FBS), or 2% (x) or 10% (■) powdered FBS prepared by the spray-drying methods of the invention. Duplicate experiments are shown in FIGS. 11A and 11B.
Figure 11B:
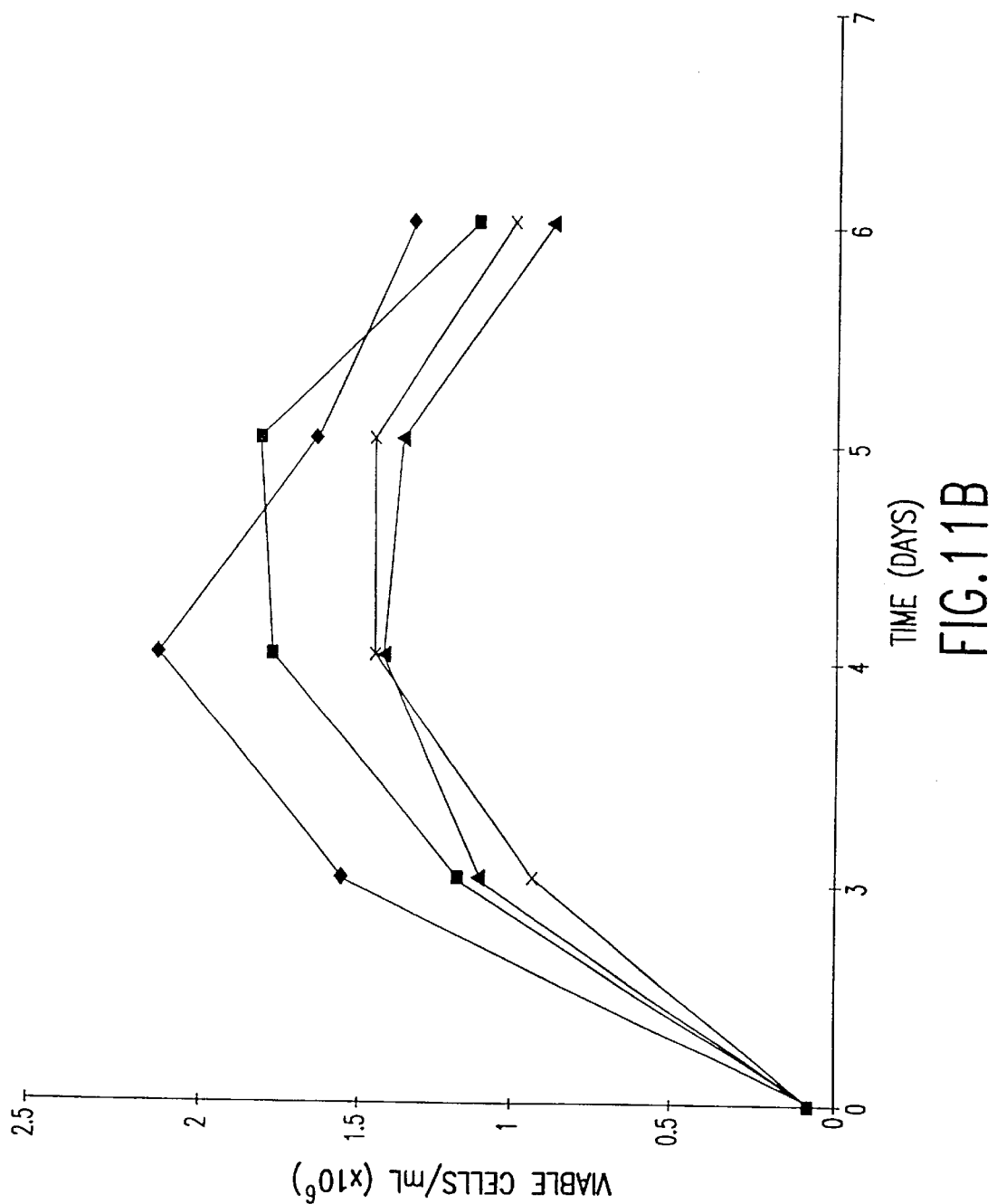

As shown in FIG. 11, AE-1 cells cultured in media containing powdered FBS demonstrated similar growth kinetics to those cells cultured in media containing standard liquid FBS. As expected, the cells demonstrated more rapid growth to a higher density in culture media containing 10% FBS than in media containing 2% FBS, and demonstrated peak growth by about day four. Similar kinetics were observed for two separate experiments (FIGS. 11A and 11B), indicating that these results were reproducible. Analogous results were obtained in two experiments in which the growth rates of SP2/0 cells were measured in media containing powdered or liquid FBS (FIGS. 12A and 12B). In addition, AE-1 cells cultured in media containing 5% powdered FBS recovered from passage with identical growth rates as cells in media containing liquid FBS (FIG. 13).

These results indicate that the powdered FBS prepared by the spray-drying methods of the present invention performs approximately equivalently to liquid FBS in supporting growth and passage of cultured cells. Together with those from Examples 7 and 8, these results indicate that the methods of the present invention may be used to produce powdered FBS, by fluid bed or spray-drying technologies, that demonstrates nearly identical physical and performance characteristics as those of liquid FBS.

EXAMPLE 13

Effect of Irradiation on Performance of Agglomerated Media

Recently, concerns have been raised about the biological purity of media and media components (including supplements) used for bioproduction, particularly in the biotechnology industry. Gamma irradiation is a sterilization process that is known to work well with certain liquids and powders that are not typically amenable to sterilization by heat or toxic gas exposure. Therefore, samples of water- or FBS-agglomerated culture media were γ irradiated with a cobalt source at 25 kGy for up to several days, and the growth rates of various cell types examined.

In one set of experiments, SP2/0 cells were inoculated into various media at $1 \times 10^5$ cells/ml and cultured at 37° C. At various intervals, samples were obtained aseptically and cell counts determined by Coulter counting and viability determined by trypan blue exclusion. Media were prepared by dissolving sufficient powdered media to make a 1× solution in 1L of water, stirring and filtering through a 0.22 μm filter. Results are shown in the graph in FIG. 14. Those conditions on the graph that state "pwdr FBS" on the graph refer to the addition of powdered FBS (prepared as in Examples 7 or 8 above) to the reconstituted 1× medium prepared from either standard powdered media or from agglomerated media (irradiated or non-irradiated). Those conditions on the graph that state "Irradia. agglom. DMEM+FBS" refer to use of the fluid bed to make the agglomerated media by spraying FBS into the powdered media (standard or agglomerated) to make an FBS-agglomerated media.

Figure 14:
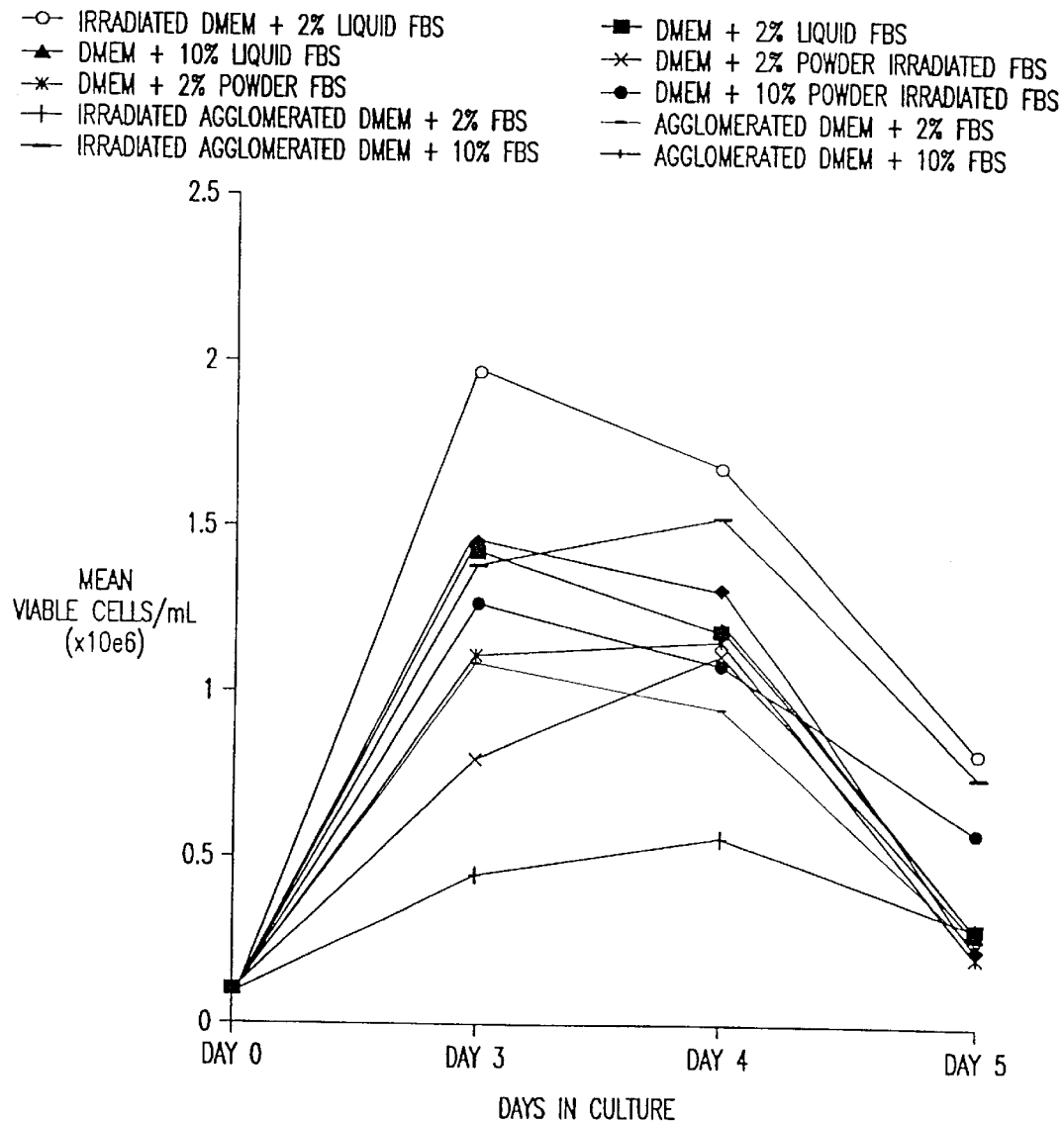
FIG. 14 is a line graph indicating the effect of $\gamma$ irradiation and agglomeration on the growth of SP2/0 cells over five days.

As shown in FIG. 14, γ irradiation of standard powdered basal media and agglomerated basal media did not deleteriously affect the ability of these media to support SP2/0 cell growth. In addition, while irradiation did negatively impact powdered media containing powdered FBS, and powdered FBS itself, this effect diminished with increasing serum concentration.

To more broadly examine these γ irradiation effects, samples of VERO cells were inoculated into VP-SFM™ that had been conventionally reconstituted or agglomerated as above. To the powdered media in the agglomeration chamber, however, epidermal growth factor (EGF) and ferric citrate chelate, traditional supplements for this media, were added via the spray nozzle during agglomeration. Media were then used directly or were γ irradiated as described above. Cells were inoculated at $3 \times 10^5$ cells/flask into T-25 flasks and incubated at 37° C. Cell counts and viability were performed as described above, with results shown in FIG. 15.

Figure 15:
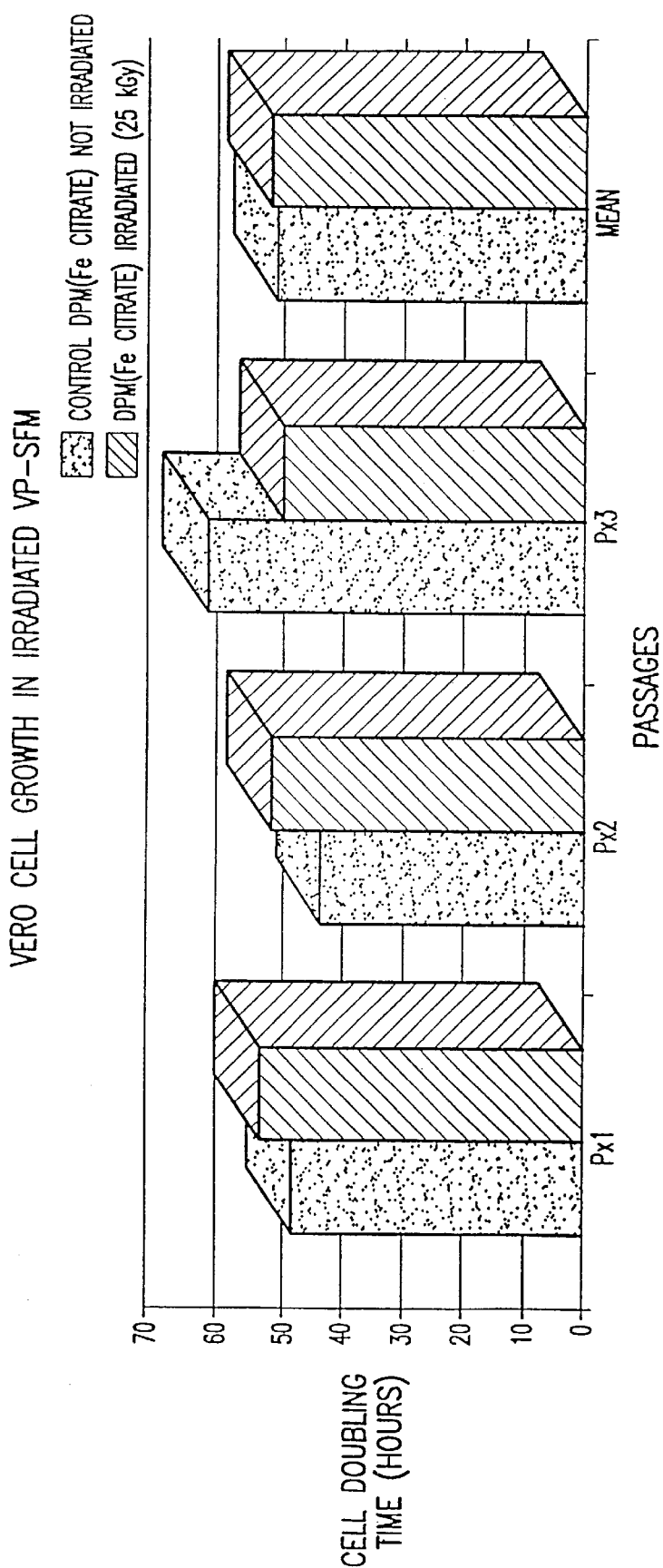
FIG. 15 is a bar graph indicating the effect of $\gamma$ irradiation of the agglomerated culture media on the growth of VERO cells.

As seen in FIG. 15, VERO cells demonstrated approximately equivalent growth and passage success when cultured in agglomerated media that had been γ-irradiated as in agglomerated media that had not been γ-irradiated. Furthermore, irradiation of the media had no effect on the low-level culture supplements EGF and ferric citrate chelate that were present in the media.

These results indicate that γ irradiation may be used as a sterilization technique in the preparation of many bulk agglomerated culture media, including those containing serum, EGF or other supplements, by the present methods.

EXAMPLE 14

Effect of Irradiation on Performance of Powdered Media Supplements

To demonstrate the efficacy of the present methods in producing sterile media supplements, lyophilized human holo-transferrin was irradiated by exposure to a cobalt γ source at 25 kGy for about 3 days at −70° C. or at room temperature. 293 cells were then cultured in media that were supplemented with irradiated transferrin or with control transferrin that had not been irradiated (stored at −70° C. or at room temperature), and cell growth compared to that of standard transferrin-containing culture media or media that contained no transferrin.

Mid-log phase 293 cells that were growing in serum-free 293 medium (293 SFM) were harvested, washed once at 200× g for 5 minutes and resuspended in transferrin-free 293 SFM for counting and viability determination. Cells were plated into triplicate 125 ml Ehrlenmeyer flasks at a density of $3 \times 10^5$ cells/ml in a volume of 20 ml in 293 SFM (positive control), transferrin-free 293 SFM (negative control), in 293 SFM containing non-irradiated transferrin stored at −70° C. or at room temperature, or in 293 SFM containing irradiated transferrin prepared as described above. Flasks were placed into a rotary shaker set at about 125 rpm, in a 37° C. incubator equilibrated with an atmosphere of 8% $CO_2$/92% air. Daily cell counts were determined using a Coulter particle counter and viabilities were determined by trypan blue exclusion according to standard procedures. When the cells reached a density of about 1.2 to $1.7 \times 10^6$ per flask, the contents of one of the flasks of each sample were harvested, centrifuged, resuspended into fresh medium and passaged into three new flasks. Cell counts and viabilities of the previous and next passages were then performed as described above. Four consecutive passages of cells incubated under the above conditions were tested.

Figure 16A:
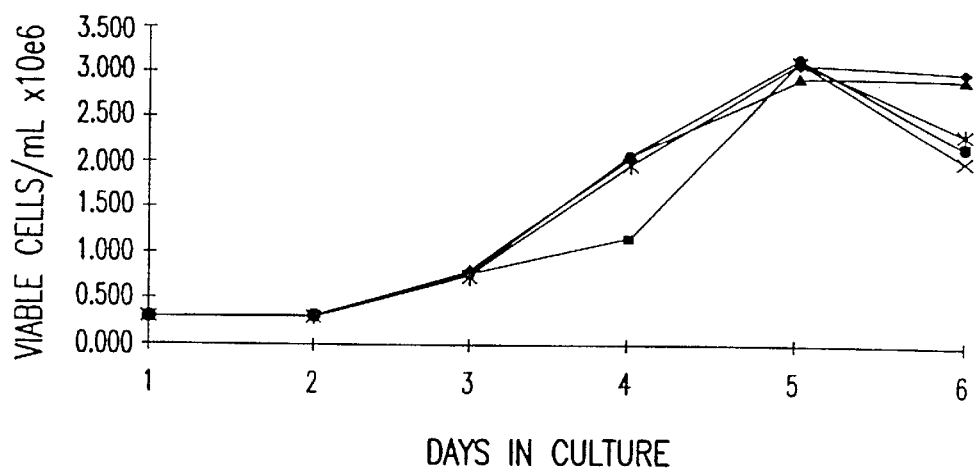
FIG. 16A: passage 1 cells.
Figure 16B:
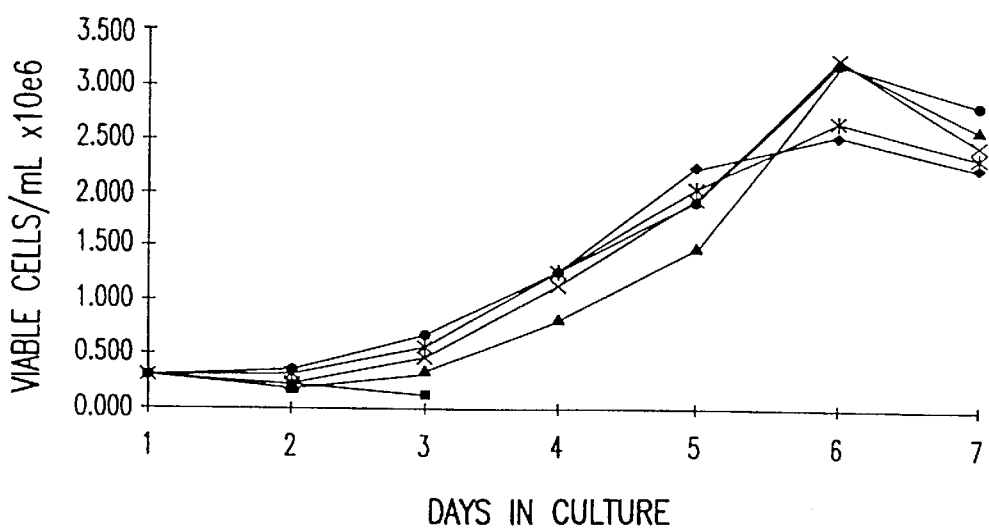
FIG. 16B: passage 2 cells.
Figure 16C:
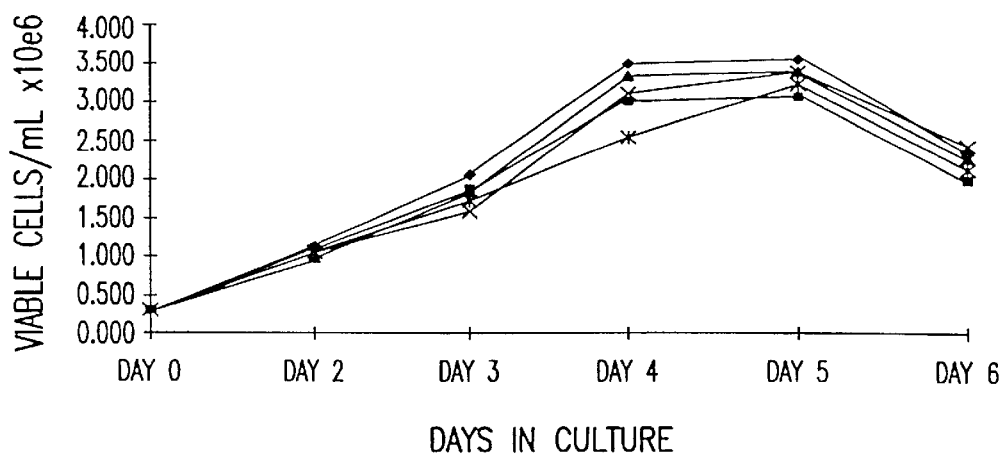
FIG. 16C: passage 3 cells.
Figure 16D:
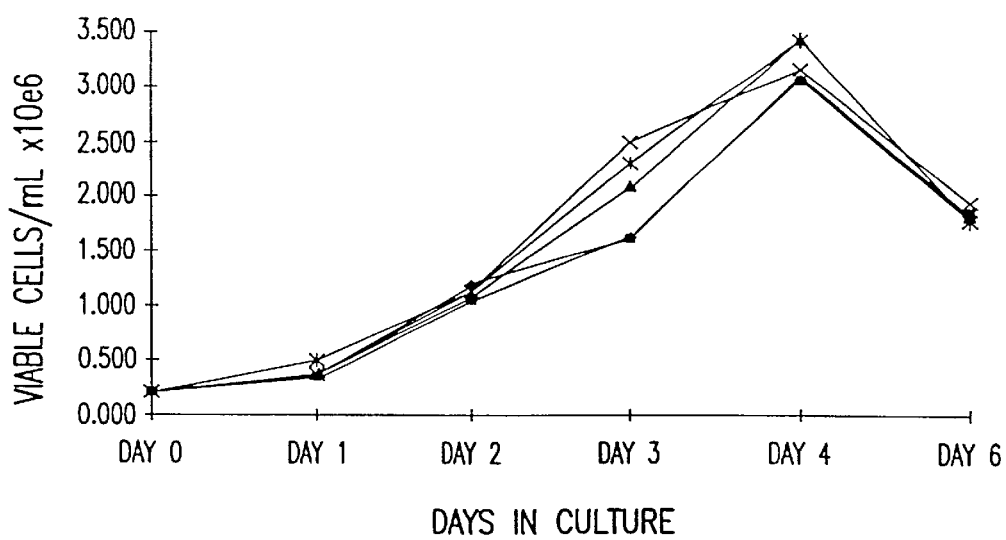
FIG. 16D: passage 4 cells.

As shown in FIGS. 16A–16D, cells cultured in media containing transferrin that was γ irradiated at either −70° C. or at room temperature demonstrated nearly identical growth kinetics and survival in the first passage (FIG. 16A), second passage (FIG. 16B), third passage (FIG. 16C) and fourth passage (FIG. 16D) as did cells cultured in standard 293 SFM or in 293 SFM containing transferrin that had not been γ irradiated. Cells cultured in transferrin-free media, however, survived well during the first passage (FIG. 16A) but stopped growing and demonstrated a significant loss in viability upon subculturing (FIG. 16B).

These results demonstrate that γ irradiation may be used as a sterilization technique in the preparation of bulk powdered culture media supplements, such as transferrin, in the methods of the present invention. Furthermore, these data indicate that culture media supplements such as transferrin may be γ irradiated at room temperature without significant loss of activity.

EXAMPLE 15

Effect of Irradiation on Biochemical Characteristics of Powdered Sera

To further determine the impact of γ irradiation on sera, samples of spray-dried powder FBS were irradiated at 25 kGy at −70° C. or at room temperature (RT), and were analyzed commercially for the concentrations of various biochemical constitutents in the sera. As controls, samples of non-irradiated spray-dried FBS and liquid FBS were also analyzed. Results are shown in Table 2.

TABLE 2

Chemical Analysis of Spray-Dried FBS

| Constituent | Dried FBS, Irr. @ −70° C. | Dried FBS, Irr. @ RT | Non-irradiated Dried FBS | Liquid FBS | Units | Reference Range |
|---|---|---|---|---|---|---|
| Sodium | 139 | 137 | 139 | 140 | mM | 136–144 |
| Potassium | 13.2 | 13.2 | 13.0 | 13.2 | mM | 3.6–5.2 |
| Chloride | 98 | 97 | 98 | 100 | mM | 98–108 |
| Uric Acid | 1.6 | 1.3 | 1.7 | 1.9 | mg/dL | 2.2–8.3 |
| Phosphorus | 10.1 | 10.1 | 9.6 | 10.2 | mg/dL | 2.2–4.6 |
| Calcium | 14.9 | 14.8 | 14.8 | 14.5 | mg/dL | 8.6–10.2 |
| Ionizable Calcium | >5.5 | >5.5 | >5.5 | >5.5 | mg/dL | 3.8–4.5 |
| Magnesium | 2.77 | 2.76 | 2.75 | 2.76 | meq/L | 1.4–2.0 |
| Alkaline Phosphatase | 57 | 47 | 68 | 269 | U/L | 31–142 |
| Gamma GT (GGTP) | 3 | 5 | <5 | 5 | U/L | 1–60 |

TABLE 2-continued

Chemical Analysis of Spray-Dried FBS

| Constituent | Dried FBS, Irr. @ −70° C. | Dried FBS, Irr. @ RT | Non-irradiated Dried FBS | Liquid FBS | Units | Reference Range |
|---|---|---|---|---|---|---|
| AST (SGOT) | 7 | 5 | 5 | 33 | U/L | 1–47 |
| ALT (SGPT) | 5 | <5 | <5 | 7 | U/L | 1–54 |
| LD | 56 | <50 | 50 | 510 | U/L | 110–250 |
| Total Bilirubin | 0.19 | 0.24 | 0.22 | 0.13 | mg/dL | 0.2–1.4 |
| Direct Bilirubin | 0.04 | 0.07 | 0.07 | 0.04 | mg/dL | 0.0–0.3 |
| Glucose | 67 | 38 | 39 | 88 | mg/dL | 65–125 |
| BUN | 15 | 15 | 15 | 15 | mg/dL | 6–23 |
| Creatinine | 2.98 | 3.08 | 3.1 | 2.77 | mg/dL | 0.1–1.7 |
| BUN/Creatine Ratio | 5.0 | 4.9 | 4.8 | 5.4 | — | 7.0–20.0 |
| Total Protein | 3.6 | 3.6 | 3.5 | 3.7 | gm/dL | 6.4–8.1 |
| Albumin | 2.7 | 2.7 | 2.8 | 2.8 | gm/dL | 3.7–5.1 |
| Globulin | 0.9 | 0.9 | 0.7 | 0.9 | gm/dL | 2.1–3.6 |
| Albumin/Globulin Ratio | 3.0 | 3.0 | 4.0 | 3.1 | — | 1.1–2.3 |
| Cholesterol | 30 | 30 | 32 | 30 | mg/dL | <200 |
| HDL Cholesterol | 28 | 30 | 30 | 27 | mg/dL | 39–90 |
| Chol/HDL Ratio | 1.07 | 1.00 | 1.07 | 1.11 | — | <4.5 |
| Iron | 213 | 217 | 214 | 186 | meg/dL | 40–175 |
| Plasma Hb | 13.3 | 11.5 | 13.7 | 22.6 | mg/dL | 3.4–20.5 |

These results indicate that the γ irradiation process did not significantly affect the concentrations of most of the biochemical constituents of FBS. These results also indicate that upon spray-drying, several of the components of FBS (alkaline phosphatase, AST, and LD, and possibly glucose) undergo a significant reduction in concentration compared to their concentrations in the starting liquid FBS.

EXAMPLE 16

Effects of Irradiation on Performance of Powdered Sera

To examine the impact of γ irradiation on the ability of dried powder sera to support cell growth, samples of spray-dried FBS irradiated under various conditions were used to supplement culture media, and adherent and suspension cells were grown for up to three passages in these media. As model suspension cells, the hybridoma lines SP2/0 and AE-1 were used, while VERO and BHK cultures were used as typical adherent cells. Cells were cultured in media containing test sera or control sera (spray-dried but not irradiated) for up to three passages according to the general procedures outlined in Example 14 above. At each passage point, cells were harvested and subcultured, while an aliquot was counted as above for viable cells/ml. Results at each point were expressed as a percentage of the viable cell count obtained in media supplemented with liquid FBS, and are shown in FIGS. 17A, 17B, 17C and 17D.

Figure 17A:
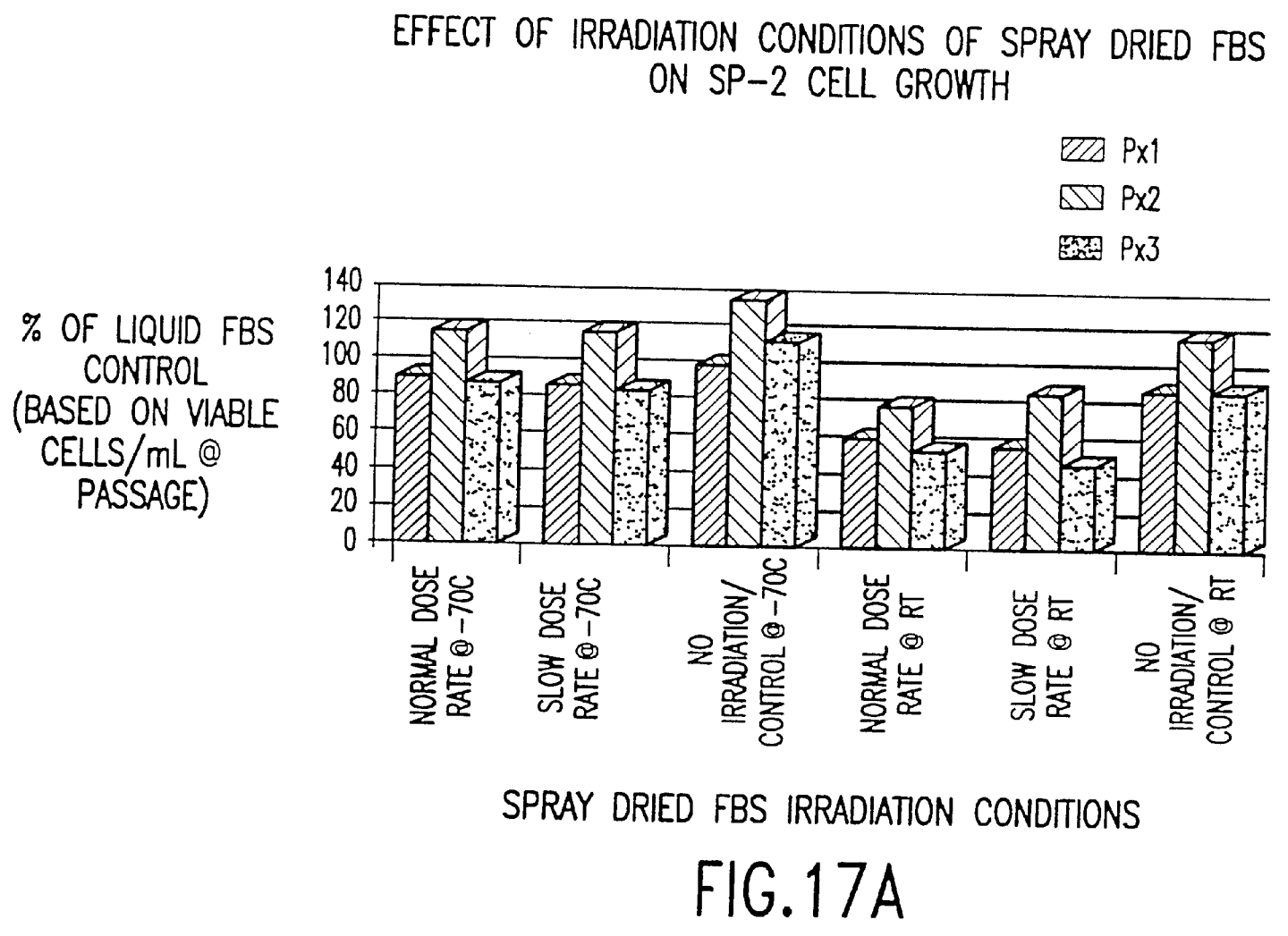
Figure 17B:
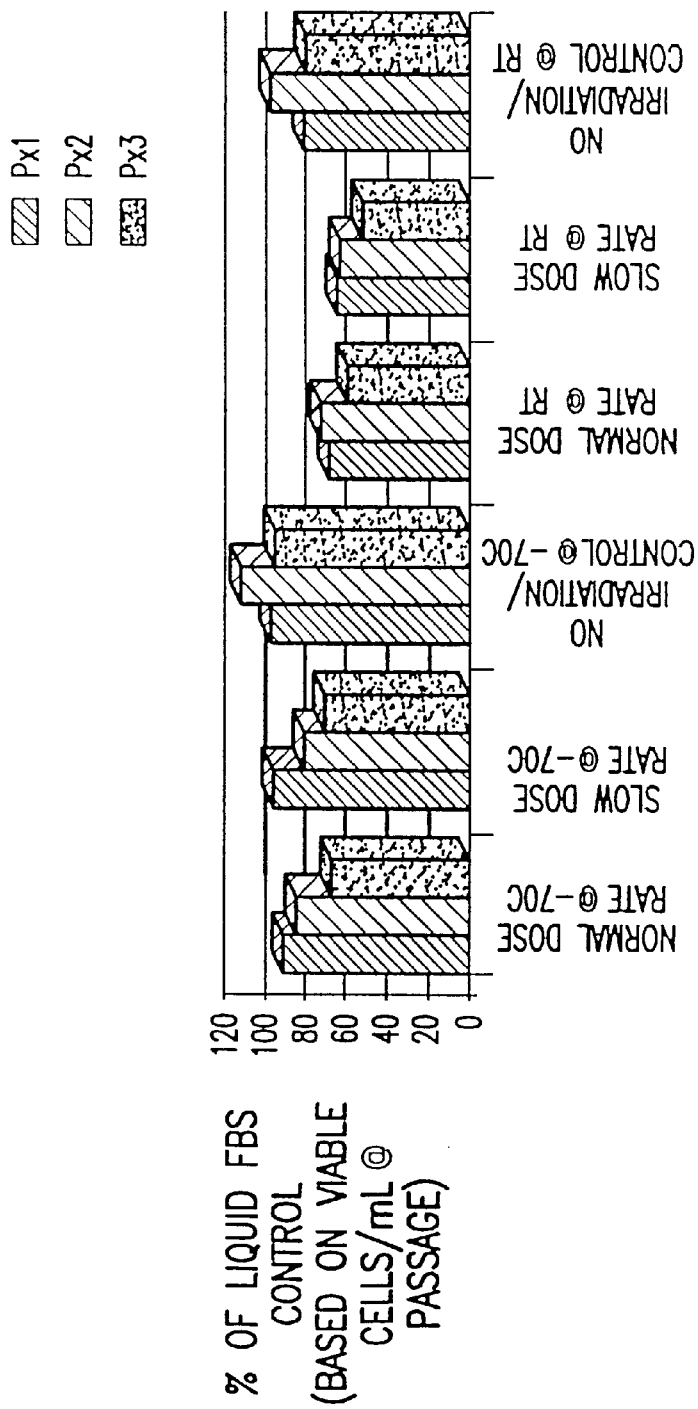
FIG. 17B: AE-1 cells.
Figure 17C:
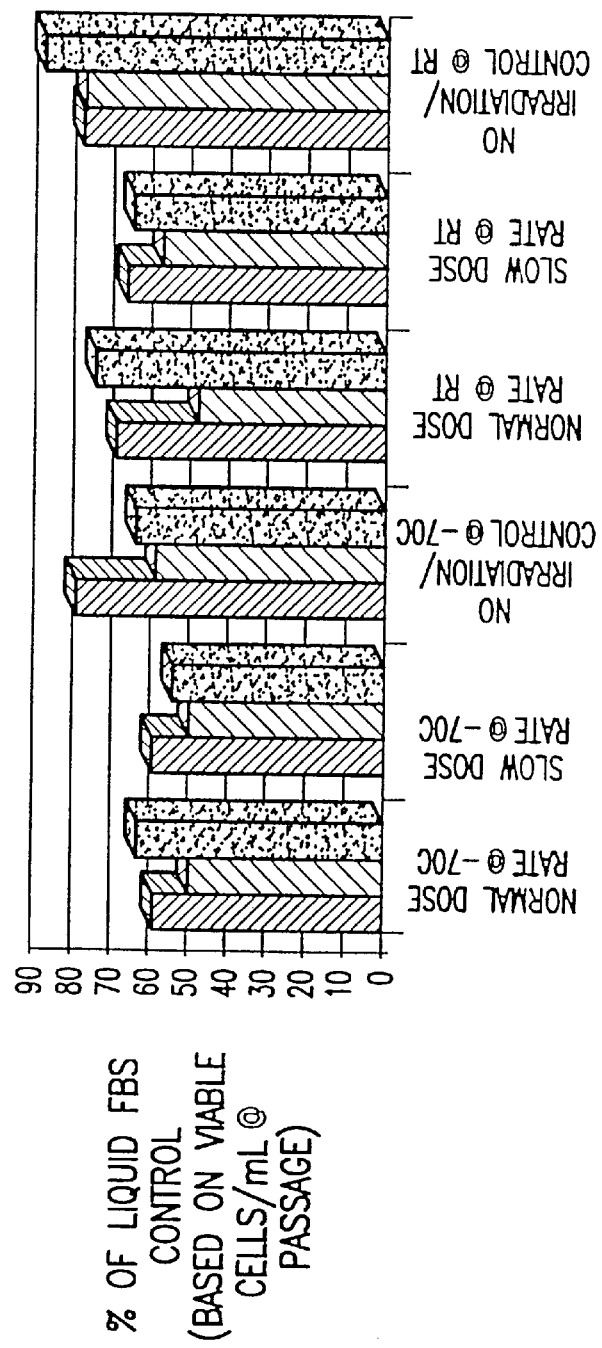
FIG. 17C: VERO cells.
Figure 17D:
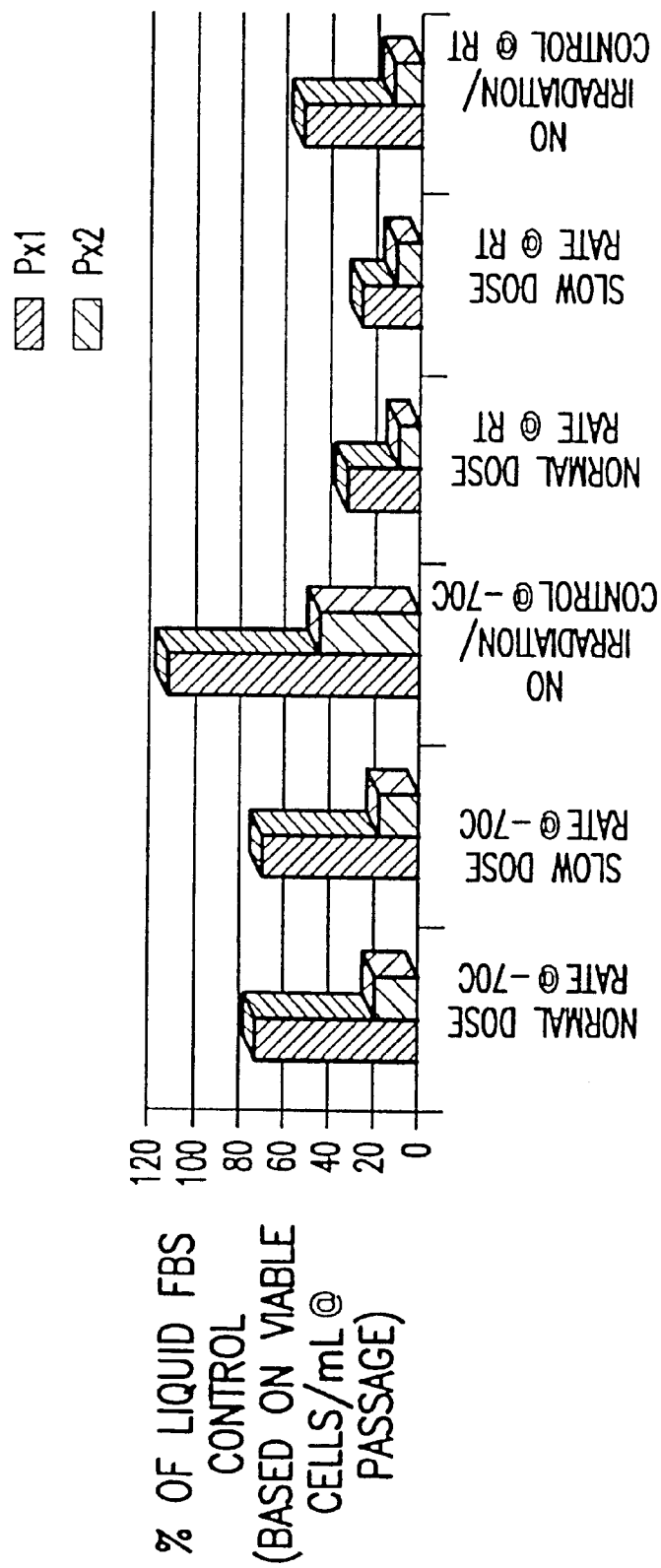
FIG. 17D: BHK cells.

Several conclusions may be drawn from the results of these studies. First, γ irradiation of FBS does not appear (with most cell lines) to reduce the ability of spray-dried FBS to support the growth of suspension and adherent cells (compare the irradiated data sets to the non-irradiated data set in each figure). That is, with most cell lines, growth promotion is comparable for irradiated and non-irradiated serum. Second, sera irradiated at −70° C. appear to perform better than those irradiated at room temperature in their ability to support cell growth, except perhaps for VERO cells (FIG. 17C). Finally, the results of these studies were very cell type-specific: suspension cells (FIGS. 17A and 17B) grew better in spray-dried FBS, irradiated and non-irradiated, than did adherent cells (FIGS. 17C and 17D).

These results demonstrate that γ irradiation may be used as a sterilization technique in the preparation of bulk powdered sera, such as FBS, in the methods of the present invention. Furthermore, unlike those reported for transferrin in Example 14 above, these data suggest that the optimal temperature for irradiation of sera, in order to maintain the ability of the sera to support cell growth, is likely to be below room temperature.

EXAMPLE 17

Viral Titer Reduction by Spray-Drying

The feasibility of reducing viral titer by spray-dry technology was examined. A three foot diameter laboratory spray dryer (Mobile Minor Spray Dryer, NIRO, Columbia, Md.) was used to prepare the powdered serum. Liquid FBS was spiked with virus at a known concentration (IBR virus@$10^{6.5}$ $TCID_{50}$/mL, REO virus@$10^5$ $TCID_{50}$/mL and naturally contaminated with BVDv@a++ detection level). The virus spiked liquid FBS was aspirated into the spray-dryer and atomized through a Schlick 940 nozzle located in the middle of the air disperser, and the drying air was introduced into the chamber through the top air disperser of the the apparatus. Spray drying was conducted under the following conditions: inlet air temperature=148°to 215° C.; outlet temperature=50° to 80° C., atomizing air pressure for the nozzle=1.6 to 2.0 bar; air flow=80.0 kg/hour; spray rate=2 kg/hour. Following spray-drying, powdered serum was collected at the cyclone of the apparatus, and process air was exhausted.

Following production, the powdered serum was reconstituted to a 1× liquid with distilled water (60 gm powdered serum=one liter liquid FBS). This reconstituted 1× liquid Spray-Dry processed serum was characterized with respect to viral titer and compared to the non-processed liquid FBS from the same virus spiked lot with known viral concentration using the following viral titer detection procedure. Using a cell line known to be sensitive to assayed virus, $1\times10^4$ cells are plated per well of a 96 well plate. The sample to be assayed is diluted through a series of 10 fold dilutions out to $10^{-10}$. Aliquots (0.1 ml) of each dilution are added to replicate wells of the cell line inoculated plate. The cells in each well are evaluated for cytopathic effect (CPE) after 4 to 7 days. Results are evaluated using the method of Reed, L J and Muench, H. (Am. J. Hyg. 1938:27:493) and expressed as tissue culture infective dose ($TCID_{50}$/mL) sample material. BVDv tested by the cell culture method over three passages, and final antigen detection by direct fluorescent assay (9CFR).

Results are shown in Table 3, Table 4, Table 5 and Table 6 for reduction of viral titer by Spray-Dry processing of powdered FBS. Conclusion: Spray-Drying process was effective in inactivation of IBR virus with a total titer reduction of at least $10^{-6}$, of REO virus with a total titer reduction of at least $10^{-5}$, and of BVDv inactivation of the naturally contaminating virus from ++ to negative. Together, these results indicate that serum powder prepared by the present spray-drying methods have significantly reduced viral titer. These results demonstrate that the methods provided by the present invention result in the production of powdered serum with $10^{-6}$ reduction in viral titer.

TABLE 3

IBR Viral Titer of Powdered Serum Prior to and Post Spray-Drying Treatment

| Prior to Spray Drying Process IBR "spiked" FBS Control | Post Spray Drying Process Spray-dried* IBR "spiked" FBS |
|---|---|
| $10^{-1}$ | + | − |
| $10^{-2}$ | + | − |
| $10^{-3}$ | + | − |
| $10^{-4}$ | + | − |
| $10^{-5}$ | + | − |
| $10^{-6}$ | + | − |
| $10^{-7}$ | +/− | na |

*Spray-Dry @ inlet temperature = 150° C.; outlet temperature = 70° C.
Results Summary: Spray-Dried FBS: negative, no virus detected after spray drying.
Control, virus "spiked" FBS = Positive. Virus titer = $1 \times 10^{6.5}$.

TABLE 4

BVD Viral Titer of powdered Serum Prior to and Post Spray-Drying Treatment

| Prior to Spray Dry Processing | Post Spray Dry Processing |
|---|---|
| Spray-Dried BVDV positive FBS (215°/80° C.)* | Negative (BT cells) |
| Spray-Dried BVDV positive FBS (150°/50° C.)** | Negative (BT cells) |
| Non-treated BVDV positive FBS | Positive (++)(BT cells) |

*Spray-Dry @ inlet temperature = 215° C.; outlet temperature = 80° C.
**Spray-Dry @ inlet temperature = 150° C.; outlet temperature = 70° C.
Results Summary: Spray-Dried FBS: negative, no virus detected after spray drying using either set of processing temperatures tested.

TABLE 5

REO Viral Titer of Powdered Serum Prior to and Post Spray Drying Treatment

| Prior to Spray Drying Process Reovirus 3 "spiked" FBS Control | Post Spray Drying Process Spray-dried* Reovirus 3 "spiked" FBS |
|---|---|
| $10^{-1}$ | + | − |
| $10^{-2}$ | + | − |
| $10^{-3}$ | + | − |
| $10^{-4}$ | + | − |
| $10^{-5}$ | + | − |
| $10^{-6}$ | − | − |
| $10^{-7}$ | − | − |
| $10^{-8}$ | − | − |

*Spray-Dry @ inlet temperature = 150° C.; outlet temperature = 70° C.
Results Summary: Spray-Dried FBS: negative, no virus detected after spray drying.
Control, virus "spiked" FBS = Positive. Virus titer = $1 \times 10^5$.

TABLE 6

FBS Viral Titer Reduction

| Virus Tested | Viral Load Tested | Virus Reduction |
|---|---|---|
| IBR Virus | $10^{6.5}$ $TCID_{50}$/mL | $\geq 6$ Log 10 |
| BVD Virus | ++ | Negative |
| REO Virus | $10^5$ $TCID_{50}$/mL | $\geq 5$ Log 10 |

EXAMPLE 18

Endotoxin Reduction by Spray-Drying

The feasibility of reducing endotoxin concentration by spray-dry technology was examined. A three foot diameter laboratory spray dryer (Mobile Minor Spray Dryer, NIRO, Columbia, Md.) was used to prepare the powdered serum. A lot of Liquid FBS was identified with elevated endotoxin levels. The endotoxin containing liquid FBS was aspirated into the spray-dryer and atomized through a Schlick 940 nozzle located in the middle of the air disperser, and the drying air was introduced into the chamber through the top air disperser of the apparatus. Spray drying was conducted under the following conditions: inlet air temperature=148° to 215° C.; outlet temperature=50° to 80° C., atomizing air pressure for the nozzle=1.6 to 2.0 bar; air flow=80.0 kg/hour; spray rate=2 kg/hour. Following spray-drying, powdered serum was collected at the cyclone of the apparatus, and process air was exhausted.

Following production, the powdered serum was reconstituted to a 1× liquid with distilled water (60 gm powdered serum=one liter liquid FBS). The endotoxin concentration of this reconstituted 1× liquid Spray-Dry processed serum was determined and compared to the endotoxin level of non-processed liquid FBS from the same lot using the Limulus Amebocyte Lysate (LAL) test. Briefly, the LAL test is a gel clot test conducted by mixing LAL reagent and test sample and observing for gelation after 60 minutes at 37° C. See generally "*Pyrogens, Endotoxins, LAL Testing, Depyrogenation*" (J. Robinson, ed.) Marcel Dekker, Inc., New York. A positive response (gel formation) indicates that there is an amount of endotoxin in the sample which meets or exceeds the reagents labeled sensitivity. Results are reported in endotoxin units per mL. All endotoxin is measured in units by comparison to the reference standard endotoxin.

Results are shown in the table below for the reduction of endotoxin concentration by Spray-Dry processing of FBS.

Conclusion: Spray-Drying process was effective in reducing the endotoxin concentration with an endotoxin concentration reduction of 50% from 48.0 EU/mL to 24.0 EU/mL. These results indicate that serum powder prepared by the present spray-drying methods have significantly reduced endotoxin levels. These results demonstrate that the methods provided by the present invention result in the production of powdered serum with reduced endotoxin level.

Endotoxin Test Results
of Spray Dried Processed FBS

| Sample Description | Endotoxin Level (EU/mL) |
| --- | --- |
| Spray Dried Processed FBS | 24.0 |
| Control FBS (Non-spray dried processed FBS) | 48.0 |
| H$_2$O used to reconstitute Spray Dried Processed FBS | <0.03 |

| Conditions used: | |
| --- | --- |
| inlet temperature | 150° C. |
| outlet temperature | 60° C. |
| atomizing pressure | 1.6 Bar |
| spray rate | 1.51 kg/hr |

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for reducing one or more adventitious agents or toxins in a sample, said method comprising subjecting a powdered sample to fluid bed agglomeration under conditions sufficient to reduce one or more adventitious agents or one or more toxins in said sample;
   wherein said powdered sample is selected from the group consisting of yeast culture media, plant culture media, animal culture media and buffers; and
   wherein said one or more toxins are selected from the group consisting of endotoxin, exotoxins, snake or animal venom, cholera toxin, leukocidin, Ricin A, poisons derived from animals, neurotoxin, and erythrogenic toxin.

2. The method of claim 1, wherein said fluid bed agglomeration comprises:
   (a) subjecting said powdered sample to suspension in a moving column of a gas or combination of gases;
   (b) injecting one or more solvents into said powdered sample to produce a moistened powder; and
   (c) drying the moistened powder to produce a dried agglomerated sample.

3. The method of claim 2, wherein said powdered sample is heated.

4. The method of claim 2, wherein said gas or combination of gases is heated.

5. The method of claim 2, further comprising passing said powdered sample through one or more filters.

6. The method of claim 1, wherein said powdered sample comprises one or more components selected from the group consisting of serum, L-glutamine, cystine, insulin, transferrin, lipid, carbohydrate, cytokine, neurotransmitter and sodium bicarbonate.

7. The method of claim 2, wherein said gas or combination of gases are toxic or inhibitory to said one or more adventitious agents, or inhibitory to said one or more toxins.

8. The method of claim 2, wherein said gas or combination of gases is selected from the group consisting of nitrogen, helium, air, carbon dioxide, argon, oxygen, and hydrogen.

9. The method of claim 2, wherein said one or more solvents are toxic or inhibitory to said one or more adventitious agents, or inhibitory to said one or more toxins.

10. The method of claim 2, wherein said one or more solvents are selected from the group consisting of: water; serum; organic solvents; blood derived products; extracts or hydrolysates of tissues, organs, glands or cells; animal derived products; media supplements; buffers; acids and bases.

11. The method of claim 10, wherein said one or more solvents contain one or more additional components selected from the group consisting of salts, polysaccharides, ions, detergents and stabilizers.

12. The method of claim 2, wherein said one or more solvents have incorporated into them one or more components selected from the group consisting of serum, hormones, cytokines, neurotransmitters, lipids, carbohydrates, attachment factors, proteins, amino acids, vitamins and enzyme cofactors.

13. The method of claim 1, wherein said adventitious agents are selected from the group consisting of animal, human, plant, fish, insect, and mammalian viruses.

14. The method of claim 1, wherein said buffers are selected from the group consisting of phosphate-buffered saline and tris-buffered saline.

15. The method of claim 1, wherein said powdered sample is a yeast culture medium.

16. The method of claim 1, wherein said powdered sample is a plant culture medium.

17. The method of claim 1, wherein said powdered sample is an animal culture medium.

18. The method of claim 1, wherein said powdered sample is a buffer.

19. The method of claim 18, wherein said buffer is selected from the group consisting of phosphate-buffered saline and tris-buffered saline.

* * * * *